United States Patent
Zander et al.

(10) Patent No.: US 8,475,765 B2
(45) Date of Patent: *Jul. 2, 2013

(54) HYDROXYALKYL STARCH DERIVATIVES

(75) Inventors: Norbert Zander, Meine (DE); Harald Conradt, Braunschweig (DE); Wolfram Eichner, Butzbach (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 171 days.

This patent is subject to a terminal disclaimer.

(21) Appl. No.: 12/855,381

(22) Filed: Aug. 12, 2010

(65) Prior Publication Data

US 2011/0054152 A1    Mar. 3, 2011

Related U.S. Application Data

(60) Division of application No. 11/077,906, filed on Mar. 11, 2005, now Pat. No. 7,815,893, which is a continuation-in-part of application No. PCT/EP03/08859, filed on Aug. 8, 2003.

(60) Provisional application No. 60/409,781, filed on Sep. 11, 2002.

(30) Foreign Application Priority Data

Sep. 11, 2002  (EP) .................................... 02020425

(51) Int. Cl.
*A61K 51/00* (2006.01)
*A61K 38/00* (2006.01)
*A61K 38/16* (2006.01)
*A61M 36/14* (2006.01)
*A01N 37/18* (2006.01)
*C07H 1/00* (2006.01)
*C07H 3/00* (2006.01)
*C08B 37/00* (2006.01)
*C08B 31/00* (2006.01)
*C08B 33/00* (2006.01)
*C08B 35/00* (2006.01)

(52) U.S. Cl.
USPC ........ 424/1.73; 424/1.41; 424/1.45; 536/102; 536/124; 536/106; 514/1.1; 514/20.9

(58) Field of Classification Search
USPC ........ 424/1.73, 1.41, 1.45; 514/2, 8; 536/102, 536/124, 106
See application file for complete search history.

(56) References Cited

U.S. PATENT DOCUMENTS

| | | |
|---|---|---|
| 3,191,291 A | 6/1965 | Maier |
| 3,226,395 A | 12/1965 | Schimmelschmidt et al. |
| 4,001,200 A | 1/1977 | Bonsen et al. |
| 4,001,401 A | 1/1977 | Bonsen et al. |
| 4,053,590 A | 10/1977 | Bonsen et al. |
| 4,061,736 A | 12/1977 | Morris et al. |
| 4,064,118 A | 12/1977 | Wong |
| 4,125,492 A | 11/1978 | Cuatrecasas et al. |
| 4,179,337 A | 12/1979 | Davis et al. |
| 4,261,973 A | 4/1981 | Lee et al. |
| 4,412,989 A | 11/1983 | Iwashita et al. |
| 4,454,161 A | 6/1984 | Okada et al. |
| 4,496,689 A | 1/1985 | Mitra |
| 4,667,016 A | 5/1987 | Lai et al. |
| 4,703,008 A | 10/1987 | Lin |
| 4,766,106 A | 8/1988 | Katre et al. |
| 4,847,325 A | 7/1989 | Shadle et al. |
| 4,863,964 A | 9/1989 | Hedlund et al. |
| 4,900,780 A | 2/1990 | Cerny |
| 4,904,584 A | 2/1990 | Shaw |
| 4,925,677 A | 5/1990 | Feijen |
| 4,939,239 A | 7/1990 | Matsuhashi et al. |
| 4,952,496 A | 8/1990 | Studier et al. |
| 5,068,321 A | 11/1991 | Buysch et al. |
| 5,073,628 A | 12/1991 | Matsuhashi et al. |
| 5,079,337 A | 1/1992 | Leonard et al. |
| 5,110,909 A | 5/1992 | Dellacherie et al. |
| 5,214,132 A | 5/1993 | Kuga et al. |
| 5,217,998 A | 6/1993 | Hedlund et al. |

(Continued)

FOREIGN PATENT DOCUMENTS

| | | |
|---|---|---|
| AU | 5238393 | 6/1994 |
| CA | 2110543 | 2/1993 |
| CA | 2233725 | 9/1999 |
| CA | 2441442 | 10/2002 |
| CA | 2478478 | 9/2003 |
| CA | 2478480 | 9/2003 |

(Continued)

OTHER PUBLICATIONS

Peluso, S., Imperiali, B. (2001) Asparagine surrogates for the assembly of N-linked glycopeptide mimetics by chemoselective ligation. Tetrahedron Letters, vol. 42, p. 2085-2087.*

(Continued)

Primary Examiner — Scarlett Goon
(74) Attorney, Agent, or Firm — Occhiuti Rohlicek & Tsao LLP

(57) ABSTRACT

The present invention relates to a method of producing a hydroxyalkyl starch derivative comprising reacting hydroxyalkyl starch of formula (I) at its reducing end which is not oxidized prior to said reaction, with a compound of formula (II) R'NH—R" (II) wherein $R_1$-$R_2$ and $R_3$ are independently hydrogen or a linear or branched hydroxyalkyl group, and wherein either R' or R" or R' and R" comprise at least one functional group X capable of being reacted with at least one other compound prior to or after the reaction of (I) and (II), as well as to the hydroxyalkyl starch derivative as such, obtainable by said method, and to a pharmaceutical composition comprising said hydroxyalkyl starch derivative.

35 Claims, 22 Drawing Sheets

U.S. PATENT DOCUMENTS

Figure 1:
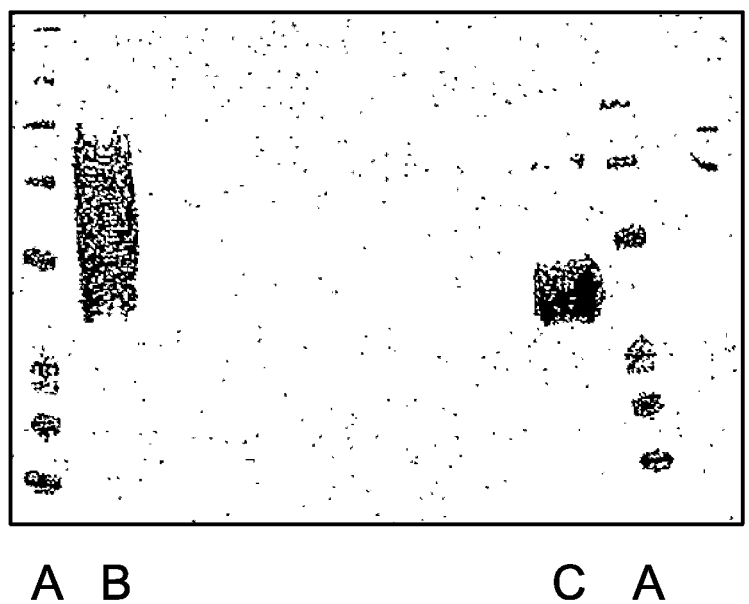

| | | | |
|---|---|---|---|
| 5,218,092 A | 6/1993 | Sasaki et al. |
| 5,218,108 A | 6/1993 | Sommermeyer et al. |
| 5,281,698 A | 1/1994 | Nitecki |
| 5,342,770 A | 8/1994 | Yamasaki |
| 5,362,853 A | 11/1994 | Kuga |
| 5,420,105 A | 5/1995 | Gustavson et al. |
| 5,470,843 A | 11/1995 | Stahl et al. |
| 5,484,903 A | 1/1996 | Szablikowski et al. |
| 5,543,332 A | 8/1996 | Lihme et al. |
| 5,581,476 A | 12/1996 | Osslund |
| 5,622,718 A | 4/1997 | Al-Shamkhani et al. |
| 5,723,589 A | 3/1998 | Miljkovic et al. |
| 5,736,533 A | 4/1998 | Simon et al. |
| 5,770,645 A | 6/1998 | Stamler |
| 5,824,778 A | 10/1998 | Ishikawa et al. |
| 5,840,900 A | 11/1998 | Greenwald |
| 5,847,110 A | 12/1998 | Dragsten et al. |
| 5,851,984 A | 12/1998 | Matthews et al. |
| 5,876,980 A | 3/1999 | DeFrees |
| 5,880,270 A | 3/1999 | Berninger et al. |
| 5,952,347 A | 9/1999 | Arison et al. |
| 5,977,163 A | 11/1999 | Li et al. |
| 5,981,507 A | 11/1999 | Josephson et al. |
| 5,990,237 A | 11/1999 | Bentley et al. |
| 6,011,008 A | 1/2000 | Domb et al. |
| 6,083,909 A | 7/2000 | Sommermeyer et al. |
| 6,172,208 B1 | 1/2001 | Cook |
| 6,261,800 B1 | 7/2001 | Nikolics et al. |
| 6,299,881 B1 | 10/2001 | Lees et al. |
| 6,340,746 B1 | 1/2002 | Roberts et al. |
| 6,375,846 B1 | 4/2002 | Jarrett et al. |
| 6,395,266 B1 | 5/2002 | Martinez et al. |
| 6,417,347 B1 | 7/2002 | Herrmann |
| 6,451,337 B1 | 9/2002 | Smith et al. |
| 6,500,930 B2 | 12/2002 | Adamson |
| 6,544,503 B1 | 4/2003 | Vanderhoff |
| 6,555,660 B2 | 4/2003 | Nissen |
| 6,586,398 B1 | 7/2003 | Kinstler |
| 6,596,135 B1 | 7/2003 | Mitsui |
| 6,596,861 B1 | 7/2003 | Moreau |
| 6,624,142 B2 | 9/2003 | Muir et al. |
| 6,660,843 B1 | 12/2003 | Feige et al. |
| 6,875,594 B2 | 4/2005 | Muir et al. |
| 6,916,962 B2 | 7/2005 | Rosen et al. |
| 7,115,576 B2 | 10/2006 | Sommermeyer |
| 7,125,843 B2 | 10/2006 | DeFrees et al. |
| 7,157,546 B2 | 1/2007 | Kozlowski |
| 7,179,617 B2 | 2/2007 | DeFrees et al. |
| 7,279,176 B1 | 10/2007 | West |
| 7,285,661 B2 | 10/2007 | Sommermeyer et al. |
| 7,538,092 B2 | 5/2009 | Orlando et al. |
| 7,541,328 B2 | 6/2009 | Hemberger |
| 7,629,456 B2 | 12/2009 | Lange et al. |
| 7,815,893 B2 | 10/2010 | Zander et al. |
| 7,816,516 B2 | 10/2010 | Sommermeyer et al. |
| 8,017,739 B2 | 9/2011 | Eichner et al. |
| 2002/0065410 A1 | 5/2002 | Antrim |
| 2003/0087877 A1 | 5/2003 | Calias et al. |
| 2003/0191291 A1 | 10/2003 | Kochendoerfer et al. |
| 2004/0023306 A1 | 2/2004 | Aebersold et al. |
| 2005/0181985 A1 | 8/2005 | Hemberger et al. |
| 2005/0238723 A1 | 10/2005 | Zander et al. |
| 2006/0019877 A1 | 1/2006 | Conradt et al. |
| 2006/0121062 A1 | 6/2006 | Eichner et al. |
| 2006/0188472 A1 | 8/2006 | Sommermeyer et al. |
| 2006/0194940 A1 | 8/2006 | Kozlowski |
| 2006/0217293 A1 | 9/2006 | Orlando et al. |
| 2007/0087961 A1 | 4/2007 | Eichner et al. |
| 2007/0134197 A1 | 6/2007 | Eichner et al. |
| 2008/0206182 A1 | 8/2008 | Sommermeyer et al. |
| 2008/0207562 A1 | 8/2008 | Zander et al. |
| 2008/0274948 A1 | 11/2008 | Eichner et al. |
| 2009/0091549 A1 | 4/2009 | Matsumoto et al. |
| 2009/0233847 A1 | 9/2009 | Hemberger et al. |

FOREIGN PATENT DOCUMENTS

| | | |
|---|---|---|
| DE | 22 33 977 | 2/1973 |
| DE | 2607706 | 1/1977 |
| DE | 2646854 | 5/1977 |
| DE | 26 16 086 | 11/1977 |
| DE | 30 29 307 | 3/1982 |
| DE | 3501616 | 7/1986 |
| DE | 38 36 600 | 7/1989 |
| DE | 279 486 | 6/1990 |
| DE | 41 30 807 | 3/1993 |
| DE | 69025920 | 8/1996 |
| DE | 196 28 705 | 1/1998 |
| DE | 198 08 079 | 8/1999 |
| DE | 100 41 541 | 3/2002 |
| DE | 101 12 825 | 10/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 7/1985 |
| EP | 0 218 825 | 4/1987 |
| EP | 0 307 827 | 3/1989 |
| EP | 0 138 572 | 7/1990 |
| EP | 0 148 605 | 7/1990 |
| EP | 0 205 564 | 5/1991 |
| EP | 0 411 678 | 1/1992 |
| EP | 0 127 839 | 7/1992 |
| EP | 0 338 916 | 7/1992 |
| EP | 0 331 471 | 12/1992 |
| EP | 0 315 349 | 2/1993 |
| EP | 0 549 721 | 4/1994 |
| EP | 0 304 183 | 6/1994 |
| EP | 0 605 963 | 7/1994 |
| EP | 0 609 968 | 8/1994 |
| EP | 0 342 557 | 11/1994 |
| EP | 0 640 619 | 3/1995 |
| EP | 0 646 130 | 4/1995 |
| EP | 0 418 523 | 6/1995 |
| EP | 0 661 294 | 7/1995 |
| EP | 0 668 351 | 8/1995 |
| EP | 0 243 929 | 9/1995 |
| EP | 0 402 724 | 2/1996 |
| EP | 0 428 267 | 12/1996 |
| EP | 0 806 140 | 11/1997 |
| EP | 0 809 996 | 12/1997 |
| EP | 1 398 322 | 3/2004 |
| EP | 1 398 327 | 3/2004 |
| EP | 1 398 328 | 3/2004 |
| EP | 1 400 533 | 3/2004 |
| EP | 1 424 086 | 6/2004 |
| EP | 1496076 | 1/2005 |
| EP | 1 230 935 | 8/2005 |
| EP | 1 591 467 | 11/2005 |
| EP | 1 064 951 | 8/2007 |
| EP | 2 070 950 | 6/2009 |
| EP | 2 143 736 | 1/2010 |
| EP | 2 154 160 | 2/2010 |
| EP | 1 660 134 | 12/2010 |
| EP | 1372735 | 10/2011 |
| FR | 2 378 094 | 8/1978 |
| GB | 1 419 080 | 12/1973 |
| GB | 1 549 246 | 7/1979 |
| IL | 166506 | 2/2010 |
| JP | 10287554 | 10/1998 |
| JP | 2001-294601 | 10/2001 |
| WO | 80/02374 | 11/1980 |
| WO | WO 90/07939 | 7/1990 |
| WO | 90/12874 | 11/1990 |
| WO | WO 90/15628 | 12/1990 |
| WO | 92/11037 | 7/1992 |
| WO | WO 93/23062 | 11/1993 |
| WO | 93/24476 | 12/1993 |
| WO | WO 94/01483 | 1/1994 |
| WO | WO 94/05332 | 3/1994 |
| WO | WO 94/07536 | 4/1994 |

| | | |
|---|---|---|
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | 97/30148 | 8/1997 |
| WO | WO 97/30148 | 8/1997 |
| WO | WO 97/33552 | 9/1997 |
| WO | WO 97/38727 | 10/1997 |
| WO | 97/42225 | 11/1997 |
| WO | WO 98/01158 | 1/1998 |
| WO | 98/05689 | 2/1998 |
| WO | 98/07713 | 2/1998 |
| WO | WO 98/08856 | 3/1998 |
| WO | 98/14212 | 4/1998 |
| WO | 98/14215 | 4/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | 99/17783 | 4/1999 |
| WO | WO 99/49897 | 10/1999 |
| WO | 00/07738 | 2/2000 |
| WO | 00/18893 | 4/2000 |
| WO | WO0055210 | 9/2000 |
| WO | 00/66633 | 11/2000 |
| WO | WO 00/78355 | 12/2000 |
| WO | WO 01/70272 | 9/2001 |
| WO | 01/78682 | 10/2001 |
| WO | 01/83522 | 11/2001 |
| WO | WO 01/83522 | 11/2001 |
| WO | 01/93862 | 12/2001 |
| WO | WO 01/93862 | 12/2001 |
| WO | WO 02/09766 | 2/2002 |
| WO | WO 02/20033 | 3/2002 |
| WO | 02/28841 | 4/2002 |
| WO | WO 02/40057 | 5/2002 |
| WO | WO 02/080979 | 10/2002 |
| WO | WO 03/000738 | 1/2003 |
| WO | WO 03/031464 | 4/2003 |
| WO | WO 03/031581 | 4/2003 |
| WO | WO03/035665 | 5/2003 |
| WO | 03/049699 | 6/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | 2005/072778 | 8/2005 |
| WO | WO 2005/074993 | 8/2005 |
| WO | 2005/083103 | 9/2005 |
| WO | 2005/092369 | 10/2005 |
| WO | WO 2005/092390 | 10/2005 |
| WO | 2005/112954 | 12/2005 |
| WO | WO 2006/108052 | 10/2006 |
| WO | 2007/053292 | 5/2007 |
| WO | 2010/042638 | 4/2010 |

OTHER PUBLICATIONS

"Oxime" from McGraw-Hill's Access Science [online], [retrieved May 9, 2011]. Retrieved from the internet <http://accessscience.com/content.aspx?searchStr=oxime&id=480600>.*

Dörwald, F.Z. (2005) Side Reactions in Organic Synthesis, A Guide to Successful Synthesis Design. Published by Wiley-VCH Verlag GmbH & Co. Preface p. IX-X.*

Zogg, G.C., Nyiredy, Sz., Sticher, O. (1989) Preparative Medium Pressure Liquid Chromatographic (MPLC) and Semi-Preparative HPLC Separation of Furocoumarin Isomers. Chromatographia, vol. 27, No. 11/12, p. 591-595.*

Alagon et al., "Activation of Polysaccharides with 2-Iminothiolane and its Uses", Biochem. 19:4341-4345 (1980).

Balazy et al., "S-Nitroglutathione, a Product of the Reaction between Peroxynitrite and Glutathione That Generates Nitric Oxide", J. Biol. Chem. 273(48):32009-32015 (1998).

Etrych et al., "New HPMA Copolymers containing doxorubicin bound via pH-sensitive linkage: synthesis and preliminary in vitro and in vivo biological properties", Journal of Controlled Release 73:89-102 (2001).

Eur Phar., European Pharmacopeia 4, Monography Oct. 2002:1316; erythropoietin.

Schroeter et al., "Male-specific Modification of Human CD52," J. Biol. Chem., 1999, 274(42):29862-29873.

Ganson et al., "Control of Hyperuricemia in Subjects with refractory gout, and induction of antibody against poly (ethylene glycol) (PEG), in a phase I trial of subcutaneous PEGylated urate oxidase", Arthritis Research & Therapy, 8:R12 (2005).

Glederblom et al., "Cremophor EL: the drawbacks and advantages of vehicle selection for drug formulation", European Journal of Cancer, 37:1590-1598 (2001).

Gerwech et al., "Tumor pH controls the in vivo efficacy of weak acid and base chemotherapeutics", Mol. Cancer Ther. 5(5):1275-1279 (2006).

Greenwald et al., "Drug Delivery Systems: Water Soluble Taxol 2'-Poly(ethylene glycol) Ester Prodrugs—Design and in Vivo Effectiveness" J. Med. Chem., 39:424-431 (1996).

Hamilton et al., "Characterization of a Human Ovarian Carcinoma Cell Line (NIH:OVCAR-3) with Androgen and Estrogen Receptors", Cancer Research, 43:5379-5389 (1983).

Jungheinrich et al., "Pharmacokinetics of Hydroxyethyl Starch", Clin Pharmacokinet, 44(7):681-699 (2005).

Katsumi et al., "Development of Polyethylene Glycol-Conjugated Poly-S-Nitrosated Serum Albumin, a Novel S-Nitrosothiol for Prolonged Delivery of Nitric Oxide in the Blood Circulation in Vivo", Journal of Pharmacology and Experimental Therapeutics, 314(3):1117-1124 (2005).

Kinstler et al., "Characterization and Stability of N-terminally PEGylated rhG-CSF", Pharmaceutical Research, 13(7):996-1002 (1996).

Kulicke et al., "Measurements of the Refractive Index Increment on Hydroxyethyl Starch as a Basis for Absolute Molecutlar Weight Determinations", Starch, 43(10):392-396 (1991).

Laine et al., "Polyethylene Glycol Nephrotoxicity secondary to prolonged High-Dose Intravenous Lorazepam", Annals of Pharmacotherapy, 29:1110-1114 (1995).

Bernardes et al., "The Direct Formation of Glycosyl Thiols from Reducing Sugars Allows One-Pot Protein Glycoconjugation", Angew. Chem. 118:4111-4115 (2006).

Besheer et al., "Enzymatically Catalyzed HES Conjugation Using Microbial Transglutaminase:Proof of Feasibility", Journal of Pharmaceutical Sciences, 98(11):4420-4428 (2009).

Lund et al., Assessment of methods for covalent binding of nucleic acids to magnetic beads, Dynabeads, and the characteristics of the bound mucleic acids in hybrdization reactions Nuc; Acids Res., 16(22): 10861-10880, (1988).

Lee et al., "Functional Polymers for Layer-by-Layer Construction of Multilayer via Chemoselective Immobilization", Macromolecules, 37:1849-1856, (2004).

Lieber et al., "A Continuous Tumor-Cell Line From a Human Lung Carcinoma with Properties of Type II Alveolar Epithelial Cells", Int. J. Cancer, 17:62-70, (1976).

Lipke et al., "Localized Delivery of Nitric Oxide from Hydrogels Inhibits Neointima Formation in Rat Cartoid Ballon Injury Model", Acta Biomaterialia, 1:597-606, (2005).

Megson et al., "Inhibition of Human Platelet Aggregation by a Novel S-Nitrosothiol is Abolished by Haemoglobin and Red Blood Cell in vitro: Implications for Anti-Thrombotic Therapy", British Journal of Pharmacology, 131:1391-1398, (2000).

Nathan et al., "Strategies for Covalent Attachment of Doxorubicin to Poly(PEG-Lys), a New Water Soluble Poly(ether urethane)", Journal of Bioactive and Compatible Polymers, 9:239-251 (1994).

Naundorf et al., "Characterization of two human mammary carcinomas, MT-1 and MT-3, suitable for in vivo testing of either lipids and their dirivatives", Breast Cancer Research and Treatment, 23:87-95, (1992).

Ph. Eur. Nachtrag, "Erythropoietini solutio concentrata", pp. 780, (2000).

Ph. Eur. Nachtrag, "Erythropoietini solutio concentrata", pp. 911, (2001).

Pharmeuropa, "erythropoietin Concentrated Solution", 8(3):371. (1996).

Reynolds et al., "S-nitrosohemoglobin deficiency: A mechanism for loss of physiological activity in banked blood", PNAS, 104(43):17058-17062, (2007).

Rodrigues et al., "Correlation of the acid-sensitivity of polyethylene glycol daunorubicin conjugates with their in vitro antiproliferative activity", Bioorganic & Medicinal Chemistry, 14:4110-4117, (2006).

Salo et al., "Aminooxy Functionalized Oligonucleotides: Preparation, On-Support Derivatization, and Postsynthetic Attachment to Polymer Support", Bioconjugate Chem., 10:815-823, (1999).

Schneerson et al., "Preparation, characterization and immunogenicity of haemophilus influenzae type b polysaccharide-protein conjugates", Journal of Experimental Medicine, 152:361-376 (1980).

Skopp et al., "Fingerprinting of proteins cleaved in solution by cyanogen bromide", Appl. and Theoret. Electrophoresis, 1:61-64, (1989).

Skwarczynski et al., "Paclitaxel Prodrugs Toward Smarter Delivery of Anticancer Agents", Journal of Medicinal Chemistry, 49(25):7253-7269, (2006).

Stien et al., "Development and characterisation of novel human multidrug resistant mammary carcinoma lines in vitro and in vivo", Int. J. Cancer, 72:885-891, (1997).

Tomasik et al., "Chemical Modification of Starch", Advaces in Carbohydrate Chemistry and Biochemistry, 59:179-403, (2004).

Velasco et al., "Synthetic Peptides Representing T-Cell Epitopes Act as Carriers in Pneumococcal Polysaccharide Conjugate Vaccines", Infection and Immunity, 63(3):961-968, (1995).

Vasey et al., :Phase I Clinical and Pharmacokinetic Study of PKI [N-(2-Hydroxypropyl)methacrylamide Copolymer Doxorubicin]: First Member of a New Class of Chemotherapeutic Agents-Drug-Polymer Conjugates, Clinial Cancer Research, 5:83-94, (1999).

Abuchowski and Davis, "Soluble Polymer-Enzyme Adducts," Enzymes as drugs, 1981, Holcenberg and Rubberts (eds.), Chapter 13, pp. 367-383, John Wiley & Sons N.Y.

Adamczyk and Fishpaugh, "A Solid Supported Synthesis of Thiol Esters," Tetrahedron Lett., 1996, 37(25):4305-8.

Alayash and Cahson, "Hemoglobin and free radicals: implications for the development of a safe blood substitute," Molec. Med. Today, 1995, 1(3):122-7.

Aly et al., "Hemophilia A due to mutations that create new N-glycosylation sites," Proc. Natl. Acad. Sci., 1992, 89(11):4933-7.

Anderson and Meister, "Inhibition of γ-glutamyl transpeptidase and induction of glutathionuria by γ-glutamyl amino acids," Proc. Natl. Acad. Sci. USA, 1986, 83:5029-5032.

Andersson et al., "Isolation and characterization of human factor VIII: molecular forms in commercial factor VIII concentrate, cryoprecipitate, and plasma," Proc. Natl. Acad. Sci., 1986, 83(9):2979-83.

Anno et al, Sugar chemistry, 1995, p. 31.

Armitage, "Emerging applications of recombinant human granulocyte-macrophage colony-stimulating factor," Blood, 1998, 92(12):4491-4508.

Ashwell, "Carbohydrate Antigens: Coupling of Carbohydrates to Proteins by a Mixed Anhydride Reaction," Methods Enzymol., 1972, 28:219-22.

Avigad, "A simple spectrophotometric determination of formaldehyde and other aldehydes: application to periodate-oxidized glycol systems," Anal. Biochem., 1983, 134(2):499-504.

Axèn et al., "Chemical Coupling of Peptides and Proteins to Polysaccharides by Means of Cyanogen Halides," Nature, 1967, 214:1302-1304 (cited in 007001 OA response Sep. 2009).

Baldwin et al., "Synthesis of Polymer-Bound Hemoglobin Samples," Tetrahedron, 1981, 37:1723-1726.

Balland et al., "Characterisation of two differently processed forms of human recombinant factor IX synthesised in CHO cells transformed with a polycistronic vector," Eur. J. Biochem., 1988, 172(3):565-72.

Balland et al., "Intracellular distribution of ampicillin in murine macrophages infected with *Salmonella typhimurium* and treated with (3H)ampicillin-loaded nanoparticles," J. Antimicrob. Chemother., 1996, 37:105-115.

Barbone et al., "Reticulocyte measurements as a bioassay for erythropoietin," J. Pharm. Biomed. Anal., 1994, 12(4):515-522.

Bärström et al., "New derivatives of reducing oligosaccharides and their use in enzymatic reactions: efficient synthesis of sialyl Lewis a and sialyl dimeric Lewis x glycoconjugates," Carbohydr. Res., 2000, 328:525-531.

Bauer and Rosenberg, "Role of antithrombin III as a regulator of in vivo coagulation," Semin. Hematol., 1991, 28(1):10-18.

Bauer and Suresh, "S-[w-(Aminoöxy)alkyl]isothiuronium Salts, w,w'-Bis(aminoöxy)alkanes and Related Compounds," J. Org. Chem., 1963, 28:1604-1608.

Bauer et al., "Synthesis of w—(Aminooxy)alkanethiols," J. Org. Chem., 1965, 30:949-951.

Bayer et al., "The Avidin-Biotin Complex in Affinity Cytochemistry," Meth Enzymol, 1979, 62: 308-315.

Bendele et al., "Short Communication: Renal Tubular Vacuolation in Animals Treated with Polyethylene-Glycol-Conjugated Proteins," Toxicol. Sci., 1998, 42:152-157.

Benesch, "Bis(pyridoxal) Polyphosphates as Specific Intramolecular Cross-Linking Agents for Hemoglobin," Meth. Enzymol., 1994, 231:267-274.

Bepperling et al., "HES 130/0.4, a new HES specification: tissue storage after multiple infusions in rats," Crit. Care, 1999, 3(suppl 1):P153.

Berg et. al., "Engineering the proteolytic specificity of activated protein C improves its pharmacological properties," Proc. Natl. Acad. Sci., 2003, 100(8):4423-4428.

Berger et al., "Galactosyltransferase-dependent sialylation of complex and endo-N-acetylglucosaminidase H-treated core N-glycans in vitro," FEBS Lett., 1986, 203(1):64-68.

Bhattacharyya et al., "Recombinant Factor VIII for Haemophilia," CRIPS, 2003, 4(3):2-8.

Bjork and Danielsson, "Antithrombin and related inhibitors of coagulation proteinases," Proteinase Inhibitors, Barrett and Salvesen (eds.), 1986, Chapter 17, Amsterdam, The Netherlands, Elsevier Science Publishers (Biomedical Devision), pp. 489-513.

Black et al., "N-Bromoacetyl-glycopyranosylamines as affinity labels for β-glucosidase and a cellulase," Carbohydr. Res., 1993, 250:195-202.

Blum et al., "Improved silver staining of plant proteins, RNA and DNA in polyacrylamide gels," Electrophoresis, 1987, 8:93-99.

Bobbitt, "Periodate Oxidation of Carbohydrates," Carbohydr. Chem., 1956, 11:1-41.

Boissel et al., "Erythropoietin Structure-Function Relationships. Mutant proteins that test a model of tertiary structure," J. Biol. Chem., 1993, 268(21):15983-15993.

Boorsma et al., "Bioprocess applications of a Sindbis virus-based temperature-inducible expression system," Biotechnol. Bioeng., 2002, 79(6): 602-609.

Boturyn et al., "Synthesis of Fluorescent Probes for the Detection of Abasic Sites in DNA," Tetrahedron, 1997, 53(15):5485-5492.

Boyer et al., "Reaction in Biphasic Water/Organic Solvent System in the Presence of Surfactant: Inverse Phase Transfer Catalysis versus Interfacial Catalysis," Tetrahedron, 2000, 56:303-307.

Bowen et al., "Estimation of Effective and Total Erythropoiesis in Myelodysplasia Using Serum Transferrin Receptor and Erythropoietin Concentrations, with Automated Reticulocyte Parameters," Leukemia, 1994, 8(1):151-155.

Bronzino, The Biomedical Engineering Handbook, CRC Press, USA, Salem, 1995, (TOC only).

Bunn & Jandl, "The Renal Handling of Hemoglobin. II. Catabolism," J. Exp. Med., 1967, 129:925-934.
Burgess et al., "Stimulation by Human Placental Conditioned Medium of Hemopoietic Colony Formation by Human Marrow Cells," Blood, 1977, 49(4):573-583.
Bystrický et al., "Determination of the cross-linking effect of adipic acid dihydrazide on glycoconjugate preparation," Glycoconj. J., 1999, 16:691-695.
Cabacungan et al., "Amine Boranes as Alternative Reducing Agents for Reductive Alkylation of Proteins," Anal. Biochem., 1982, 124:272-278.
Carey, F.A. and Sundberg, R.J., "Organische Chemie", VCH Verlagsgesellschaft mbH, Weinheim (DE), 1995.
Carlsson et al., "Protein Thiolation and Reversible Protein-Protein Conjugation," Biochem J., 1978, 173:723-737.
Carrell et al., "Human alpha 1-antitrypsin: carbohydrate attachment and sequence homology," FEBS Letters, 1981, 135(2):301-3.
Carrell et al., "Structural mobility of antithrombin and its modulation by heparin," Thromb. Haemost., 1997, 78(1):516-9.
Carver et al., "Expression of human alpha 1 antitrypsin in transgenic sheep," Cytotechnology, 1992, 9(1-3):77-84.
Castillo et al., "Sensitive substrates for human leukocyte and porcine pancreatic elastase: a study of the merits of various chromophoric and fluorogenic leaving groups in assays for serine proteases," Anal. Biochem., 1979, 99(1):53-64.
Cebon et al., "Granulocyte-macrophage colony stimulating factor from human lymphocytes. The effect of glycosylation on receptor binding and biological activity," J. Biol. Chem., 1990, 265(8):4483-4491.
Cera et al., "Water-soluble polysaccharide-anthracycline conjugates: biological activity," Anti-Cancer Drug Design, 1992, 7(2):143-151.
Cerami, "Beyond Erythropoiesis: Novel Applications for Recombinant Human Erythropoietin," Semin. Hematol., 2001, 38:(3 Suppl 7):33-39.
Cerny et al., "A Hydroxyethyl Starch-Hemoglobin Polymer as a Blood Substitute," Clinical Hemorheology, 1982, 2(4):355-365.
Cervigni et al., "Synthesis of Glycopeptides and Lipopeptides by Chemoselective Ligation," Angewandte Chemie International Edition in English, 1996, 35(11):1230-1232.
Chagnon et al., "Murine renal cell carcinoma: evaluation of a dendritic-cell tumour vaccine," BJU Int., 2001, 88:418-424.
Chamow and Ashkenazi(eds.), "Antibody Fusion Proteins," 1999, 312 pages, John Wiley & Sons, Inc., (TOC).
Chamow et al., "Conjugation of Soluble CD4 without Loss of Biological Activity via a Novel Carbohydrate-directed Cross-linking Reagent," J. Biol. Chem., 1992, 267(22):15916-15922.
Chan et al., "Preparation of O-esters from the corresponding thiol esters: tert-butyl cyclohexanecarboxylate," Organic Syntheses, Coll., 1990, 7:87-93.
Chang, "Blood Substitutes Based on Modified Hemoglobin Prepared by Encapsulation or Crosslinking: An Overview," Biomat., Art. Cells & Immob. Biotech., 1992, 20:159-179.
Chaplin and Kennedy (eds.), 1996, Carbohydrate Analysis: a practical approach, expecially chapter 5 Montreuill, Glycoproteins, pp. 175-177; IRL Press Practical approach series.
Chaplin and Kennedy (eds.), Carbohydrate Analysis: a practical approach, 1994, 2nd Edition, Chapter 1 "Monosaccharides" pp. 1-41, Chapter 2 "Oligosaccharides" pp. 42-72, Chapter 3 "Neutral Polysaccharides" pp. 73-124, Chapter 5 "Glycoproteins" pp. 181-293, IRL Press.
Chaplin, "A Rapid and Sensitive Method for the Analysis of Carbohydrate Components in Glycoproteins Using Gas-Liquid Chromatography," Anal. Biochem., 1982, 123:336-341.
Chaplin, "Monosaccharides," Carbohydrate analysis: a practical approach, 1996, Chaplin and Kennedy (eds.), Chapter 1, "Oligosaccharides," pp. 37-54.
Chapman et al., "Therapeutic antibody fragments with prolonged in vivo half-lives," Nature Biotech., 1999, 17:780-783.
Chen et al., "Purification of alpha 1 proteinase inhibitor from human plasma fraction IV-1 by ion exchange chromatography," VoxSanguinis, 1998, 74(4):232-241.
Choay et al., "Structural studies on a biologically active hexasaccharide obtained from heparin," Ann. NY Acad. Sci., 1981, 370:644-9.
Choay et al., "Structure-activity relationship in heparin: a synthetic pentasaccharide with high affinity for antithrombin III and eliciting high anti-factor Xa activity," Biochem. Biophys. Res. Commun., 1983, 116(2):492-9.
Chow et al., "In vitro Induction of apoptosis of neoplastic cells in low-grade non-Hodgkin's lymphomas using combinations of established cytotoxic drugs with bendamustine," Haematologica, 2001, 86:485-493.
Chu et al., "Further Studies on the Immunogenicity of Haemophilus influenzae Type b and Pneumococcal Type 6A Polysaccharide-Protein Conjugates," Infect. Immun., 1983, 40:245-256.
Colman, "Production of therapeutic proteins in the milk of transgenic livestock," Biochem. Soc. Symp., 1998, 63:141-147.
Conradt et al., "Expression of human interleukin-2 in recombinant baby hamster kidney, Ltk-, and Chinese hamster ovary cells. Structure of O-linked carbohydrate chains and their location within the polypeptide," J. Biol. Chem., 1989, 264:17368-17373.
Corey and Clark, "A New Method for the Synthesis of 2-Pyridinethiol Carboxylic Esters," Tetrahedron Lett., 1979, 2875-8.
Cumber et al., "Preparation of Antibody-Toxin Conjugates," Meth. Enzymol., 1985, 112:207-225.
Davis and Flitsch, "A Novel Method for the Specific Glycosylation of Proteins," Tetrahedron Lett., 1991, 32(46):6793-6.
De Koning et al., "An approach to the synthesis of peptide-PNA-peptide conjugates via native ligation," Tetrahedron Letters, 2002, 43(45):8173-8176.
De Velasco et al., "Synthetic Peptides Representing T-Cell Epitopes Act as Carriers in Pneumococcal Polysaccharide Conjugate Vaccines," Infect. Immun., 1995, 36(3):961-968.
Delgado et al., "The Uses and Properties of PEG-Linked Proteins," Crit. Rev. Ther. Drug Carrier Syst., 1992, 9(3,4):249-304.
Delorme et al., "Role of Glycosylation on the Secretion and Biological Activity of Erythropoietin," Biochemistry, 1992, 31(41):9871-9876.
Denzlinger et al., "Differential activation of the endogenous leukotriene biosynthesis by two different preparations of Granulocyte-Macrophage Colony-Stimulating Factor in healthy volunteers," Blood, 1993, 81(8):2007-2013.
Dictionary of Chemistry and Chemical Technology, 2003, p. 769 (English translation provided).
Dieterich et al., "Hydroxyethyl Starch Antibodies in Humans: Incidence and Clinical Relevance," Anesth. Analg., 1998, 86:1123-1126.
Dittmar et al., "Human Glycoproteins and Derived Variants from Recombinant Mammalian Cell Lines," Advances in Protein Design, 1989, 12:145-156.
Donahue et al., "Effects of N-linked carbohydrates on the in vivo properties of human GM-CSF," Cold Spring Harbor Symp. Quant. Biol., 1986, 51, pp. 685-692.
Dorner et al., "Increased Synthesis of Secreted Proteins Induces Expression of Glucose-regulated Proteins in Butyrate-treated Chinese Hamster Ovary Cells," J. Biol. Chem., 1989, 264(34):20602-20607.
Dowling and Russell, "Pharmacokinetics of a long-acting oxytetracycline-polyethylene glycol formulation in horses," J. Vet. Pharmacol. Therap., 2000, 23:107-110.
Dreborg and Åkerblom, "Immunotherapy with Monomethoxypolyethylene Glycol Modified Allergens," Crit. Rev. Ther. Drug Carrier Syst., 1990, 6(4):315-365.
Edmunds et al., "Transgenically Produced Human Antithrombin: Structural and Functional Comparison to Human Plasma-Derived Antithrombin," Blood, 1998, 91, 12:4561-4671.
Elliott et al., "Mapping of the Active Site of Recombinant Human Erythropoietin," Blood, 1997, 89(2): 493-502.
European Pharmacopeia 2001, 911-917.
European Pharmacopoeia, 1996, Erythropoietin concentrated solution, Pharmaeuropa., 8, 371-377.
Ernst B., G.W. Hart and P.Sinay eds., Carbohydrates in Chemistry and Biology part I, vols. 1+2, Published 2000, Whiley-VCH Weinheim—New York—Chichester—Brisbane—Toronto, ISBN 3-52729511-9.

European Pharmacopoeia, "Erythropoietin Concentrated Solution," 3rd Edition, 2000, Monography, pp. 655-660.

European Pharmacopoeia, "Erythropoietin Concentrated Solution," 4th Edition, 2002, Monography, pp. 1123-1128.

Fernández-Santana et al., "Conjugation of 5-azido-3-oxapentyl glycosides with thiolated proteins through the use of thiophilic derivatives," Glycoconj. J., 1998, 15:549-553.

Fibi et al., "Evidence for the Location of the Receptor-Binding Site of Human Erythropoietin at the Carboxyl-Terminal Domain," Blood, 1991, 77(6):1203-1210.

Fibi et al., "N- and O-Glycosylation Muteins of Recombinant Human Erythropoietin Secreted From BHK-21 Cells," Blood, 1995, 85(5):1229-1236.

Fissekis et al., "N-Pantyol-(substituted)amines, Pantothenic Acid Analogues," J. Med. Pharm. Chem., 1960, 2:47-56.

Franzen et al., "Structural studies on the carbohydrate portion of human antithrombin III," J. Biol. Chem., 1980, 255(11):5090-3.

Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.

Fujiki et al., "Studies on the disulfide bonds in human pituitary follicle-stimulating hormone." Biochim. Biophys. Acta, 1980, 624:428-435.

Gaertner and Offord, "Site-Specific Attachment of Functionalized Poly(ethylene glycol) to the Amino Terminus of Proteins," Bioconjugate Chemistry, 1996, 7(1):38-44.

Gervais et al., "NMR investigations of the role of the sugar moiety in glycosylated recombinant human granulocyte-colony-stimulating factor," Eur. J. Biochem., 1997, 247:386-395.

Gillis et al., "T Cell Growth Factor: Parameters of Production and a Quantitative Microassay for Activity," J. Immunol., 1978, 120(6):2027-2032.

Goldstein and Gelb, "An alternate preparation of thioester resin linkers for solid-phase synthesis of peptide C-terminal thioacids," Tetrahedron Lett., 2000, 41(16):2797-2800.

Gonzales, Lio and Thiem, "Chemoenzymatic synthesis of spacer-linked oligosaccharides for the preparation of neoglycoproteins," Carbohydr. Res., 1999, 317:180-190.

Goronzy et al., "T-Cell Derived Lymphokines as Regulators of Chronic Inflammation: Potential Targets for Immunomodulation," Am. J. Therap., 1996, 3(2):109-114.

Gould et al., "The Development of Hemoglobin Solutions as Red Cell Substitutes: Hemoglobin Solutions," Transfus. Sci., 1995, 16:5-17.

Grabenhorst and Conradt, "The Cytoplasmic, Transmembrane, and Stem Regions of Glycosyltransferases Specify Their in vivo Functional Sublocalization and Stability in the Golgi," J. Biol. Chem., 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," Eur. J. Biochem., 1993, 215:189-197.

Grabenhorst et al., "Construction of stable BHK-21 cells coexpressing human secretory glycoproteins and human Gal(β1-4)GlcNAc-R α2,6-sialyltransferase: α2,6-Linked NeuAc is preferentially attached to the Gal(β1-4)GlcNAc(β1-2)Man(α1-3)-branch of diantennary oligosaccharides from secreted recombinant β-trace protein," Eur. J. Biochem., 1995, 232:718-725.

Grabenhorst et al., "Genetic engineering of recombinant glycoproteins and the glycosylation pathway in mammalian host cells," Glycoconj J., 1999, 16(2):81-97.

Grabenhorst et al., "In Vivo Specificity of Human α1,3/4-Fucosyltransferases III-VII in the Biosynthesis of Lewisx and Sialyl Lewisx Motifs on Complex-type N-Glycans. Coexpression studies from BHK-21 cells together with human β-trace protein," J. Biol. Chem., 1998, 273(47):30985-30994.

Figure 2:
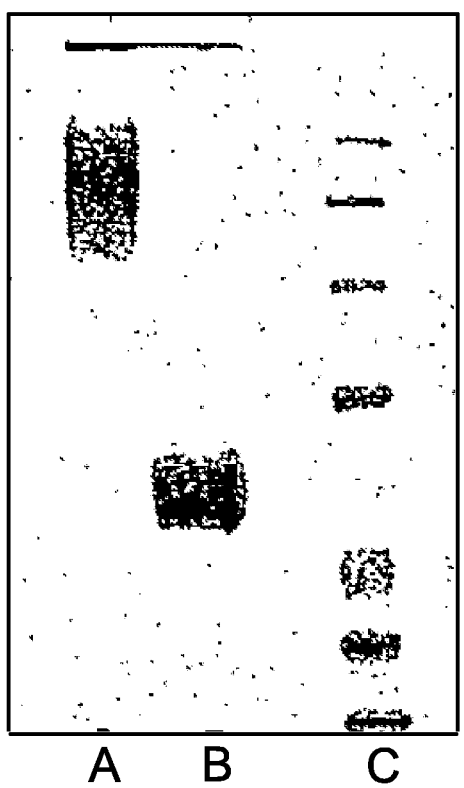

Gray, "The Direct Coupling of Oligosaccharides to Proteins and Derivatized Gels," Arch. Biochem. Biophys., 1974, 163:426-428 (Fig. 2.1a).

Greenfield et al., "Evaluation in Vitro of Adriamycin Immunoconjugates Synthesized Using an Acid-sensitive Hydrazone Linker," Cancer Research, 1990, 50:6600-6607.

Gribben et al., "Development of antibodies to unprotected glycosylation sites on recombinant GM-CSF," Lancet, 1990, 335:434-437.

Grimmecke and Brade, "Studies on the reductive amination of 3-deoxy-D-manno-octulosonic acid (Kdo)," Glycoconj. J., 1998, 15:555-562.

Guillaumie et al., "Immobilization of pectin fragments on solid supports: Novel coupling by thiazolidine formation," Bioconjugate Chem., 2002, 13:285-294.

Habeeb, "Determination of Free Amino Groups in Proteins by Trinitrobenzenesulfonic Acid," Anal. Biochem., 1966, 14:328-336.

Hai et al., "Diaspirin Crosslinked Hemoglobin (DCLHbTM) Polymerization," Art. Cells, Blood Subs., and Immob Biotech., 1994, 22(3):923-931.

Hallaway et al., "Modulation of Deferoxamine Toxicity and Clearance by Covalent Attachment to Biocompatible Polymers," Proc. Natl. Acad. Sci. USA, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," Bioconj. Chem., 2003, 14:320-330.

Harris et al., "Pegylation. A novel process for modifying pharmacokinetics," Clin. Pharmacokinet, 2001, 40(7): 539-551.

Hartman and Wold, "Cross-Linking of Bovine Pancreative Ribonuclease A with Dimethyl Adipimidate," Biochemistry, 1967, 6(8):2439-2448.

Hashimoto et al., "Chemical Modification of the Reducing Chain End in Dextrans and Trimethylsilylation of Its Hydroxyl Groups," J. Polymer Science: Part A: Polymer Chemistry, 1991, 29:1271-1279.

Hattori et al., "Reduced Immunogenicity of β-Lactoglobulin by Conjugation with Carboxymethyl Dextran," Bioconjug. Chem., 2000, 11:84-93.

He et al., "A simplified system for generating recombinant adenoviruses," Proc. Natl. Acad. Sci. USA, 1998, 95(5):2509-2514.

Heindel, Ned D. et al., "Hydrazide Pharmaceuticals as Conjugates to Polyaldehyde Dextran" 1990, Bioconjugate Chem. 1, 77-82.

Heitzmann and Richards, "Use of the Avidin-Biotin Complex for Specific Staining of Biological Membranes in Electron Microscopy," Proc Natl Acad Sci USA, 1974, 71(9):3537-3561.

Herman et al., "Characterization, Formulation, and Stability of Neupogen® (Filgrastim), a Recombinant Human Granulocyte-Colony Stimulating Factor," Formulation, Characterization, and Stability of Protein Drugs, Pearlman and Wang (eds.), Plenum Press, Chapter 7, 1996, pp. 303-328.

Hermanson, Bioconjugate Techniques, 1996 (TOC only).

Hermentin et al., "A Strategy for the Mapping of N-Glycans by High-pH Anion-Exchange Chromatography with Pulsed Amperometric Detection," Anal. Biochem., 1992, 203(2):281-289.

Higuchi et al., "Role of Sugar Chains in the Expression of the Biological Activity of Human Erythropoietin," J. Biol. Chem., 1992, 267(11):7703-7709.

Hodges and Chan, "Locations of oligosaccharide chains in human alpha 1-protease inhibitor and oligosaccharide structures at each site," Biochemistry, 1982, 21(11):2805-10.

Hodges et al., "Structure of the oligosaccharide chains in human alpha 1-protease inhibitor," J. Biol. Chem., 1979, 254(17):8208-12.

Hovgaard et al., "Clinical pharmacokinetic studies of a human haemopoietic growth factor, GM-CSF," Eur. J. Clin. Inv., 1992, 22:45-49.

Hovinen et al., "Ethyl[2-deoxy-5-0-(4,4'-dimethoxytrityl)-α-and β-D-erythro-pentofuranosyl] acetates as versatile intermediates in nucleic acid chemistry," Nucleosides Nucleotides, 1999, 18:1263-1264.

Iakovenko et al., "Semi-synthetic Rab proteins as tools for studying intermolecular interactions," FEBS Letters, 2000, 468:155-158.

Ingenito et al., "Solid Phase Synthesis of Peptide C-Terminal Thioesters by Fmoc/t-Bu Chemistry," J. Am. Chem. Soc., 1999, 121:11369-11374.

Inoue et al., "An Improved Method for the Purification of Human Erythropoietin with High in Vivo Activity from the Urine of Anemic Patients," Biol. Pharm. Bull., 1994, 17(2):180-184.

Iwamoto et al., "Polysaccharide-Coated Oil Droplets in Oil-in-Water Emulsions as Targetable Carriers for Lipophilic Drugs," J. Pharm. Sci., 1991, 80(3):219-224.

Jaques et al., "N.M.R. spectroscopy and calcium binding of sialic acids: N-glycolylneuraminic acid and periodate-oxidized N-acetylneuraminic acid," Carb. Res., 1980, 83:21-32.

Jia et al., "S-nitrosohaemoglobin: a dynamic activity of blood involved in vascular control," Nature, 1996, 380:221-226.

Jones et al., "Multivalent poly (ethylene glycol)-containing conjugates for in vivo antibody suppression" Bioconjugate Chemistry, 2003, 14(6):1067-1076.

Jones et al., "A convenient synthesis of N-(tert-butyloxycarbonyl)aminooxy ethers," Tetrahedron Letters, 2000, 41(10):1531-1533.

Kallin, "Coupling of Oligosaccharides to Proteins Using p-Trifluoroacetamidoaniline," Meth. Enzymol., 1994, 242:119-123.

Karpusas et al., "Commercial preparations of interferon beta are Betaseron (IFN beta 1b), Avonex and Rebif (IFN beta 1a)," Proc. Natl. Acad. Sci. USA, 1997, 94:11813-11818.

Kaufman et al., "Synthesis, processing, and secretion of recombinant human factor VIII expressed in mammalian cells," J. Biol. Chem., 1988, 263(13):6352-62.

Kaushansky et al., "Role of carbohydrate in the function of human Granulocyte-Macrophage Colony-Stimulating Factor," Biochemistry, 1987, 26:4861-4867.

Keaney, Jr. et al., "NO Forms an Adduct with Serum Albumin that Has Endothelium-derived Relaxing Factor-like Properties," J. Clin. Invest., 1993, 91:1582-1589.

Keene et al., "Expression of biologically active human follitropin in Chinese hamster ovary cells," J. Biol. Chem., 1989, 264:4769-4775.

Keipert et al., "Functional properties of a new crosslinked hemoglobin designed for use as a red cell substitute," Transfusion, 1989, 29:768-773.

Kitamura et al., "Chemical Engineering of the Monoclonal Antibody A7 by Polyethylene Glycol for Targeting Cancer Chemotherapy," Cancer Res., 1991, 51:4310-4315.

Kitamura et al., "Establishment and Characterization of a Unique Human Cell Line That Proliferates Dependently on GM-CSF, IL-3, or Erythropoietin," J. Cell. Phys., 1989, 140:323-334.

Kleine-Tebbe et al., "Allergen Immunotherapy—A Position Paper of the German Society for Allergology and Clinical Immunology," Pneumologie, 2001, 55:438-444 (w/English summary).

Klemm et al., "Esterification of Cellulose," Comprehensive Cellulose Chemistry, 1998, vol. 2, Wiley-VCH, Weinheim, New York, especially chapter 4.4, pp. 99-207.

Klimek et al., "Specific Immunotherapy (Hyposensibilisation)," Allergologie and Umweltmedizin, Chapter 15, pp. 157-195.

Kobayashi et al., "Reduced Immunogenicity of β-Lactoglobulin by Conjugation with Carboxymethyl Dextra Differing in Molecular Weight," J. Agric. Food Chem., 2001, 49(2):823-831.

Kochendoerfer et al., "Design and chemical synthesis of a homogeneous polymer-modified erythropoiesis protein," Science, 2003, 299(5608):884-887.

Kojima et al., "Mitomycin C-dextran conjugate: a novel high molecular weight pro-drug of mitomycin C," J. Pharm. Pharmacol., 1980, 32:30-34.

Komatsu et al., "Cloning of granulocyte colony-stimulating factor cDNA from human macrophages and its expression in *Escherichia coli*," Jpn. J. Cancer Res., 1987, 78(11):1179-1181.

Kraehenbuhl et al, "Preparation and Characterization of an Immuno Electron Microscope Tracer consisting of a Heme Octa Peptide coupled to FAB," J. Exp. Med., 1974, 139(1):208-223.

Krantz, "Erythropoietin," Blood, 1991, 77(3):419-434.

Krystal et al., "Purification of Human Erythropoietin to Homogeneity by a Rapid Five-Step Procedure," Blood, 1986, 67(1):71-79.

Krystal, "A Simple Microassay for Erythropoietin Based on 3H-Thymidine Incorporation into Spleen Cells from Phenylhydrazine Treated Mice," Exp. Hematol., 1983, 11(7):649-660.

Krystal, "Physical and Biological Characterization of Erythroblast Enhancing Factor (EEF), a Late Acting Erythropoietic Stimulator in Serum Distinct from Erythropoietin," Exp. Hematol., 1983, 11(1):18-31.

Kuberan et al., "Preparation and isolation of neoglycoconjugates using biotin-streptavidin complexes," Glycoconj. J., 1999, 16:271-281.

Kurtz and Eckardt, "Assays for Erythropoietin," Nephron., 1989, 51(suppl 1):11-14 (w/English summary).

Lahiri et al., "Antithrombin-heparin cofactor: an inhibitor of plasma kallikrein," Arch. Biochem. Biophys., 1976, 175:737-47.

Lapthorn et al., "Crystal structure of human chorionic gonadotropin," Nature, 1994, 369:455-461.

Larionova et al., "Conjugation of the Bowman-Birk Soybean Proteinase Inhibitor with Hydroxyethylstarch," Appl. Biochem. Biotech., 1997, 62:175-182.

Lee (ed.), "Synthesis of Peptides and Proteins," Peptide and Protein Drug Delivery, 1991, p. 65.

Lee and Lee, "Neoglycoproteins," Glycoproteins II, 1997, Chapter 17, Elsevier Science B.V., pp. 601-620.

Lee et al. "Conjugation of trypsin by temperature-sensitve polymers containing a carbohydrate moiety: thermal modulation of enzyme activity," Biotechnol. Prog., 1998, 14(3):508-516.

Leenders et al., "β-Glucuronyl Carbamate Based Pro-moieties Designed for Prodrugs in ADEPT," Tetrahedron Letters, 1995, 36(10):1701-1704.

Lees et al., "Activation of soluble polysaccharides with 1-cyano-4-dimethylaminopyridinium tetrafluoroborate for use in protein-polysaccharide conjugate vaccines and immunological reagents," Vaccine, 1996, 14(3):190-198.

Lesnefsky et al., "High-Dose Iron-Chelator Therapy During Reperfusion with Deferoxamine-Hydroxyethyl Starch Conjugate Fails to Reduce Canine Infarct Size," J. Cardiovasc. Pharmacol., 1990, 16(4):523-528.

Lewis et al., "The phase transfer catalysed synthesis of isoflavone-O-glucosides," J. Chem. Soc., Perkins Trans. 1, 1998, pp. 2481-2484.

Lewis and Wähälä, "Regiospecific 4'-O-β-glucosidation of isoflavones," Tetrahedron Letters, 1998, 39(51):9559-9562.

Levy et al., "Recombinant Antithrombin: Production and Role in Cardiovascular Disorder," Sem. Thromb. Hem., 2001, 27(4):405-416.

Li et al., "Direct preparation of peptide thioesters using an Fmoc solid-phase method," Tetrahedron Lett., 1998, 39(47):8669-8672.

Lin et al., "L-Cysteine as a water-soluble cation scavenger in the removal of the 2,4,6-trimethoxybenzyl group from thiols," Tetrahedron Lett., 2002, 43:4531-4533.

Lin et al., "Cloning and expression of the human erythropoietin gene," Proc. Natl. Acad. Sci. USA, 1985, 82:7580-7584.

Lindsey at al., "Porphyrin Building Blocks for Modular Construction of Bioorganic Model Systems," Tetrahedron, 1994, 50(30):8941-8968, especially p. 8956.

Liu et al., "Characterization of the structural and functional changes of hemoglobin in dimethyl sulfoxide by spectroscopic techniques," Biochim. Biophys. Acta, 1998, 138:53-60.

Lomant and Fairbanks, "Chemical Probes of Extended Biological Structures: Synthesis and Properties of the Cleavable Protein Cross-linking Reagent [35 S]Dithiobis(succinimidyl propionate)," J. Mol. Biol., 1976, 104:243-261.

Lönngren and Goldstein, "Coupling of Aldobionic Acids to Proteins Using Water-Soluble Carbodiimide," Meth. Enzymol., 1994, 242:116-118.

Lund et al., Nucl Acids Res., 1988, 16:10861-10880.

Manger et al., "1-N-Glycyl β-Oligosaccharide Derivatives as Stable Intermediates for the Formation of Glycoconjugate Probes," Biochemistry, 1992, 31:10724-10732.

Manger et al., "Synthesis of 1-N-Glycyl β-Oligosaccharide Derivatives. Reactivity of *Lens culinaris* Lectin with a Fluorescent Labeled Streptavidin Pseudoglycoprotein and Immobilized Neoglycolipid," Biochemistry, 1992, 31:10733-10740.

Maout et al., "Hydroxyethylstarch Conjugated to Human Hemoglobin for use in Blood Transfusion: Comparison with Dextran Conjugates," Carbohydrates and Carbohydrate Polymers—Analysis, Biotechnology, Modification, Antiviral and Other Applications, 1993, Chapter 12, pp. 132-140.

March, J., Advanced Organic Chemistry, 4th edition, John Wiley and Sons, New York (1992) 409.

Masamune et al., "A General, Selective Synthesis of Thiol Esters," Can. J. Chem., 1975, 53:3693-5.

Masamune et al., "Tylonolide hemiacetal, the aglycone of tylosin, and its partial synthesis," J. Am. Chem. Soc., 1976, 98(24):7874-5.

Masuda et al., "Synthesis and anti-influenza evaluation of orally active bicyclic ether derivatives related to zanamivir," Bioorganic & Medicinal Chemistry Letters, 2003, 13(4):669-673.

McMahon et al., "Pharmacokinetics and Effects of Recombinant Human Erythropoietin After Intravenous and Subcutaneous Injections in Healthy Volunteers," Blood, 1990, 76(9):1718-1722.

Mega et al., "Studies on the oligosaccharide chains of human alpha 1-protease inhibitor. I. Isolation of glycopeptides," J. Biol. Chem., 1980, 255(9):4053-6.

Mega et al., "Studies on the Oligosaccharide Chains of Human α1-Protease Inhibitor. II. Structure of oligosaccharides," J. Biol. Chem., 1980, 255(9):4057-4061.

Meinjohanns et al., "Novel sequential solid-phase synthesis of N-linked glycopeptides from natural sources," J. Chem. Soc., Perkin Trans. 1, 1998, 1:549-560.

Menache et al., "Antithrombin III: physiology, deficiency, and replacement therapy," Transfusion, 1992, 32(6):580-8.

Menache, "Antithrombin III: introduction," Semin. Hematol., 1991, 28(1):1-2.

Merck Index 2006, Definition of Dimethyl Sulfoxide, Merck & Co., 14th Edition, accessed online: http//themerckindex.cambridgesoft.com/themerckindex/index.asp on Sep. 4, 2007.

Mikola and Hanninen, "Introduction of Aliphatic Amino and Hydroxy Groups to Keto Steroids Using O-Substituted Hydroxylamines," Bioconj. Chem., 1992, 3(2):182-186.

Ming et al., "Interleukin 6 is the principal cytolytic T lymphocyte differentiation factor for thymocytes in human leukocyte conditioned medium," J. Mol. Cell. Immunol., 1989, 4:203-211.

Minnema et al., "Recombinant human antithrombin III improves survival and attenuates inflammatory responses in baboons lethally challenged with *Escherichia coli*," Blood, 2000, 95(4): 1117-1123.

Miyake et al., "Purification of Human Erythropoietin," J. Biol. Chem., 1977, 252(15):5558-5564.

Montreuil et al., "Hexuronic acids," Carbohydrate analysis: a practical approach, 1996, Chaplin and Kennedy (eds.), Chapter 5, pp. 175-204.

Moonen et al., "Increased biological activity of deglycosylated recombinant human granulocyte-macrophage colony-stimulating factor produced by yeast or animal cells," Proc. Natl. Acad. Sci. USA, 1987, 84(13):4428-4431.

Mori et.al., "The activation of type 1 and type 2 plasminogen by type I and type II tissue plasminogen activator," J. Biol. Chem., 1995, 270(7):3261-3267.

Mosbech et al., "Hyposensitization in asthmatics with mPEG-modified and unmodified house dust mite extract," Allergy, 1990, 45(2):130-141.

Mosmann, "Rapid Colorimetric Assay for Cellular Growth and Survival: Application to Proliferation and Cytotoxicity Assays," J. Immunol. Meth., 1983, 65:55-63.

Mueller et al., "Recombinant Glycoprotein Product Quality in Proliferation-Controlled BHK-21 Cells," Biotechnol. Bioeng., 1999, 65(5):529-536.

Muir et al., "Expressed protein ligation: a general method for protein engineering," Proc. Natl. Acad. Sci. USA, 1998, 95(12):6705-6710.

Mukaiyama et al., "Peptide Synthesis via Oxidation-Reduction Condensation by the Use of Non-metallic Compound as a Mercaptan Scavenger," Bull. Chem. Soc. Jpn., 1970, 43:1271.

Mumberg et al., "Regulatable promoters of *Saccharomyces cerevisiae*: comparison of transcriptional activity and their use for heterologous expression," Nucl. Acids Res., 1994, 22(25):5767-5768.

Murano et al., "Some properties of antithrombin-III and its concentration in human plasma," Thromb. Res., 1980, 18(1-2):259-62.

Nagata et al., "Molecular cloning and expression of cDNA for human granulocyte colony-stimulating factor," Nature, 1986, 319:415-418.

Nagata et al., "The chromosomal gene structure and two mRNAs for human granulocyte colony-stimulating factor," EMBO J., 1986, 5(3):575-581.

Nakane et al., "The Accumulation Mechanism of Cationic Mitomycin C-dextran Conjugates in the Liver: In-vivo Cellular Localization and In-vitro Interaction with Hepatocytes," J. Pharm. Pharmacol., 1988, 40:1-6.

Nedospasov and Khomutov, "Synthesis and some properties of aminooxyalkylcelluloses," Bulletin of the Academy of Sciences of the USSR, 1976, Division of Chemical Science, Consultants Bureau, New York, 25:1105-1110.

Nimtz et al., "Carbohydrate structures of a human tissue plasminogen activator variant expressed in recombinant Chinese hamster ovary cells," FEBS Lett., 1990, 271:14-18.

Nimtz et al., "Structural characterization of the oligosaccharide chains of native and crystallized boar seminal plasma spermadhesin PSP-I and PSP-II glycoforms," Eur. J. Biochem., 1999, 265:703-718.

Nimtz et al., "Structures of sialylated oligosaccharides of human erythropoietin expressed in recombinant BHK-21 cells," Eur. J. Biochem., 1993, 213:39-56.

Nohynek et al., "Comparison of the potency of glycosylated and nonglycosylated recombinant human granulocyte colony-stimulating factors in neutropenic and nonneutropenic CD rats," Cancer Chemother Pharmacol., 1997, 39:259-266.

Nomura et al., "Pharmacokinetic characteristics and therapeutic effects of mitomycin C-dextran conjugates after intratumoural injection," J. Controlled Release, 1998, 52:239-252.

O'Shannessy and Wilchek, "Immobilization of Glycoconjugates by Their Oligosaccharides: Use of Hydrazido-Derivatized Matrices," Analytical Biochemistry, 1990, 191:1.

Ohta et al., "Usefulness of Glycopeptide Mapping by Liquid Chromatography/Mass Spectrometry in Comparability Assessment of Glycoprotein Products," Biologicals, 2002, 30(3):235-244.

Okamoto et al., "Purification and characterization of three forms of differently glycosylated recombinant human Granulocyte-Macrophage Colony-Stimulating Factor," Arch. Biochem. Biophys., 1991, 286(2):562-568.

Okamoto et al., "A facile incorporation of the aldehyde function into DNA: 3-formylindole nucleoside as an aldehyde-containing universal nucleoside," Tetrahedron Lett., 2002, 43:4581-4583.

Olson and Bjork, "Predominant contribution of surface approximation to the mechanism of heparin acceleration of the antithrombin-thrombin reaction. Elucidation from salt concentration effects," J. Biol. Chem., 1991, 266(10):6353-64.

Olson et al., "Role of the antithrombin-binding pentasaccharide in heparin acceleration of antithrombin-proteinase reactions. Resolution of the antithrombin conformational change contribution to heparin rate enhancement," J. Biol. Chem., 1992, 267(18):12528-38.

Opal et al., "Antithrombin, heparin, and heparan sulfate," Crit. Care Med., 2002, 30(5):S325-S331.

Organikum, Organisch-chemisches Grundpraktikum, 1984, VEB Deutscher Verlag der Wissenschaften, p. 472 (with verified English translation).

Pawlowski et al., "A new method of non-cross-linking conjugates of polysaccharides to protein via thioether bonds for the preparation of saccharide-protein conjugate vaccines," Vaccine, 1999, 17:1474-1483.

Pazur, "Neutral polysaccharides," Carbohydrate analysis: a practical approach, 1996, Chaplin and Kennedy (eds.), Chapter 3, pp. 55-96.

Pedley et al., "The potential for enhanced tumour localization by poly)ethylene glycol) modification of anti-CEA antibody," Br. J. Cancer, 1994, 70:1126-1130.

Peeters et al., "Comparison of four bifunctional reagents for coupling peptides to proteins and the effect of the three moieties on the immunogenicity of the conjugates," J. Immunol. Meth., 1989, 120:133-143.

Pelter et al., "Synthesis of Thioesters by Reactions of Carboxylic Acids with Tris-(ethylthio)borane," J. Am. Chem. Soc., Perkin Trans I, 1977, 1672-674.

Peri, F. et al, "Chemo- and Stereoselective Glycosylation of Hydroxylamino Derivatives: A Versatile Approach to Glycoconjugates", 1998, Tetrahedron 54, 12269-12278.

Peron et al., "Hydroxyethyl starch-induced renal insufficiency after plasma exchange in a patient with polymyositis and liver cirrhosis," Clin. Nephrol., 2001, 55(5):408-411.

Peterson, The Physiological Inhibitions of Blood Coagulation and Fibrinolysis, Elsevier/ North-Holland Biomedical Press 1979, p. 43. Pharma Business, Jul./Aug. 2000, pp. 45-60.

Pierce Chemical Technical Library, "cross-linking," 1994, 45 pages.

Pike et al., "Heparin-dependent Modification of the Reactive Center Arginine of Antithrombin and Consequent Increase in Heparin Binding Affinity," J. Biol. Chem., 1997, 272_32:19652-19655.

Quelle et al., "High-Level Expression and Purification of a Recombinant Human Erythropoietin Produced Using a Baculovirus Vector," Blood, 1989, 74(2):652-657.

Rabiner et al., "Evaluation of a stroma-free hemoglobin solution for use as a plasma expander," J. Exp. Med., 1967, 126:1127-1142.

Radomsky and Temeriusz, "Thiazolidine-4(R)-carboxylic acids derived from sugars: part I, C-2-epimerisation in aqueous solutions," Carb. Res., 1989, 187:223-237.

Ragnhammar et al., "Induction of anti-recombinant human Granulocyte-Macrophage Colony-Stimulating Factor (*Escherichia coli*-derived) antibodies and clinical effects in nonimmunocompromised patients," Blood, 1994, 84:4078-4087.

Ragupathi et al., "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm," Glycoconj. J., 1998, 15:217-221.

Ramos et al., "Enzymatic Synthesis of Neoglycopeptide Building Blocks," Angew. Chem. Int. Ed., 2000, 39(2):396-398.

Rapoport et al., "Protein transport across the eukaryotic endoplasmic reticulum and bacterial inner membranes," Annu Rev Biochem., 1996, 65:271-303.

Reddy et al., "Use of peginterferon alfa-2a (40 KD) (Pegasys) for the treatment of hepatitis C," Advanced Drug Delivery Reviews, 2002, 54:571-586.

Reidhaar-Olson et al., "Identification of Residues Critical to the Activity of Human Granulocyte Colony-Stimulating Factor," Biochemistry, 1996, 35:9034-9041.

Reischl (ed)., Molecular Diagnosis of Infectious Diseases, 1997, vol. 13, Totowa NJ, Humana Press Inc. (TOC Only).

Relihan et al., "Clearance Rate and Effect on Renal Function of Stroma-Free Hemoglobin Following Renal Ischemia," Ann. Surg., 1972, 176(6):700-704.

Revoltella et al., "Natural and therapy-induced anti-GM-CSF and anti-G-CSF antibodies in human serum," Leukemia and Lymphoma, 1997, 26:29-34.

Richter and de Belder, "Antibodies against Hydroxyethylstarch Produced in Rabbits by Immunization with a Protein-Hydroxyethylstarch Conjugate," Int. Arch. Allergy Appl. Immun., 1976, 52:307-314.

Roemisch et al., "Antithrombin: a new look at the actions of a serine protease inhibitor," Blood Coagul Fibrinolysism, 2002, 13(8):657-70.

Rogers et al., "Effects of polymerization on the oxygen carrying and redox properties of diaspirin cross-linked hemoglobin," Biochim. Biophys. Acta, 1995, 1248:135-142.

Rohrling et al., "Synthesis and testing of a novel fluorescene label for carbonyls in carbohydrates and cellulosics," Synlett, 2001, 5:682-684.

Rose, "Facile Synthesis of Homogeneous Artificial Proteins," J. Am. Chem. Soc., 1994, 116:30-33.

Rosenberg et al., "Antithrombin-III," Rev. Hematol., 1986, 2:351-416.

Rosenberg, "Role of heparin and heparinlike molecules in thrombosis and atherosclerosis," Fed. Proc., 1985, 44:404-9.

Rudolph et al., "Circulation persistence and biodistribution of lyophilized liposome-encapsulated hemoglobin: An oxygen-carrying resuscitative fluid," Crit. Care Med., 1994, 22:142-150.

Rudolph, "The Freeze-Dried Preservation of Liposome Encapsulated Hemoglobin: A Potential Blood Substitute," Cryobiology, 1988, 25:277-284.

Rush et al., "Microheterogeneity of Erythropoietin Carbohydrate Structure," Anal. Chem., 1995, 67(8):1442-1452.

Ruttmann et al., "In vivo investigation into the effects of haemodilution with hydroxyethylstarch (200/0.5) and normal saline on coagulation," Br. J. Anaesthesia, 1998, 80(5):612-616.

Sadamoto et al., "Control of Bacteria Adhesion by Cell-Wall Engineering," J. Am. Chem. Soc., 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," J. Pharmacol. Exp. Ther., 1997, 280(2):1038-1042.

Sakai et al., "Synthesis and Physicochemical Characterization of a Series of Hemoglobin-Based Oxygen Carriers: Objective Comparison between Cellular and Acellular Types," Bioconj. Chem., 2000, 11:56-64.

Sato et al., "Disposition of a Polymeric Prodrug of Mitomycin C, Mitomycin C-Dextran Conjugate, in the Perfused Rat Liver," J. Pharm. Sci., 1989, 78:11-16.

Sawaikar et al., "Products active on mosquitoes. Part VII, Synthesis and biological activity of longifolene derivatives," Indian Journal of Chemistry, 1995, 34B:832-835.

Scaglione et al., "A New Model Examining Intracellular and Extracellular Activity of Amoxicillin, Azithromycin, and Clarithromycin in Infected Cells," Chemotherapie, 1993, 39:416-423.

Schäfer et al., "Two-year double-blind trial of a monomethoxy polyethylene glycol (mPEG) modified grass pollen extract at different dose levels," Ann. Allergy, 1992, 68(4):334-339.

Schlenke et al., "Construction and characterization of stably transfected BNK-21 cells with human-type sialylation characteristic," Cytotechnology, 1999, 30:17-25.

Schlesinger, "Alphaviruses—vectors for the expression of heterologous genes," Trends Biotechnol., 1993, 11(1):18-22.

Schmoll et al. (eds.), "Summary of Basics of Oncology and Current Therapeutic Approaches," Compendium for Internistic Oncology, 1996, Table of Contents with English Summary.

Schottelius et al., "Improvement of Pharmacokinetics of Radioiodinated Tyr$^3$-Octreotide by Conjugation with Carbohydrates," Bioconjugate Chem., 2002, 13:1021-1030.

Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," Vaccine, 2000, 18:1273-1281.

Shah et al., "Characterization of Colony-stimulating Activity Produced by Human Monocytes and Phytohemagglutinin-stimulated Lymphocytes," 1977, Blood, 50(5):811-821.

Shao and Tam, "Unprotected peptides as building blocks for the synthesis of peptide dendrimers with oxime, hydrazone and thiazolidine linkages," J. Am. Chem. Soc., 1995, 117(14):3893-3899.

Sharaf et al., "studies on Aroyl- and Aryl-Hydrazide Derivatives from D-glycero-D-gulo-Heptono-1,4-Lactone," Carb. Res., 1981, 91:39-48.

Shin et al., "Fmoc-Based Synthesis of Peptide-αThioesters: Application to the Total Chemical Synthesis of a Glycoprotein by Native Chemical Ligation," J. Am. Chem. Soc., 1999, 121:11684-11689.

Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," Exp. Hematol., 1989, 17:116-119.

Shu, "Somogyi Micro Copper Method," Meth. Carb. Chem., 1962, 1:383-388.

Simmons G., et al; Potent inhibition of HIV-1 infectivity in macrophages and lymphocytes by a novel CCr5 antagonist; Science, 1997, 276:276-279.

Snyder et al., "HbXL99α: A hemoglobin derivative that is cross-linked between the α subunits is useful as a blood substitute," Proc. Natl. Acad. Sci., 1987, 84:7280-4.

Sommermeyer et al., "Hydroxyethylstarch for Clinical Application: Physical and Chemical Characterisation," Krankenhauspharmazie, 1987, 8:271-278.

Somogyi, "Determination of reducing sugars," Meth. Carb. Chem., 1962, 1:384-386.

Song et al., "Toxicity and Antitumor Activity of the Conjugate of Mitomycin C with Carboxymethyl-chitin," Arch. Pract. Pharm., 1993, 53(3):141-147.

Souza et al., "Recombinant human granulocyte colony-stimulating factor: effects on normal and leukemic myeloid cells," Science, 1986, 232:61-65.

Soyez et al., "Biological evaluation of mitomycin C bound to a biodegradable polymeric carrier," J. Controlled Release, 1997, 47:71-80.

Spellman et al., "Carbohydrate structures of human tissue plasminogen activator expressed in Chinese hamster ovary cells," J. Biol. Chem., 1989, 264:14100-11.

Spivak and Hogans, "The In Vivo Metabolism of Recombinant Human Erythropoietin in the Rat," Blood, 1989, 73:90-99.

Staab, "New Methods in Preparatory Organic Chemistry IV. Synthesis using heterocyclic amides (azolides)," Angew. Chemie, 1962, 74(12):407-22.

Staros, "N-Hydroxysulfosuccinimide Active Esters: Bis(N-hydroxysulfosuccinimide) Esters of Two Dicarboxylic Acids Are Hydrophilic, Membrane-Impermeant, Protein Cross-Linkers," Biochemistry, 1982, 21:3950-3955.

Stetsenko et al, "Efficient conjugation of peptides to oligonucleotides by native ligation," J. Org. Chem., 2000, 65(16):4900-4908.

Stewart et.al., "Identification of the mechanism responsible for the increased fibrin specificity of TNK-tissue plasminogen activator relative to tissue plasminogen activator," J. Biol. Chem., 2000, 275(14):10112-10120.

Stille et al., "Atherosclerosis as Consequence of Chronic Infection by *Chlamydia pneumoniae*," Herz, 1998, 23:185-192 (w/English summary).

Sunamoto and Iwamoto, "Protein-Coated and Polysaccharide-Coated Liposomes as Drug Carriers," CRC Critical Review in Therapeutic Drug Carrier Systems, 1986, 2:117-136.

Sytkowski et al., "An Erythropoietin Fusion Protein Comprised of Identical Repeating Domains Exhibits Enhanced Biological Properties," J. Biol. Chem., 1999, 274(35):24773-24778.

Sytkowski et al., "Human erythropoietin dimers with markedly enhanced in vivo activity," Proc. Natl. Acad. Sci. USA, 1998, 95(3):1184-1188.

Takeuchi and Kobata, "Structures and functional roles of the sugar chains of human erythropoietins," Glycobiology, 1991, 1(4):337-346.

Takeuchi et al., "Relationship between sugar chain structure and biological activity of recombinant human erythropoietin produced in Chinese hamster ovary cells," Proc. Natl. Acad. Sci. USA, 1989, 86:7819-7822.

Tam et al., "Peptide Synthesis Using Unprotected Peptides Through Orthogonal Coupling Methods," Proc. Natl. Acad. Sci, USA, 1995, 92: 12485-12489.

Tam et al., "Soluble Dextran-Hemoglobin Complex as a Potential Blood Substitute," Proc. Natl. Acad. Sci. USA, 1976, 73(6):2128-2131.

Tanaka et al., "Pharmacokinetics of recombinant human granulocyte colony-stimulating factor conjugated to polyethylene glycol in rats," Cancer Research, 1991, 51:3710-3714.

Tebbutt, "Technology evaluation: transgenic alpha-1-antitrypsin (AAT), PPL therapeutics," Curr. Opin. Mol. Ther., 2000, 2(2):199-204.

Thim et al., "Amino acid sequence and posttranslational modifications of human factor VIIa from plasma and transfected baby hamster kidney cells," Biochemistry, 1988, 27:7785-7793.

Thomas et al., "Measuring blood volume with fluorescent-labeled hydroxyethyl starch," Crit. Care Med., 2000, 28(3):627-631.

Thomas, "Carbohydrate Binding Sites," Meth. Enzymol., 1977, 46:362-368.

Thorpe et al., "Blockade of the galactose-binding sites of ricin by its linkage to antibody," Eur. J. Biochem., 1984, 140:63-71.

Toole et al., "Molecular cloning of a cDNA encoding human antihaemophilic factor," Nature, 1984, 312(5992):342-7.

Toyama et al., "Surface design of SPR-based immunosensor for the effective binding of antigen or antibody in the evanescent field using mixed polymer matrix," Sensors and Actuators B, 1998, 52:65-71.

Travis and Salvesen, "Human plasma proteinase inhibitors," Ann. Rev. Biochem., 1983, 52:655-709.

Ubeda and Habener, "The large subunit of the DNA replication complex C (DSEB/RF-C140) cleaved and inactivated by caspase-3 (CPP32/YAMA) during Fas-induced apoptosis," J. Biol. Chem., 1997, 272(31):19562-8.

Van Patten et al., "Oxidation of Methionine Residues in Antithrombin," J. Biol. Chem., 1999, 274(15):10268-10276.

Veronese et al., "Surface Modification of Proteins. Activation of Monomethoxy-Polyethylene Glycols by Phenylchloroformates and Modification of Ribonuclease and Superoxide Dismutase," Appl. Biochem. Biotech., 1985, 11:141-152.

Veronese, "Peptide and protein PEGylation: a review of problems and solutions," Biomaterials, 2001, 22(5):405-417.

Vilaseca et al., "Protein conjugates of defined structure: Synthesis and use of a new carrier molecule," Bioconjugate Chemistry, 1993, 4(6):515-520.

Wadhwa et al, "Immunogenicity of Granulocyte-Macrophage Colony-Stimulating Factor (GM-CSF) products in patients undergoing combination therapy with GM-CSF," Clinical Cancer Research, 1999, 5:1351-1361.

Wang et al., Bioconj Chem, 1998, 9:749-757.

Wasley et al., "The Importance of N- and O-Linked Oligosaccharides for the Biosynthesis and In Vitro and In Vivo Biologic Activities of Erythropoietin," Blood, 1991, 77(12):2624-2632.

Watanabe et al., "A facile synthesis of carboxylic thiol esters from carboxylic acids and thiols," Chem. Lett., 1976, 741-742.

Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," Bioconjugate Chem., 1990, 1:96-99.

Weidler et al., "Pharmakokinetische Merkmale als Kriterien für den klinischen Einsatz von Hydroxyethylstärke," Arzneim.-Forsch./Drug Res., 1991, 41:494-498 (w/English summary).

Weisshaar et al., "NMR investigations of the N-linked oligosaccharides at individual glycosylation sites of human lutropin."; Eur. J. Biochem., 1991, 195:257-268.

White and Kennedy, "Oligosaccharides," Carbohydrate analysis: a practical approach, 1996, Chaplin and Kennedy (eds.), Chapter 2, pp. 1-36.

Whitesides et al., "Rates of Thiol-Disulfide Interchange Reactions between Mono- and Dithiols and Ellman's Reagent," J. Org. Chem., 1977, 42(2):332-338.

Wilchek, M., Bayer, E.A., Labeling "Glycoconjugates with Hydrazide Reagents", 1987, Methods in Enzymology, 138, 429-442.

Wong et al., "Analysis of carbohydrate-protein interactions with synthetic N-linked neoglycoconjugate probes," Biochem. J., 1993, 296:817-825.

Wong et al., "Synthetic glycosylation of proteins using N-(β-saccharide) iodoacetamides: applications in site-specific glycosylation and solid-phase enzymic oligosaccharide synthesis," Biochem. J., 1994, 300:843-850.

Wong, Chemical Dictionary Entry Concerning Carbohydrates, Chemistry of Protein Conjugation and Cross-Linking, 1993, CRCS, Inc., 6 pages including English-language Abstract.

Wong, Chemistry of protein conjugation and cross-linking, 1993, CRCS, Inc. (TOC only).

Wright et al., "High level expression of active human alpha-1-antitrypsin in the milk of transgenic sheep," Biotechnology NY, 1991, 9:830-4.

Xue and Wong; "Preparation of Conjugated Hemoglobins," Meth. Enzymol., 1994, 231:308-322.

Yalpani et al., "Selective Chemical Modifications of Dextran," J. Polymer Science: Polymer Chemistry Edition, 1985, 23:1395-1405.

Yamaguchi et al., "Effects of site-directed removal of N-glycosylation sites in human erythropoietin on its production and biological properties," J. Biol. Chem., 1991, 266(30):20434-20439.

Yang et al., "Functional changes of carboxymethyl potato starch by conjugation with amino acids," Biosci. Biotechnol. Biochem., 1995, 59(12):2203-2206.

Yoshida, "Glycamine Formation via Reductive Amination of Oligosaccharides with Benzylamine," Meth. Enzymol., 1994, 247:55-64.

Yoshitake et al., "Nucleotide sequence of the gene for human factor IX (antihemophilic factor B)," Biochemistry, 1985, 24:3736-3750.

Zalipsky, "Functionalized Poly(ethylene glycol) for Preparation of Biologically Relevant Conjugates," Bioconjugate Chem., 1995, 6:150-165.

Zara et al., "A Carbohydrate-Directed Heterobifunctional Cross-Linking Reagent for the Synthesis of Immunoconjugates," Anal. Biochem., 1991, 194:156-162.

Zettlmeissl et al., "Characterization of Recombinant Human Antithrombin III Synthesized in Chinese Hamster Ovary Cells," J. Biol. Chem., 1989, 264 (35):21153-21159.

Zhou et al., "Application of capillary electrophoresis, liquid chromatography, electrospray-mass spectrometry and matrix-assisted laserdesorption/ionization—time of flight—mass spectrometry to the characterization of recombinant human erythropoietin," Electrophoresis, 1998, 19(13):2348-2355.

Zou et al., "Allylmalonamide as a bivalent linker: Synthesis of biantennary Gm3-saccharide-Keyhole limpet hemocyanin glycoconjugate and the immune response in mice," Glycoconj. J., 1999, 16:507-515.

Zucali and Sulkowski, "Purification of human urinary erythropoietin on controlled-pore glass and silicic acid," Exp. Hematol., 1985, 13(3):833-837.

"Heterobifunctional Crosslinkers," Molecular Biosciences, located at http://web/archive.org/web/20011104182428/ http://www.molbio.com/Heterobi.htm, printed Jun. 6, 2011, 13 pages.

Caliceti et al., "Immunological properties of uricase conjugated to neutral soluble polymers," Bioconjugate Chem., 2001, 12:515-522.

Cavallaro et al., "Folate-mediated targeting of polymeric conjugates of gemcitabine," Int. J. Pharmaceutics, 2006, 307:258-269.

Dörwald, Side Reactions in Organic Synthesis: A guide to Successful Synthesis Design, Jan. 2005, 4 pages.

Forno et al., "N- and O-linked carbohydrates and glycosylation site occupancy in recombinant human granulocyte-macrophage colony-stimulating factor secreted by a Chinese hamster ovary cell line," Eur. J. Biochem., 2004, 271:907-919.

Grieco et al., "Aryl selenocyanates and aryl thiocyanates: reagents for the preparation of activated esters," J. Org. Chem., 1978, 43(6):1283-1285.

Harada et al., "Determinants for the drug release from T-0128, camptothecin analogue-carboxymethyl dextran conjugate," J. Controlled Release, 2000, 69: 399-412.

Harada, et al. "Carrier and dose effects on the pharmacokinetics of T-0128, a camptothecin analogue-carboxymethyl dextran conjugate, in non-tumor-and tumor-bearing rats," J. Controlled Release, 2001, 71:71-86.

Johnson, "Oxime," in AccessScience, © McGraw-Hill Companies, 2008, jttp://www.accessscience.com.

Lee, ed., Peptide and Protein Drug Delivery, Marcel Dekker, 1991, p. 65.

Pasut et al., "Antitumoral activity of PEG-gemcitabine prodrugs targeted by folic acid," J. Controlled Release, 2008, 127(3):239-248.

Riess, "Oxygen carriers ('blood substitutes')—raison d'etre, chemistry, and some physiology," Chem. Rev., 2001, 101:2797-2919.

Rotondaro et al., "Purification and characterization of two recombinant human granulocyte colony-stimulating factor glycoforms," Mol. Biotechnol., 1999, 11: 117-128.

Seymour et al., "A phase 1 study of BAY 38-3441 given as a short infusion daily for five days every 3 weeks. A National Cancer Institute of Canada clinical trials group study," Eur. J. Cancer, 2001, 37(1):S73.

Svenson and Lindberg, "Coupling of acid labile Salmonella specific oligosaccharides to macromolecular carriers," J. Immunolog. Meth., 1979, 25: 323-335.

Svenson, "Immunochemistry of Salmonella O-antigens: Preparation of an octasaccharide-bovine serum albumin immunogen representative of Salmonella serogroup B O-antigen and characterization of the antibody response," J. Immunol., 1978, 120(5): 1750-1757.

Veronese, "Peptide and protein PEGylation: a review of problems and solutions," Biomaterials, 2001, 22:405-417.

Zhang, et al., "Thiazolidine formation as a general and site-specific conjugation method for synthetic peptides and proteins," Anal. Biochem., 1996, 233:87-93.

European Pharmacopoeia—Supplement, "Haemodialysis Solutions," 2001, 911-918.

Gaucher et al., "Stereospecific synthesis and characterization of aminoglycoside ligands from diethylenetriamine," J. Organic Chem., 1999, 64:1402-4015.

Gerwech et al., "Tumor pH controls the in vivo efficacy of weak acid and base chemotherapeutics," Mol. Cancer Ther., 2006, 5(5):1275-1279.

Luo et al., "Controlled DNA delivery systems," Pharm. Res., 1999, 16(8):1300-1308.

Thermo Scientific Pierce "Crosslinking Technical Handbook," 2009, 48pgs.

Waltzinger et al., "Pharmacokinetics and tolerability of a new hydroxyethyl starch (HES) specification [HE (130/0.4)] after single-dose infusion of 6% or 10% solutions in healthy volunteers," Pharmacokinetics, 1998, 16(2):151-160.

Grieco et al., "Favored reduction of α-chlorosilanes vs. α-chloroalkanes with tri-n-butyltin hydride," J. Org. Chem., 1978, 43(6):1285.

Heterobifunctional Crosslinkers by Molecular Biosciences [http://www.molbio.comlHeterobi.htm], published Nov. 2001; retrieved Jun. 6, 2011.

Crosslinking Agents, Pierce Company, available at http://www.piercenet.com/browse.cfm?fldID=0203, retrieved Aug. 25, 2011.

Svenson et al., "Oligosaccharide-protein conjugate: A novel approach for making Salmonella O-antigen immunogens," FEMS Microbiology Letters, 1977, 1: 145-148.

Gelbrich, "Untersuchungen zur Synthese neuartiger Cellulosematerialien durch topochemische Polymerreaktionen an mikrokristallinen Cellulosen," PhD Dissertation Paper, Vom Fachbereich Chemie, der Technischen Universitat Darmstadt, 1999, 157 pages (English abstract included).

Lonngren et al., "Aldonate Coupling, A Simple Procedure for the Preparation of Carbohydrate-Protein Conjugates for Studies of Carbohydrate-Binding Proteins," Arch. of BioChem. and BioPhys., 1976, 175:661-669.

Orlando, "Modification of proteins and low molecular weight substances with hydroxyethyl starch (HES)," PhD Dissertation Paper, Justus-Liebig Universitat Giessen, 2003, 191 pages.

Blackburn and Gait (Eds), "DNA and RNA Structure," in Nucleic Acids in Chemistry and Biology, 2nd Edition, 1996, Oxford University Press, pp. 15-81.

English and Gauss, "Chemically modified oligonucleotides as probes and inhibitors," Angew. Chem. Int. Ed. Engl., 1991, 30:613-629.

Ng et al., "Pegaptanib, a targeted anti-VEGF aptamer for ocular vascular disease," Nature Reviews, 2005, 5:123-126.

Nielsen et al., "Sequence-selective recognition of DNA by Strand displacement with a thymidine-substituted polyamide," Science, 1991, 254:1497-1500.

Pieve et al., "Modification of thiol functionalized aptamers by conjugation of synthetic polymers," Bioconjugate Chemistry, 2012, 21:169-174.

* cited by examiner

A B  C A

HYDROXYALKYL STARCH DERIVATIVES

CROSS-REFERENCE TO RELATED APPLICATIONS

This application is a divisional of U.S. application Ser. No. 11/077,906, filed on Mar. 11, 2005, which is a continuation-in-part and claims benefit under 35 U.S.C. §120 of International Application No. PCT/EP03/08859 having an International Filing Date of Aug. 8, 2003, which published in English as International Publication Number WO 2004/024777, and which claims the benefit of priority of European Patent Application No. 02020425.1, having a filing date of Sep. 11, 2002, and U.S. Provisional Application Ser. No. 60/409,781 having a filing date of Sep. 11, 2002.

The present invention relates to hydroxyalkyl starch derivates, particularly hydroxyalkyl starch derivatives obtainable by a process in which hydroxyalkyl starch is reacted with a primary or secondary amino group of a linker compound. According to an especially preferred embodiment, the present invention relates to hydroxyalkyl starch derivatives obtainable by a process according to which hydroxyalkyl starch is reacted with a primary or secondary amino group of a linker compound and the resulting reaction product is reacted with a polypeptide, preferably with a glycoprotein and especially preferably with erythropoietin, via at least one other reactive group of the linker compound. A hydroxyalkyl starch which is especially preferred is hydroxyethyl starch. According to the present invention, the hydroxyalkyl starch and preferably the hydroxylethyl starch is reacted with the linker compound at its reducing end which is not oxidized prior to said reaction.

Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., 1987, Krankenhauspharmazie, 8(8), 271-278; and Weidler et al., 1991, Arzneim.-Forschung/Drug Res., 41, 494-498).

Amylopectin consists of glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

Some ways of producing a hydroxyethyl starch derivative are described in the art.

DE 26 16 086 discloses the conjugation of hemoglobin to hydroxyethyl starch wherein, in a first step, a cross-linking agent, e.g. bromocyane, is bound to hydroxyethyl starch and subsequently hemoglobin is, linked to the intermediate product.

One important field in which HES is used is the stabilisation of polypeptides which are applied, e.g., to the circulatory system in order to obtain a particular physiological effect. One specific example of these polypeptides is erythropoietin, an acid glycoprotein of approximately 34,000 kD which is essential in regulating the level of red blood cells in the circulation.

A well-known problem with the application of polypeptides and enzymes is that these proteins often exhibit an unsatisfactory stability. Especially erythropoietin has a relatively short plasma half live (Spivak and Hogans, 1989, Blood 73, 90; McMahon et al., 1990, Blood 76, 1718). This means that therapeutic plasma levels are rapidly lost and repeated intravenous administrations must be carried out. Furthermore, in certain circumstances an immune response against the peptides is observed.

It is generally accepted that the stability of polypeptides can be improved and the immune response against these polypeptides is reduced when the polypeptides are coupled to polymeric molecules. WO 94/28024 discloses that physiologically active polypeptides modified with polyethyleneglycol (PEG) exhibit reduced immunogenicity and antigenicity and circulate in the bloodstream considerably longer than unconjugated proteins, i.e. have a longer clearance rate. However, PEG-drug conjugates exhibit several disadvantages, e.g. they do not exhibit a natural structure which can be recognized by elements of in vivo degradation pathways. Therefore, apart from PEG-conjugates, other conjugates and protein polymerates have been produced. A plurality of methods for the cross-linking of different proteins and macromolecules such as polymerase have been described in the literature (see e.g. Wong, Chemistry of protein conjugation and cross-linking, 1993, CRCS, Inc.).

The HES-drug conjugates disclosed in the art suffer from the disadvantage that HES is not conjugated site-specifically to the drug. Consequently, the conjugation results in a very heterogenous product having many components that may be inactive due to the destruction of the 3-dimensional structure during the conjugation step. Therefore, there is a need for further improved HES-polypeptides conjugates with improved stability and/or bioactivity.

One method of producing these conjugates uses, as starting material, an oxidized form of HES which is reacted with a crosslinking compound wherein the resulting product is reacted with a polypeptide or further modified and subsequently reacted with a polypeptide. It is a major disadvantage of this method that in a first step, the original HES has to be selectively oxidized, generally at its reducing end, by oxidizing the terminal aldehyde group and/or hemiacetale group to a lactone, thus rendering the overall process more difficult and expensive.

WO 02/08079 A2 discloses compounds comprising a conjugate of an active agent and a hydroxyalkyl starch wherein active agent and hydroxyalykl starch are either linked directly or via a linker compound. As far as the direct linkage is concerned, the reaction of active agent and hydroxyalkyl starch is carried out in an aqueous medium which comprises at least 10 wt.-% of water. No examples are given which are directed to a hydroxyalkyl starch derivative which is produced by reacting hydroxyalkyl starch at its reducing end with a crosslinking compound comprising the structure unit —NH— in an aqueous medium. All examples are directed to hydroxyalkyl starch which is oxidized prior to a further reaction, the specific teaching of WO 02/08079 A2 thus having the aforementioned disadvantages.

Therefore, it is an object of the present invention to provide a method of producing a hydroxyalkyl starch derivative which allows for reacting hydroxyalkyl starch at its reducing end with a suitable compound wherein the reducing end of the starch is not oxidized prior to the reaction.

It is a further object of the present invention to provide a method of producing a hydroxyalkyl starch derivative which allows for reacting hydroxyalkyl starch at its reducing end with a suitable compound wherein the reducing end of the starch is not oxidized prior to the reaction, said method being further characterized in that the reaction product of the reaction of hydroxyalkyl starch at its reducing end with a suitable compound is further reacted with at least one further compound.

It is a still further object of the present invention to provide a method as described above wherein the at least one further compound is a polypeptide, preferably a protein, more preferably erythropoietin.

It is yet another object of the present invention to provide a hydroxyalkyl starch derivative which is obtainable by a method as described above which comprises reacting hydroxyalkyl starch at its reducing end with a suitable compound wherein the reducing end of the starch is not oxidized prior to the reaction.

Therefore, the present invention relates to a method of producing a hydroxyalkyl starch derivative comprising reacting hydroxyalkyl starch (HAS) of formula (I)

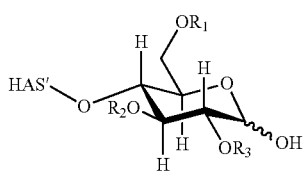

(I)

at its reducing end which is not oxidized prior to said reaction, with a compound of formula (II)

R'—NH—R''  (II)

wherein $R_1$, $R_2$ and $R_3$ are independently hydrogen or a linear or branched hydroxyalkyl group, and wherein either R' or R'' or R' and R'' comprise at least one functional group X capable of being reacted with at least one other compound prior to or after the reaction of (I) and (II).

In the context of the present invention, the term "hydroxyalkyl starch" (HAS) refers to a starch derivative which has been substituted by at least one hydroxyalkyl group. Therefore, the term hydroxyalkyl starch as used in the present invention is not limited to compounds where the terminal carbohydrate moiety comprises hydroxyalkyl groups $R_1$, $R_2$, and/or $R_3$ as depicted, for the sake of brevity, in formula (I), but also refers to compounds in which at least one hydroxy group present anywhere, either in the terminal carbohydrate moiety and/or in the remaining part of the starch molecule, HAS', is substituted by a hydroxyalkyl group $R_1$, $R_2$, or $R_3$.

In this context, the alkyl group may be a linear or branched alkyl group which may be suitably substituted. Preferably, the hydroxyalkyl group contains 1 to 10 carbon atoms, more preferably from 1 to 0.6 carbon atoms, more preferably from 1 to 4 carbon atoms, and even more preferably 2-4 carbon atoms. "Hydroxyalkyl starch" therefore preferably comprises hydroxyethyl starch, hydroxypropyl starch and hydroxybutyl starch, wherein hydroxyethyl starch and hydroxypropyl starch are particularly preferred.

Hydroxyalkyl starch comprising two or more different hydroxyalkyl groups are also possible.

The at least one hydroxyalkyl group comprised in HAS may contain two or more hydroxy groups. According to a preferred embodiment, the at least one hydroxyalkyl group comprised HAS contains one hydroxy group.

The expression "hydroxyalkyl starch" also includes derivatives wherein the alkyl group is mono- or polysubstituted. In this context, it is preferred that the alkyl group is substituted with a halogen, especially fluorine, or with an aryl group, provided that the HAS remains soluble in water. Furthermore, the terminal hydroxy group a of hydroxyalkyl group may be esterified or etherified.

Furthermore, instead of alkyl, also linear or branched substituted or unsubstituted alkene groups may be used.

Hydroxyalkyl starch is an ether derivative of starch. Besides of said ether derivatives, also other starch derivatives can be used in the context of the present invention. For example, derivatives are useful which comprise esterified hydroxy groups. These derivatives may be e.g. derivatives of unsubstituted mono- or dicarboxylic acids with 2-12 carbon atoms or of substituted derivatives thereof. Especially useful are derivatives of unsubstituted monocarboxylic acids with 2-6 carbon atoms, especially derivatives of acetic acid. In this context, acetyl starch, butyl starch and propyl starch are preferred.

Furthermore, derivatives of unsubstituted dicarboxylic acids with 2-6 carbon atoms are preferred.

In the case of derivatives of dicarboxylic acids, it is useful that the second carboxy group of the dicarboxylic acid is also esterified. Furthermore, derivatives of monoalkyl esters of dicarboxylic acids are also suitable in the context of the present invention.

For the substituted mono- or dicarboxylic acids, the substitute groups may be preferably the same as mentioned above for substituted alkyl residues.

Techniques for the esterification of starch are known in the art (see e.g. Klemm D. et al, Comprehensive Cellulose Chemistry Vol. 2, 1998, Whiley-VCH, Weinheim, N.Y., especially chapter 4.4, Esterification of Cellulose (ISBN 3-527-29489-9).

Hydroxyethyl starch (HES) is most preferred for all embodiments of the present, invention.

Therefore, the present invention also relates to a method as described above wherein the hydroxyalkyl starch is hydroxyethyl starch.

HES is mainly characterized by the molecular weight distribution and the degree of substitution. There are two possibilities of describing the substitution degree:
1. The substitution degree can be described relatively to the portion of substituted glucose monomers with respect to all glucose moieties (DS).
2. The substitution degree can be described as the "molar substitution" (MS), wherein the number of hydroxyethyl groups per glucose moiety are described.

HES solutions are present as polydisperse compositions, wherein each molecule differs from the other with respect to the polymerisation degree, the number and pattern of branching sites, and the substitution pattern. HES is therefore a mixture of compounds with different molecular weight. Consequently, a particular HES solution is determined by average molecular weight with the help of statistical means. In this context, $M_n$ is calculated as the arithmetic mean depending on the number of molecules. Alternatively, $M_w$, the weight mean, represents a unit which depends on the mass of the HES.

In the context of the present invention, hydroxyethyl starch may have a mean molecular weight (weight mean) of from 1 to 300 kDa, wherein a mean molecular weight of from 5 to 100 kDa is more preferred. Hydroxyethyl starch can further exhibit a molar degree of substitution of from 0.1 to 0.8 and a ratio between $C_2:C_6$ substitution in the range of from 2 to 20 with respect to the hydroxyethyl groups.

As far as the residues $R_1$, $R_2$ and $R_3$ according to formula (I) are concerned there are no specific limitations given that compound (I) remains capable of being reacted with a compound according to formula (II). According to a preferred embodiment, $R_1$, $R_2$ and $R_3$ are independently hydrogen or a hydroxyalkyl group, a hydroxyaryl group, a hydroxyaralkyl group or a hydroxyalkaryl group having of from 1 to 10 carbon atoms. Hydrogen and hydroxyalkyl groups having of from 1 to 6 carbon atoms are preferred. The alkyl, aryl, aralkyl and/or alkaryl group may be linear or branched and suitably substituted.

Therefore, the present invention also related to a method as described above wherein $R_1$, $R_2$ and $R_3$ are independently hydrogen or a linear or branched hydroxyalkyl group with from 1 to 6 carbon atoms.

Thus, $R_1$, $R_2$ and $R_3$ may be hydroxyhexyl, hydroxypentyl, hydroxybutyl, hydroxypropyl such as 1-hydroxypropyl, 2-hydroxypropyl, 3-hydroxypropyl, 1-hydroxyisopropyl, 2-hydroxyisopropyl, hydroxyethyl such as 1-hydroxyethyl, 2-hydroxyethyl, or hydroxymethyl. Hydrogen and hydroxyethyl groups are preferred, hydrogen and the 2-hydroxyethyl group being especially preferred.

Therefore, the present invention also relates to a method as described above wherein $R_1$, $R_2$ and $R_3$ are independently hydrogen or a 2-hydroxyethyl group.

According to the present invention, hydroxyalkyl starch is reacted with a compound of formula (II) wherein compound (II) may be reacted with another compound prior to the reaction with compound (I), to give a hydroxyalkyl starch derivative. As to compound (II), there are no specific limitations if compound (II) is capable of being reacted via the NH group bridging R' and R" with compound (I) at its reducing end which is not oxidized, to give a hydroxyalkyl starch derivative.

Preferred residues R' of compound (II) are hydrogen and alkyl, cycloalkyl, aryl, aralkyl, arylcycloalkyl, alkaryl or cycloalkylaryl residues where cycloalkyl, aryl, aralkyl, arylcycloalkyl, alkaryl or cycloalkylaryl residues may be linked directly to the NH group bridging R' and R" of compound (II) or, according to another embodiment, may be linked by an oxygen bridge to the NH group bridging R' and R" of compound (II). The alkyl, aryl, aralkyl or alkaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Therefore, the present invention also relates to a method as described above wherein R' is hydrogen or a linear or branched alkyl or alkoxy group.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

Therefore, the present invention also relates to a method as described above wherein R' is hydrogen or a methyl or a methoxy group.

Apart from the functional group X, R" may comprise at least one additional functional group W. This at least one additional functional group W generally may be anywhere in R". Preferably, W is directly linked to the NH group R' is linked to.

In general, there are no specific limitations regarding functional group W given that compound (I) is capable of being reacted with compound (II). In preferred embodiments, functional group W comprises the structure unit —NH— and/or the structure unit —(C=G)- where G is O or S, and/or the structure unit —SO$_2$—. According to more preferred embodiments, the functional group W is selected from the group consisting of

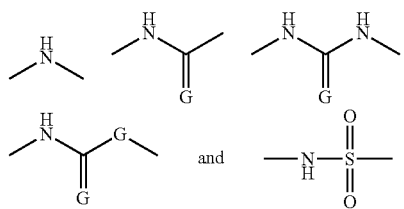

and where, if G is present twice, it is independently O or S.

According to preferred embodiments of the present invention where R' is H and W is linked directly to the NH group bridging R' and R", R' and the NH group bridging R' and R" form together with W, the one of following groups:

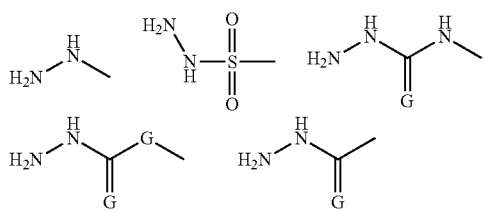

As far as the at least one functional group X which is comprised in R' and/or R", preferably in R", no specific limitations exist. In general, all functional groups are possible which allow the reaction with at least one further compound.

As far as this reaction with a further compound is concerned, all kinds of interactions of the at least one functional group with the at least one further compound are possible.

Among others, reactions of the at least one functional group X with a further compound are possible which lead to a covalent linkage, a ionic linkage and/or a van-der-Waals linkage, the covalent linkage being especially preferred.

Among others, the following functional groups X are to be mentioned:

C—C-double bonds or C—C-triple bonds or aromatic C—C-bonds;
the thio group or the hydroxy groups;
alkyl sulfonic acid hydrazide, aryl sulfonic acid hydrazide;
1,2-dioles;
1,2-aminoalcohols;
the amino group —NH$_2$ or derivatives of the amino groups comprising the structure unit —NH— such as aminoalkyl groups, aminoaryl group, aminoaralkyl groups, or alkarlyamino groups;
the hydroxylamino group —O—NH$_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;

an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trochlorophenyl;
wherein Q is absent or NH or a heteroatom such as S or O;
—NH—NH$_2$, or —NH—NH—;
NO$_2$;
the nitril group;
carbonyl groups such as the aldehyde group or the keto group; the carboxy group;
the —N=C=O group or the —N=C=S group;
vinyl halide groups such as the vinyl iodide or the vinyl bromide group or vinyltriflate;
—C≡C—H;
—(C=NH$_2$Cl)—O Alkyl
groups —(C=O)—CH$_2$-Hal wherein Hal is Cl, Br, or I;
—CH=CH—SO$_2$—;
a disulfide group comprising the structure —S—S—;
the group

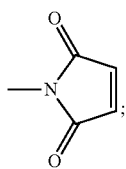

the group

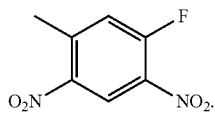

Among these groups, the thio group, the amino group, the hydroxylamino group, the alkoxyamino groups and the following groups are especially preferred:

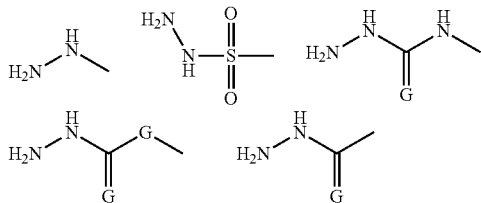

Therefore, the present invention also relates to a method as described above wherein the at least one functional group X is selected from the group consisting of —SH, —NH$_2$, —O—NH$_2$, —NH—O-alkyl, —(C=G)-NH—NH$_2$, -G-(C=G)-NH—NH$_2$, —NH—(C=G)-NH—NH$_2$, and —SO$_2$—NH—NH$_2$ where G is O or S and, if G is present twice, it is independently O or S.

As far as the alkoxyamino groups are concerned, particular preference is given to the propoxyamino group, the ethoxyamino group and the methoxyamino group, the methoxyamino group —NH—O—CH$_3$ being especially preferred.

According to yet another aspect of the present invention, the at least one functional group X may be a group which is not capable of reacting directly with a given further compound but which may be chemically modified in order to be capable of reacting in the desired way. This modification of the functional group X comprised in compound (II) may be carried out either prior to the reaction of compound (II) with compound (I) or after the reaction of compound (II) with compound (I). If compound (II) comprises at least two, optionally chemically different, functional groups X, it is possible to modify at least one functional group X prior to the reaction of compound (II) with compound (I) and at least one functional group X after the reaction of compound (II) with compound (I).

As an example of a functional group X to be modified prior to the reaction with a further compound, a 1,2-amino alcohol or a 1,2-diol may be mentioned which is modified, e.g., by oxidation to form an aldehyd or a keto group.

Another example for a functional group X to be modified prior to the reaction with a further compound is a —NH$_2$ group which is, modified by the reaction with, e.g., a compound according to the following formula

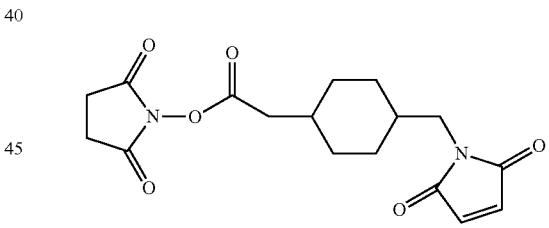

to give a structure of the following formula

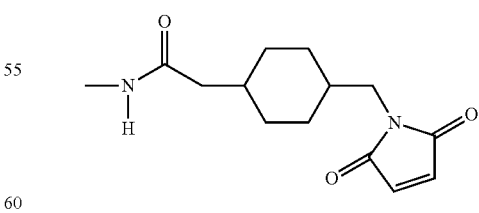

which is, e.g., reactive towards a thio group.

Another example for a functional group X to be modified prior to the reaction with a further compound is a —NH$_2$ group which is modified by the reaction with, e.g., a compound according to the following formula

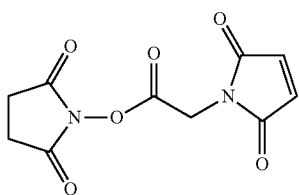 [SMILES: O=C(CN1C(=O)C=CC1=O)ON1C(=O)CCC1=O]

to give a structure of the following formula

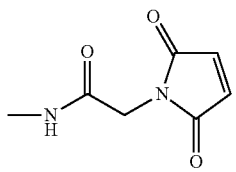

which is, e.g., reactive towards a thio group.

The at least one functional group X may be linked directly to the NH group bridging R' and R". Thus, according to one embodiment of the present invention, the functional group X is equivalent to R". Specific examples of compounds where X is directly linked to the NH group bridging R' and R" are, among others,

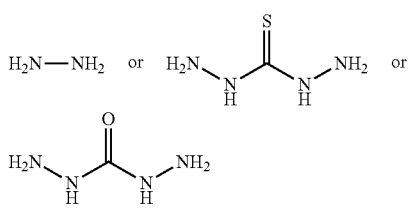

Another specific example of a such a compound which is also comprised in the present invention is $NH_3$.

According to another embodiment of the present invention, the NH group bridging R' and R" may be separated from the at least one functional group X by a linear or branched alkyl or cycloalkyl or an or aralkyl or arylcycloalkyl or alkaryl or cycloalkylaryl group, wherein these groups may comprise at least one heteroatom such as N, O, S, and wherein these groups may be suitably substituted. The size of the group separating NH, bridging R' and R", and the at least one functional group X may be adapted to the specific needs. Generally, the separating group has generally from 1 to 60, preferably from 1 to 40, more preferably from 1 to 20, more preferably from 1 to 10, more preferably from 1 to 6 and especially preferably from 1 to 4 carbon atoms. If heteroatoms are present, the separating group comprises generally from 1 to 20, preferably from 1 to 8 and especially preferably from 1 to 4 heteroatoms. According to particularly preferred embodiments of the present invention, the separating group comprises 1 to 4 oxygen atoms. The separating group may comprise an optionally branched alkyl chain or an aryl group or a cycloalkyl group having, e.g., from 5 to 7 carbon atoms, or be a aralkyl group, an alkaryl group where the alkyl part may be a linear and/or cyclic alkyl group. According to an even more preferred embodiment, the separating group is an alkyl chain of from 1 to 20, preferably from 1 to 8, more preferably from 1 to 6, more preferably from 1 to 4 and especially preferably from 2 to 4 carbon atoms. In case heteroatoms are present, a chain comprising 1 to 4 oxygen atoms is particularly preferred.

Specific examples of compounds (II) where X is separated from the NH group bridging R' and R" are, among others,

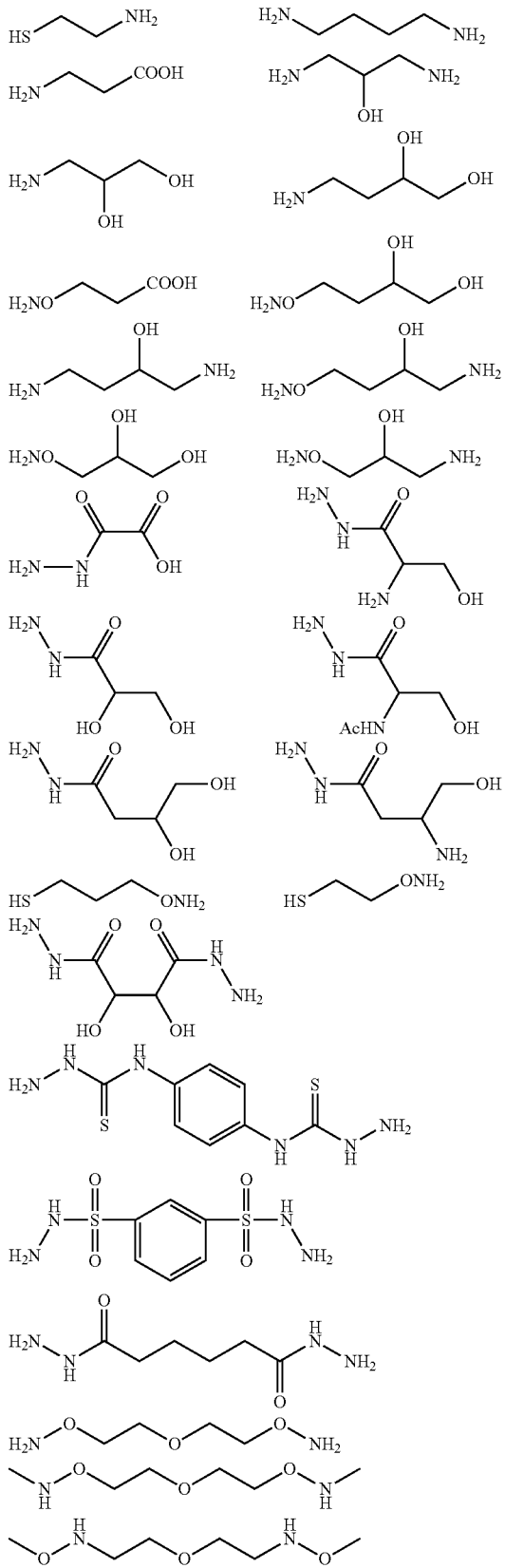

-continued

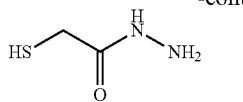

The group separating NH, bridging R' and R", and the at least one functional group X may be suitably substituted. Preferred substituents are, e.g, halides such as F, Cl, Br or I.

The group separating NH, bridging R' and R", and the at least one functional group X may comprise one or more cleavage sites such as

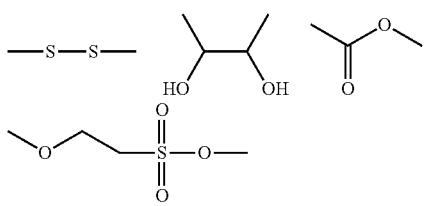

which allow for an easy cleavage of a resulting compound at a pre-determined site.

According to an especially preferred embodiment of the present invention, the compound (II) is O[2-(2-aminooxy-ethoxy)-ethyl]-hydroxyl amine

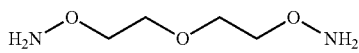

or carbohydrazide

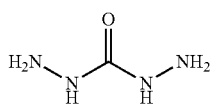

Therefore, the present invention also relates to a method as described above wherein compound (II) is O-[2-(2-aminooxy-ethoxy)-ethyl]-hydroxyl amine or carbohydrazide.

In case compound (II) comprises one or more chiral centers, compound (II) may be present in R conformation or in S conformation or as racemic compound with respect to each chiral center.

As described above, compound (I) may be reacted with compound (II) as such or with compound (II) which has been reacted with at least one further compound prior to the reaction with compound (I).

The reaction of compound (I) with compound (U) as such may be carried out in at least one suitable solvent. The respective solvent or mixture of two or more solvents may be adapted to the specific needs of the reaction conditions and the chemical nature of compounds (I) and (II). According to an especially preferred embodiment of the present invention, water is used as solvent, either alone or in combination with at least one other solvent. As at least one other solvent, DMSO, DMF, methanol and ethanol may be mentioned. Preferred solvents other than water are DMSO, DMF, methanol and ethanol.

Therefore, the present invention also relates to a method as described above wherein the reaction of compound (I) with compound (II) is carried out in an aqueous system.

The term "aqueous system" as used in the context of the present invention refers to a solvent or a mixture of solvents comprising water in the range of from at least 10% per weight, preferably at least 50% per weight, more preferably at least 80% per weight, even more preferably at least 90% per weight or up to 100% per weight, based on the weight of the solvents involved. The preferred reaction medium is water.

As far as the temperatures which are applied during the reaction are concerned, no specific limitations exist given that the reaction results in the desired hydroxyalkyl starch derivative.

In case compound (I) is reacted with compound (II), compound (II) being a hydroxylamine or a hydrazide, the temperature is preferably in the range of from 5 to 45° C., more preferably in the range of from 10 to 30° C. and especially preferably in the range of from 15 to 25° C.

In case compound (I) is reacted with compound (II), said reaction being a reductive amination, the temperature is preferably in the range of up to 100° C., more preferably in the range of from 20 to 95° C., more preferably in the range of from 25 to 90° C., more preferably in the range of from 70 to 90° C. and especially preferably in the range of from 75 to 85° C.

Therefore, the present invention also relates to a method as described above wherein the reaction of compound (I) and compound (II), compound (II) being a hydroxylamine or a hydrazide, is carried out at a temperature of from 5 to 45° C.

Therefore, the present invention also relates to a method as described above wherein the reaction of compound (I) and compound (II), said reaction being a reductive amination, is carried out at a temperature of from 25 to 90° C.

During the course of the reaction the temperature may be varied, preferably in the above-given ranges, or held essentially constant.

The reaction time for the reaction of compound (I) with (II) may be adapted to the specific needs and is generally in the range of from 1 h to 7 d.

In case compound (II) is a hydroxylamine or a hydrazide, the reaction time is preferably in the range of from 1 h to 3 d and more preferably of from 2 h to 48 h.

In case the reaction of compound (I) and compound (II) is a reductive amination, the reaction time is preferably in the range of from 2 h to 7 d.

The pH value for the reaction of compound (I) with (II) may be adapted to the specific needs such as the chemical nature of the reactants.

In case compound (II) is a hydroxylamine or a hydrazide, the pH value is preferably in the range of from 4.5 to 6.5.

In case the reaction of compound (I) and compound (II) is a reductive amination, the pH value is preferably in the range of from 8 to 12.

Therefore, the present invention also relates to a method as described above wherein the reaction of compound (I) and compound (II), compound (II) being a hydroxylamine or a hydrazide, is carried out at a pH of from 4.5 to 6.5.

Therefore, the present invention also relates to a method as described above wherein the reaction of compound (I) and compound (II), said reaction being a reductive amination, is carried out at a pH of from 8 to 12.

Specific examples of above mentioned reaction conditions are, e.g., a reaction temperature of about 25° C. and a pH of about 5.5 in case compound is a hydroxylamine, and a reaction temperature of about 80° C. and a pH of about 11 in case the reaction of compound (I) and compound (II) is a reductive amination.

The suitable pH value of the reaction mixture may be adjusted by adding at least one suitable buffer. Among the preferred buffers, sodium acetate buffer, phosphate or borate buffers may be mentioned.

According to a preferred embodiment of the present invention, the reaction product resulting from the reaction of compound (I) with compound (II) is reacted with at least one further compound via the at least one functional group X.

If necessary, the at least one functional group X may be protected with at least one suitable protecting group prior to the reaction of compound (I) with compound (II). In this respect, all conceivable protecting groups are possible which prevent the protected compound (II) from reacting with compound (I) via the at least one functional group X. Hence, the protecting group may be chosen depending from the chemical nature of the functional group X to be protected, from, e.g., the solvent the reaction is carried out in or the pH of the reaction mixture. Preferred protecting groups are, among others, the benzyloxycarbonyl group, the tert-butoxycarbonyl group, the methoxyphenyl group, the 2,4-dimethoxyphenyl group, triarly methyl groups, trityl, the monomethoxytrityl group, the dimethoxytrityl group, the monomethyltrityl group, the dimethyltrityl group, the trifluoracetyl group, phthalimin compounds, 2-(trialkylsilyl)ethoxy carbonyl compounds, Fmoc, the tert-butyl group, or trialkyl silyl groups.

If two or more different functional groups X are present in compound (II), at least one group may be protected whereas at least one other group may be left unprotected.

After the reaction of compound (I) with compound (II), the at least one protecting group may be left in the reaction product or removed by suitable methods such as conventional methods known to the person skilled in the art. If two different functional groups X are protected by suitable protecting groups, it is possible to remove at least one protecting group so as to make at least one functional group X available for further reaction with at least one further compound, and leave at least one other functional group protected until the reaction product of compound (I) with compound (II) is reacted with the further compound. Afterwards, the protecting group of the functional group still protected may be removed to make the remaining functional group X available for reaction with yet a further compound.

The use of at least one protecting group may be important for preventing the reaction from resulting in a hydroxyalkyl starch derivative consisting of a compound (II) which has been reacted with two or more compounds (I), i.e. a multiple HAS substituted compound (II). The same result, however, may be achieved by reacting compound (I) with an excess of compound (II). If an excess amount of compound (II) is used in the process of the present invention, the molar ratio of compound (II) to compound (I) is preferably in the range of from 2 to 100.

Once the reaction product of the reaction of compound (I) with compound (II) is formed, it may be isolated from the reaction mixture by at least one suitable method. If necessary, the reaction product may be precipitated prior to the isolation by at least one suitable method.

If the reaction product is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where water is used as solvent, the reaction mixture is contacted with a mixture of ethanol and acetone, preferably a 1:1 mixture, indicating equal volumes of said compounds, at a temperature, preferably in the range of from −20 to +50° C. and especially preferably in the range of from 0 to 25° C.

Isolation of the reaction product may be carried out by a suitable process which may comprise one or more steps. According to a preferred embodiment of the present invention, the reaction product is first separated off the reaction mixture or the mixture of the reaction mixture with e.g., the ethanol-acetone mixture, by a suitable method such as centrifugation or filtration. In a second step, the separated reaction product may be subjected to a further treatment such as an after-treatment like dialysis, centrifugal filtration or pressure filtration, ion exchange chromatography, HPLC, MPLC, gel filtration and/or lyophilisation. According to an even more preferred embodiment, the separated reaction product is first dialysed, preferably against water, and then lyophilized until the solvent content of the reaction product is sufficiently low according to the desired specifications of the product. Lyophilisation may be carried out at temperature of from 20 to 35° C., preferably of from 25 to 30° C.

The thus isolated reaction product of compound (I) and compound (II) may be further reacted with at least one other compound via at least one functional group X comprised in said reaction product.

Depending on the chemical nature of the functional group X, every conceivable compound capable of forming a chemical linkage with this group X may be used. For this reaction, one or more suitable solvents may be used, and all reaction parameters such as the temperature during the reaction, the reaction time, the ratios of the reactants or the pH value of the reaction mixture may be adapted to the specific needs.

According to a particularly preferred embodiment of the present invention, the at least one compound capable of forming a chemical linkage with the at least one functional group X is a polypeptide or a mixture of at least two different polypeptides.

Therefore, the present invention also relates to a method as described above wherein the reaction product of compound (I) and compound (II) is reacted with a polypeptide via the functional group X comprised in compound (II).

According to another particularly preferred embodiment of the present invention, the at least one further compound capable of forming a chemical linkage with the at least one functional group X is a crosslinking compound which is capable of forming a first chemical linkage with the at least one functional group X of the reaction product of compound (I) and compound (II), and a second chemical linkage with second further compound.

According to an even more preferred embodiment of the present invention, the second further compound is a polypeptide or a mixture of at least two different polypeptides.

In the context of this embodiment of the present invention, it is possible to react the reaction product of compound (I) and compound (II), the first hydroxyalkyl starch derivative, with the crosslinking compound to give a second hydroxyalykl starch derivative. This second hydroxyalykl starch derivative may be subsequently reacted with the second further compound, preferably a polypeptide, to give a third hydroxyalykl starch derivative.

It is, however, also possible to react the reaction product of compound (I) and compound (II), the first hydroxyalykl starch derivative, with a reaction product of the crosslinking compound with the second further compound, preferably a polypeptide.

Therefore, the present invention also relates to a method as described above wherein the reaction product of compounds (I) and (II) is reacted with a further compound, said further compound being a crosslinking compound, via reaction of a functional group V comprised in the crosslinking compound and a functional group X comprised in the reaction product of compounds (I) and (II).

Therefore, the present invention also relates to a method as described above wherein the reaction product of compounds (I) and (II) is reacted with a further compound, said further compound being a crosslinking compound, via reaction of a functional group V comprised in the crosslinking compound and a functional group X comprised in the reaction product of compounds (I) and (II), said crosslinking compound having been reacted with a second further compound prior to the reaction with the reaction product of compounds (I) and (II).

Therefore, the present invention also relates to a method as described above wherein the second further compound is a polypeptide, preferably erythropoietin, which is reacted with the crosslinking compound via reaction of a functional group X, comprised in the crosslinking compound.

Therefore, the present invention also relates to a method as described above wherein compound (II) is reacted with a first further compound, preferably a crosslinking compound, to give a first reaction product, said first reaction product is reacted with a second further compound to give a second reaction product, and said second reaction product is reacted with compound (I).

Therefore, the present invention also relates to a method as described above wherein a first further compound, preferably a crosslinking compound, is reacted with a second further compound, preferably a polypeptide, to give a first reaction product, said first reaction product is reacted with compound (II) to give a second reaction product, and said second reaction product is reacted with compound (I) to give the hydroxyalkyl starch derivative.

According to especially preferred embodiments of the present invention, the crosslinking compounds are used to form a chemical bridge between compound (II) or the reaction product of compounds (I) and (II), and a second further compound wherein the functional group of the second further compound which reacts with the crosslinking compound is a —SH group or an aldehyde group or a keto group, and the functional group of compound (II) or the reaction product of compounds (I) and (II) which reacts with the crosslinking compound is a group comprising the structure —NH—, particularly preferably —NH$_2$.

In the context of the present invention, the term "crosslinking compound" relates to chemical compounds which are capable of forming a linkage between compound (U) or the reaction product of compounds (I) and (II), and at least one given second further compound. Depending on the chemical nature of the second further compound, the crosslinking compound comprises at least one, functional group V capable of being reacted with the functional group X comprised in compound (II) or the reaction product of compounds (I) and (II), and at least one further functional group which is capable of forming a chemical linkage with the second further compound. This at least one further functional group comprised in the crosslinking compound may be a functional group of the type discussed above with regard to the functional group X.

The crosslinking compound may be used to enlarge the length of the overall chemical bridge between compound (I) and the second further compound, preferably a polypeptide, and/or to influence the chemical nature of the resulting reaction product, either with or without the second further compound, and/or provide the possibility to form a linkage between several second further compounds and the reaction product of compound (I), (II) and the crosslinking compound, and/or to chemically modify the functional group X comprised in the reaction product of compound (I) and (II) so as to render said reaction product capable of reacting with a given further compound.

Thus, embodiments of the present invention which are discussed above and which relate to the chemical modification of the functional group X being a —NH, group, with a further compound, e.g.

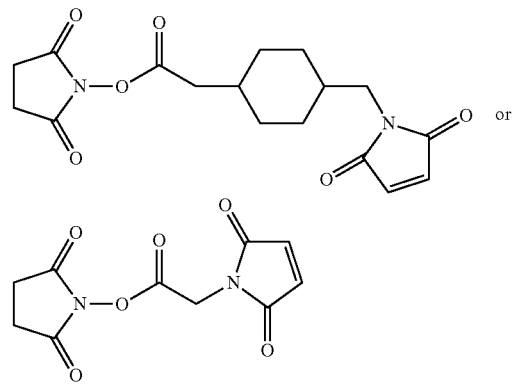

in order to provide the possibility for the reaction with an —SH group comprised in a second further compound, preferably a polypeptide, are specific examples of reacting the reaction product of compounds (I) and (II) with a crosslinking compound.

According to a preferred embodiment of the present invention, the functional group V may be a functional group of the type discussed above as group X.

According to another preferred embodiment, either functional group X or functional group V is a thio group and functional group V or functional group X is preferably selected from the group consisting of

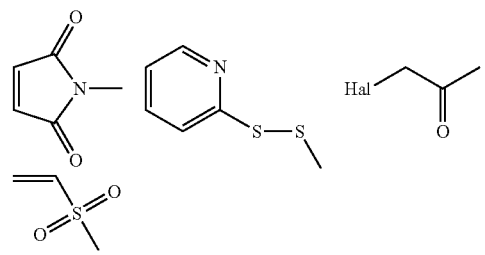

wherein Hal is Cl, Br, or I, preferably Br or I.

According to yet another preferred embodiment, either functional group X or functional group V is selected from the group consisting of an activated ester as described above or a carboxy group which is optionally transformed into an activated ester. In this particular case, the functional group V or the functional group X, respectively, comprises the chemical structure —NH—.

Therefore, the crosslinking compound is a compound having at least two functional groups which are the same or different. In the case of two functional group, the crosslinking compound may be homo-bifunctional or hetero-bifunctional. A homo-bifunctional crosslinking compound, e.g., provides the possibility to form a bridge between the reaction product of compounds (I) with (II) and a second further compound, the reaction product and the further compound having the same type of functional groups. A hetero-bifunctional crosslinking compound, e.g., provides the possibility to form a bridge between the reaction product of compounds (I) with (II) and a second further compound, the reaction product and the further compound having functional groups which are not capable of reacting with each other.

The at least two functional groups of the crosslinking compound may be linked directly together or may be separated by a linear or branched alkyl or cycloalkyl or aryl or aralkyl or arylcycloalkyl or alkaryl or cycloalkylaryl group, wherein these groups may comprise at least one heteroatom such as N, O, S, and wherein these groups may be suitably substituted. The length of the group separating the at least two functional groups of the crosslinking compound may be adapted to the specific needs. Generally, the separating group has from 1 to 60, preferably from 1 to 40, more preferably from 1 to 20, more preferably from 1 to 10, more preferably from 5 to 10 carbon atoms. If heteroatoms are present, the separating group comprises generally from 1 to 20, preferably from 1 to 8 and especially preferably from 1 to 4 heteroatoms. According to an even more preferred embodiment, the separating group is an alkyl or aralkyl chain of from 1 to 20 carbon atoms. Moreover, the crosslinking compound may further comprise at least one cleavage site as discussed above with regard to compound (II).

Other, examples of crosslinking compounds which are to be mentioned in the context of the present invention may be categorized, e.g., according to the following list:

| Type of crosslinking compound | Functional group, capable of being reacted with a second further compound, preferably a polypeptide | Functional group V |
| --- | --- | --- |
| A | Hydrazide (aldehyde-reactive) | Maleimido (SH-reactive |
| B | Hydrazide (aldeyde-reactive) | Pydridydithio (SH-reactive) |
| C | Iodoalkyl (SH-reactive) | N-succinimide ester (amine-reactive) |
| D | Bromoalkyl (SH-reactive) | N-succinimide ester (amine-reactive) |
| E | Maleimido (SH-reactive) | N-succinimide ester (amine-reactive) |
| F | Pydridyldithio (SH-reactive) | N-succinimide ester (amine-reactive) |
| G | Vinylsulfone (SH-reactive) | N-succinimide ester (amine-reactive) |

In Table 1 at the end of the present description, some preferred examples of crosslinking compounds are listed.

In case the at least one further compound, e.g. the crosslinking compound, comprises one or more chiral centers, the at least one further compound may be present in R conformation or in S conformation or as racemic compound with respect to each chiral center.

The term "polypeptide" as used in the context of the present invention refers to a compound which comprises at least 2 amino acids which are linked via a peptide bond, i.e. a bond with structure —(C=O)—NH—. The polypeptide may be a naturally occurring compound or a polypeptide which does not occur naturally, the latter comprising naturally occurring amino acids and/or at least one amino acid which does not naturally occur. The backbone of the polypeptide, the polypeptide chain, may be further substituted with at least one suitable substituent thus having at least one side-chain. The at least one functional group Y may be part of the polypeptide backbone or of at least one substituent of the polypeptide backbone wherein embodiments are possible comprising at least one functional group being part of the polypeptide backbone and at least one functional group being part of at least one substituent of the polypeptide backbone.

As far as the polypeptide is concerned, there exist no restrictions, given that the polypeptide comprises at least one functional group Y. Said functional group Y may be linked directly to the polypeptide backbone or be part of a side-chain of the backbone. Either side-chain or functional group Y or both may be part of a naturally occurring polypeptide or may be introduced into a naturally occurring polypeptide or into a polypeptide which, at least partially, does not occur naturally, prior to the reaction with the functional group X.

Moreover, the polypeptide can be, at least partly, of any human or animal source. In a preferred embodiment, the polypeptide is of human source.

The polypeptide may be a cytokine, especially erythropoietin, an antithrombin (AT) such as AT III, an interleukin, especially interleukin-2, IFN-beta, IFN-alpha, G-CSF, CSF, interleukin-6 and therapeutic antibodies.

According to a preferred embodiment, the polypeptide is an antithrombin (AT), preferably AT III (Levy J H, Weisinger A, Ziomek C A, Echelard Y, Recombinant Antithrombin: Production and Role in Cardiovascular Disorder, Seminars in Thrombosis and Hemostasis 27, 4 (2001) 405-416; Edmunds T, Van Patten S M, Pollock J, Hanson E, Bernasconi R, Higgins E, Manavalan P, Ziomek C, Meade H, McPherson J, Cole E S, Transgenically Produced Human Antithrombin: Structural and Functional Comparison to Human Plasma-Derived Antithrombin, Blood 91, 12 (1998) 4661-4671; Minnema M C, Chang A C K, Jansen P M, Lubbers Y T P, Pratt B M, Whittaker B G, Taylor F B, Hack C E, Friedman B, Recombinant human antithrombin III improves survival and attenuates inflammatory responses in baboons lethally challenged with *Escherichia coli*, Blood 95, 4 (2000) 1117-1123; Van Patten S M, Hanson E H, Bernasconi R, Zhang K., Manavaln P, Cole E S, McPherson J M, Edmunds T, Oxidation of Methionine Residues in Antithrombin, J. Biol. Chemistry 274, 15 (1999) 10268-10276).

According to another preferred embodiment, the polypeptide is human IFN-beta, in particular IFN-beta 1a (cf. Avonex®, REBIF®) and IFN-beta 1b (cf. BETASERON®).

A further preferred polypeptide is human G-CSF (granulocyte colony stimulating factor). See, e.g., Nagata et al., The chromosomal gene structure and two mRNAs for human granulocyte, colony-stimulating factor, EMBO J. 5: 575-581, 1986; Souza et al., Recombinant human granulocyte colony-stimulating factor: effects on normal and leukemic myeloid cells, Science 232 (1986) 61-65; and Herman et al., Characterization, formulation, and stability of Neupogen® (Filgrastim), a recombinant human granulocyte-colony stimulating factor, in: Formulalion, characterization, and stability of protein drugs, Rodney Pearlman and Y. John Wang, eds., Plenum Press, New York, 1996, 303-328.

If a mixture of at least two different polypeptides is used, the at least two polypeptides may differ, e.g., in the molecular mass, the number and/or sequence of amino acids, different degrees of glycosilation, the number and/or chemical nature of the substituents or the number of polypeptide chains linked by suitable chemical bonds such as disulfide bridges.

According to a preferred embodiment of the present invention, the reaction product of compound (I) and compound (II), optionally further reacted with a crosslinking compound, is isolated, preferably according to at least one of the above-mentioned processes, and then reacted with a polypeptide having at least one functional group Y capable of being reacted with the at least one functional group X of the reaction product of compound (I) and compound (II), optionally further reacted with a crosslinking compound, to form at least one chemical linkage. Functional groups Y of polypeptides such as proteins are, e.g.,

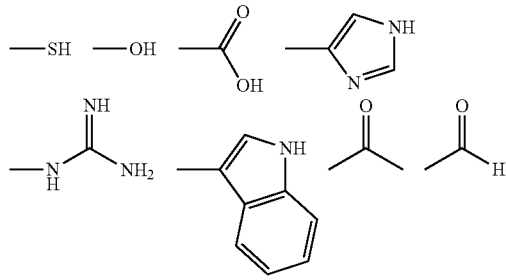

or a carbohydrate moiety which may be linked to the polypeptide by N-glycosylation or O-glycosylation.

In the context of the present invention, the term "carbohydrate moiety" refers to hydroxyaldehydes or hydroxyketones as well as to chemical modifications thereof (see Römpp Chemielexikon, Thieme Verlag Stuttgart, Germany, $9^{th}$ edition 1990, Volume 9, pages 2281-2285 and the literature cited therein). Furthermore, it also refers to derivatives of naturally occurring carbohydrate moieties like glucose, galactose, mannose, sialic acid and the like. The term also includes chemically oxidized, naturally occurring carbohydrate moieties. The structure of the oxidized carbohydrate moiety may be cyclic or linear.

The carbohydrate moiety may be linked directly to the polypeptide backbone. Preferably, the carbohydrate moiety is part of a carbohydrate side chain. More preferably, the carbohydrate moiety is the terminal moiety of the carbohydrate side chain.

In an even more preferred embodiment, the carbohydrate moiety is a galactose residue of the carbohydrate side chain, preferably the terminal galactose residue of the carbohydrate side chain. This galactose residue can be made available for reaction with the reaction product of compound (I) and compound (II) by removal of terminal sialic acids, followed by oxidation, as described hereinunder.

In a still further preferred embodiment, the reaction product of compound (I) and (II) is linked to a sialic acid residue of the carbohydrate side chains, preferably the terminal sialic acid residue of the carbohydrate side chain.

Oxidation of terminal carbohydrate moieties can be performed either chemically or enzymatically.

Methods for the chemical oxidation of carbohydrate moieties of polypeptides are known in the art and include the treatment with perjodate (Chamow et al., 1992, J. Biol. Chem., 267, 15916-15922).

By chemically oxidizing, it is in principle possible to oxidize any carbohydrate moiety, being terminally positioned or not. However, by choosing mild conditions (1 mM periodate, 0° C. in contrast to harsh conditions: 10 mM periodate 1 h at room temperature), it is possible to preferably oxidize the terminal sialic acid of a carbohydrate side chain.

Alternatively, the carbohydrate moiety may be oxidized enzymatically. Enzymes for the oxidation of the individual carbohydrate moieties are known in the art, e.g. in the case of galactose the enzyme is galactose oxidase. If it is intended to oxidize terminal galactose moieties, it will be eventually necessary to remove terminal sialic acids (partially or completely) if the polypeptide has been produced in cells capable of attaching sialic acids to carbohydrate chains, e.g. in mammalian cells or in cells which have been genetically modified to be capable of attaching sialic acids to carbohydrate chains. Chemical or enzymatic methods for the removal of sialic acids are known in the art (Chaplin and Kennedy (eds.), 1996, Carbohydrate Analysis: a practical approach, especially Chapter 5 Montreuill, Glycoproteins, pages 175-177; IRL Press Practical approach series (ISBN 0-947946-44-3)).

Therefore, the present invention also relates to a method as described above wherein the reaction product of compound (I) and compound (II) is reacted with the polypeptide via an oxidized carbohydrate moiety comprised in the polypeptide.

According to another preferred embodiment of the present invention, the functional group of the polypeptide is the thio group. Therefore, the reaction product of compound (I) and (II) may be linked to the polypeptide via a thioether group wherein the S atom can be derived from any thio group comprised in the polypeptide.

The thio group may be present in the polypeptide as such. Moreover, it is possible to introduce a thio group into the polypeptide according to a suitable method. Among others, chemical methods may be mentioned. If a disulfide bridge is present in the polypeptide, it is possible to reduce the —S—S— structure to get a thio group. It is also possible to transform an amino group present in the polypeptide into a SH group by reaction the polypeptide via the amino group with a compound which has at least two different functional groups, one of which is capable of being reacted with the amino group and the other is an SH group or a precursor of an SH group. This modification of an amino group may be regarded as an example where the protein is first reacted with a compound (L) which has at least two different functional groups, one of which is capable of being reacted with the amino group and the other is an SH group, and the resulting reaction product is then reacted with, e.g., a HAS derivative comprising HAS and a compound (D), said derivative comprising a functional group being capable of reacting with the SH group. It is also possible to introduce an SH group by mutation of the polypeptide such as by introducing a cystein or a suitable SH functional amino acid into the polypeptide or such as removing a cystein from the polypeptide so as to disable another cystein in the polypeptide to form ε disulfide bridge.

In the context of this embodiment, it is particularly preferred to react the polypeptide with a reaction product which results from the reaction of the reaction product of compounds (I) and (II) with a crosslinking compound.

Therefore, the present invention also relates to a method as described above wherein the reaction product of compound (I) and compound (II) is reacted with a crosslinking compound and the resulting reaction product is further is reacted with the polypeptide via an oxidized carbohydrate moiety and/or a thio group comprised in the polypeptide.

As an especially preferred polypeptide, erythropoietin (EPO) is used.

Therefore, the present invention also relates to a method as described above wherein the polypeptide is erythropoietin.

The EPO can be of any human (see e.g. Inoue, Wada, Takeuchi, 1994, An improved method for the purification of human erythropoietin with high in vivo activity from the urine of anemic patients, Biol. Pharm. Bull. 17(2), 180-4; Miyake, Kung, Goldwasser, 1977, Purification of human erythropoietin., J. Biol. Chem., 252(15), 5558-64) or another mammalian source and can be obtained by purification from naturally occurring sources like human kidney, embryonic human liver or animal, preferably monkey kidney. Furthermore, the expression "erythropoietin" or "EPO" encompasses also an EPO variant wherein one or more amino acids (e.g. 1 to 25, preferably 1 to 10, more preferred 1 to 5, most preferred 1 or 2) have been exchanged by another amino acid and which exhibits erythropoietic activity (see e.g. EP 640 619 B1). The measurement of erythropoietic activity is described in the art (for measurement of activity in vitro see e.g. Fibi et al., 1991, Blood, 77, 1203 ff; Kitamura et al, 1989, J. Cell Phys., 140, 323-334; for measurement of EPO activity in vivo see Ph. Eur. 2001, 911-917; Ph. Eur. 2000, 1316 Erythropoietin solution concentrate, 780-785; European Pharmacopoeia (1996/2000); European Pharmacopoeia, 1996, Erythropoietin concentrated solution, Pharmaeuropa., 8, 371-377; Fibi, Hermentin, Pauly, Lauffer, Zettlmeissl., 1995, N- and O-glycosylation muteins of recombinant human erythropoietin secreted from BHK-21 cells, Blood, 85(5), 1229-36; (EPO and modified EPO forms were injected into female NMRI mice (equal amounts of protein 50 ng/mouse) at day 1, 2 and 3 blood samples were taken at day 4 and reticulocytes were determined)). Further publications where tests for the measurement of the activity of EPO are described Barbone, Aparicio, Anderson, Natarajan, Ritchie, 1994, Reticulocytes measurements as a bioassay for erythropoietin, J. Pharm. Biomed. Anal., 12(4), 515-22; Bowen, Culligan, Beguin, Kendall, Villis, 1994, Estimation of effective and total erythropoiesis in myelodysplasia using serum transferrin receptor and erythropoietin concentrations, with automated reticulocyte parameters, Leukemi, 8(1), 151-5; Delorme, Lorenzini, Giffin, Martin, Jacobsen, Boone, Elliott, 1992, Role of glycosylation on the secretion and biological activity of erythropoietin, Biochemistry, 31(41), 9871-6; Higuchi, Oheda, Kuboniwa, Tomonoh, Shimonaka, Ochi, 1992; Role of sugar chains in the expression of the biological activity of human erythropoietin, J. Biol. Chem., 267(11), 7703-9; Yamaguchi, Akai, Kawanishi, Ueda, Masuda, Sasaki, 1991, effects of site-directed removal of N-glycosylation sites in human erythropoietin on its production and biological properties, J. Biol. Chem., 266(30), 20434-9; Takeuchi, Inoue, Strickland, Kubota, Wada, Shimizu, Hoshi, Kozutsumi, Takasaki, Kobata, 1989, Relationship between sugar chain structure and biological activity of recombinant human erythropoietin produced in Chinese hamster ovary cells, Proc. Natl. Acad. Sci. USA, 85(20), 7819-22; Kurtz, Eckardt, 1989, Assay methods for erythropoietin, Nephron., 51(1), 11-4 (German); Zucali, Sulkowski, 1985, Purification of human urinary erythropoietin on controlled-pore glass and silicic acid, Exp. Hematol., 13(3), 833-7; Krystal, 1983, Physical and biological characterization of erythroblast enhancing factor (EEF), a late acting erythropoietic stimulator in serum distinct from erythropoietin, Exp. Hematol., 11(1), 18-31.

Preferably, the EPO is recombinantly produced. This includes the production in eukaryotic or prokaryotic cells, preferably mammalian, insect, yeast, bacterial cells or in any other cell type which is convenient for the recombinant production of EPO. Furthermore, the EPO may be expressed in transgenic animals (e.g. in body fluids like milk, blood, etc.), in eggs of transgenic birds, especially poultry, preferred chicken, or in transgenic plants.

The recombinant production of a polypeptide is known in the art. In general, this includes the transfection of host cells with an appropriate expression vector, the cultivation of the host cells under conditions which enable the production of the polypeptide and the purification of the polypeptide from the host cells. For detailed information see e.g. Krystal, Pankratz, Farber, Smart, 1986, Purification of human erythropoietin to homogeneity by a rapid five-step procedure, Blood, 67(1), 71-9; Quelle, Caslake, Burkert, Wojchowski, 1989, High-level expression and purification of a recombinant human erythropoietin produced using a baculovirus vector, Blood, 74(2), 652-7; EP 640 619 B1 and EP 668 351 B1.

In a preferred embodiment, the EPO has the amino acid sequence of human EPO (see EP 148 605 B2).

The EPO may comprise one or more carbohydrate side chains, preferably 1 to 12, more preferably 1 to 9, even more preferably 1 to 6 and particularly 1 to 4, especially preferably 4 carbohydrate side chains, attached to the EPO via N- and/or O-linked glycosylation, i.e. the EPO is glycosylated. Usually, when EPO is produced in eukaryotic cells, the polypeptide is posttranslationally glycosylated. Consequently, the carbohydrate side chains may have been attached to the EPO during biosynthesis in mammalian, especially human, insect or yeast cells. The structure and properties of glycosylated EPO have been extensively studied in the art (see EP 428 267 B1; EP 640 619 B1; Rush, Derby, Smith, Merry, Rogers, Rohde, Katta, 1995, Microheterogeneity of erythropoietin carbohydrate structure, Anal Chem., 67(8), 1442-52; Takeuchi, Kobata, 1991, Structures and functional roles of the sugar chains of human erythropoietins, Glycobiology, 1(4), 337-46 (Review).

Therefore, the hydroxyalkyl starch derivative according to the present invention may comprise at least one, preferably 1 to 12, more preferably 1 to 9, even more preferably 1 to 6 and particularly preferably 1 to 4 HAS molecules per EPO molecule. The number of HAS-molecules per EPO molecule can be determined by quantitative carbohydrate compositional analysis using GC-MS after hydrolysis of the product and derivatisation of the resulting monosaccharides (see Chaplin and Kennedy (eds.), 1986, Carbohydrate Analysis: a practical approach, IRL Press Practical approach series (ISBN 0-947946-44-3), especially Chapter 1, Monosaccharides, page 1-36; Chapter 2, Oligosaccharides, page 37-53, Chapter 3, Neutral Polysaccharides, page 55-96).

According to an especially preferred embodiment of the present invention, the carbohydrate moiety linked to EPO, is part of a carbohydrate side chain. More preferably, the carbohydrate moiety is the terminal moiety of the carbohydrate side chain. In an even more preferred embodiment, the carbohydrate moiety is a galactose residue of the carbohydrate side chain, preferably the terminal galactose residue of the carbohydrate side chain. This galactose residue can be made available for reaction with the reaction product of compound (I) and compound (II) by removal of terminal sialic acids, followed by oxidation, as described hereinunder. In a further preferred embodiment, the reaction product of compound (I) and (II) is linked to a sialic acid residue of the carbohydrate side chains, preferably the terminal sialic acid residue of the carbohydrate side chain. The sialic acid is oxidized as described herein.

Particularly preferably this galactose residue is made available for reaction with the reaction product of compounds (I) and (II) or with the reaction product of the reaction of the reaction product of compounds (I) and (II) and a crosslinking compound via functional group X by removal of terminal sialic acid followed by oxidation.

As mentioned above, the reaction product of compound (I) and compound (II), optionally reacted with a crosslinking compound, may be reacted with a thio group comprised in EPO.

It is also possible to react the reaction product of compound (I) and compound (II), optionally reacted with a crosslinking compound, with a thio group as well as with a carbohydrate moiety, each of them comprised in the at least one further compound, preferably a polypeptide, more preferably erythropoietin.

According to a preferred embodiment, this SH group may be linked to a preferably oxidized carbohydrate moiety, e.g. by using a hydroxylamine derivative, e.g. 2-(aminooxy)ethylmercaptan hydrochloride (Bauer L. et al., 1965, J. Org. Chem., 30, 949) or by using a hydrazide derivative, e.g. thioglycolic acid hydrazide (Whitesides et al., 1977, J. Org. Chem., 42, 332.)

According to a further preferred embodiment, the thio group is preferably introduced in an oxidized carbohydrate moiety of EPO, more preferably an oxidized carbohydrate moiety which is part of a carbohydrate side chain of EPO.

Preferably, the thio group is derived from a naturally occurring cysteine or from an added cysteine. More preferably, the EPO has the amino acid sequence of human EPO and the naturally occurring cysteines are cysteine 29 and/or 33. In a more preferred embodiment, the reaction product of compound (I) and compound (II), optionally reacted with a crosslinking compound, is reacted with cysteine 29 whereas cysteine 33 is replaced by another amino acid. Alternatively, the reaction product of compound (I) and compound (II), optionally reacted with a crosslinking compound, is reacted with cysteine 33 whereas cysteine 29 is replaced by another amino acid.

In the context of the present invention, the term "added cysteines" indicates that the polypeptides, preferably EPO, comprise a cysteine residue which is not present in the wild-type polypeptide.

In the context of this aspect of the invention, the cysteine may be an additional amino acid added at the N- or C-terminal end of EPO.

Furthermore, the added cysteine may have been added by replacing a naturally occurring amino acid by cysteine or a suitably substituted cysteine. Preferably, in the context of this aspect of the invention, the EPO is human EPO and the replaced amino acid residue is serine 126.

The reaction conditions of the reaction of the reaction product of compounds (I) and (II), optionally reacted with a crosslinking compound, with the at least one further compound may be adapted to the specific needs of the respective reaction, such as in the case the at least one further compound is a polypeptide or in the case the at least one further compound is a crosslinking compound or in the case the at least one further compound is a reaction product of a crosslinking compound and a polypeptide. As buffer compounds, at least one of the above-mentioned compounds may be preferably used. As solvent or mixture of solvents, at least one of the above-mentioned solvents may be preferably used. Isolation and/or after-treatment may be carried out, wherein preferred methods are selected from the methods discussed above.

If the reaction product of compound (I) and compound (II) is, for example, further reacted with a polypeptide as further compound, preferably EPO, water is preferably used as solvent for the reaction. Additionally to water, at least one further solvent may be present. As preferred possible further solvent, DMSO, DMF, methanol or ethanol may be mentioned.

Therefore, the present invention also relates to a method as described above wherein the reaction of the reaction product of compound (I) and compound (II) with a polypeptide, preferably EPO, is carried out in an aqueous system.

As far as the temperatures which are applied during this reaction are concerned, no specific limitations exist given that the reaction results in the desired hydroxyalkyl starch derivative comprising the reaction product of compounds (I) and (II) reacted with the polypeptide via the at least one functional group X. The temperature of the reaction is preferably in the range of from 4 to 37° C., more preferably in the range of from 10 to 30° C. especially preferably in the range of from 15 to 25° C.

Therefore, the present invention also relates to a method as described above wherein the reaction of the reaction product of compound (I) and compound (II) with the polypeptide is carried out at a temperature of from 4 to 37° C.

During the course of the reaction the temperature may be varied, preferably in the above-given ranges, or held essentially constant.

The reaction time for reaction of the reaction product of compound (I) and compound (II) with the polypeptide may be adapted to the specific needs and is generally in the range of from 0.5 to 48 h, preferably in the range of from 2 to 24 h and especially preferably in the range of from 10 to 20 h.

The pH value for the reaction of the reaction product of compound (I) and compound (II) with the polypeptide may be adapted to the specific needs such as the chemical nature of the reactants.

If, e.g., the reaction product of compound (I) and (II) is reacted with a further compound via the reaction of a functional group X which is a hydroxylamino group —O—$NH_2$ with at least one aldehyd group which is comprised in the polypeptide, the pH is preferably in the range of from 4.5 to 6, more preferably at about 5.5.

If the reaction product of compound (I) and compound (II) is, for example, further reacted with a crosslinking compound as further compound, preferably EPO, water is preferably used as solvent for the reaction. Additionally to water, at least one further solvent may be present. As preferred possible further solvent, DMSO, DMF, methanol or ethanol may be mentioned.

Therefore, the present invention also relates to a method as described above wherein the reaction of the reaction product of compound (I) and compound (II) with a crosslinking compound is carried out in an aqueous system.

As far as the temperatures which are applied during this reaction are concerned, no specific limitations exist given that the reaction results in the desired hydroxyalkyl starch derivative comprising the reaction product of compounds (I) and (II) reacted with the crosslinking compound via the at least one functional group X. The temperature of the reaction is preferably in the range of from 4 to 37° C., more preferably in the range of from 10 to 30° C. especially preferably in the range of from 15 to 25° C.

Therefore, the present invention also relates to a method as described above wherein the reaction of the reaction product of compound (I) and compound (II) with the crosslinking compound is carried out at a temperature of from 4 to 37° C.

During the course of the reaction the temperature may be varied, preferably in the above-given ranges, or held essentially constant.

The reaction time for reaction of the reaction product of compound (I) and compound (II) with the crosslinking compound may be adapted to the specific needs and is generally in the range of from 10 min to 10 h, preferably of from 20 min to 5 h and more preferably of from 30 min to 2 h.

The pH value for the reaction of the reaction product of compound (I) and compound (II) with the crosslinking compound may be adapted to the specific needs such as the chemical nature of the reactants.

If, e.g., the reaction product of compound (I) and (II) is reacted with a crosslinking compound which is a crosslinking compound via the functional group X which is comprised in the reaction product of compound (I) and (II) and is an amino group —$NH_2$, the pH is preferably in the range of from 7 to 8.5, more preferably at about 7.2.

If the reaction product of the reaction of the reaction product of compounds (I) and (II), and a crosslinking compound is, for example, further reacted with a polypeptide, preferably EPO, water is preferably used as solvent for the reaction. Additionally to water, at least one further solvent may be present. As preferred possible further solvent, DMSO, DMF, methanol or ethanol may be mentioned.

Therefore, the present invention also relates to a method as described above wherein the reaction of the reaction product of the compound (I) and compound (II) which is further with reacted with a crosslinking compound, with a polypeptide is carried out in an aqueous system.

As far as the temperatures which are applied during this reaction are concerned, no specific limitations exist given that the reaction results in the desired hydroxyalkyl starch derivative comprising the reaction product of compounds (I) and (II), reacted with a crosslinking compound and further reacted with a polypeptide via the at least one functional group X comprised in the crosslinking compound. The temperature of the reaction is preferably in the range of from 4 to 37° C., more preferably in the range of from 10 to 30° C. especially preferably in the range of from 15 to 25° C.

Therefore, the present invention also relates to a method as described above wherein the reaction of the reaction product of compound (I) and compound (II) which is further reacted with a crosslinking compound, with the polypeptide is carried out at a temperature of from 4 to 37° C.

During the course of the reaction the temperature may be varied, preferably in the above-given ranges, or held essentially constant.

The reaction time for the reaction of the reaction product of compound (I) and compound (II) which is further reacted with a crosslinking compound, with the polypeptide may be adapted to the specific needs and is generally in the range of from 0.5 to 48 h, preferably in the range of from 2 to 24 h and especially preferably in the range of from 10 to 20 h.

The pH value for the reaction of the reaction product of compound (I) and compound (II) which is further reacted with a crosslinking compound, with the polypeptide may be adapted to the specific needs such as the chemical nature of the reactants.

If, e.g., the reaction product of compound (I) and (II) is which is further reacted with a crosslinking compound, is reacted with a polypeptide via the functional group X which is comprised in the crosslinking compound and is an amino group —$NH_2$, the pH is preferably in the range of from 7 to 8.5, more preferably at about 7.2.

The suitable pH value of the reaction mixture may be adjusted in each case by adding at least one suitable buffer. Among the preferred buffers, sodium acetate buffer, sodium phosphate buffer, or borate buffers may be mentioned.

The reaction product resulting from the reaction of the reaction product of compound (I) and compound (II) with the at least one further compound, the at least one further compound being either a polypeptide or a crosslinking compound, and the reaction product further comprising the compounds resulting from the reactions of compound (I), compound (II), a crosslinking compound and a polypeptide, may be isolated from the reaction mixture by at least one suitable method and subjected to at least one further treatment such as at least an after-treatment such as dialysis and/or lyophilization.

Once the above-mentioned reaction product is formed, it may be isolated from the reaction mixture by at least one suitable method.

Isolation of the reaction product may be carried out by a suitable process which may comprise one or more steps.

According to a preferred embodiment of the present invention, where the reaction product does not comprise a polypeptide, the reaction product is first separated off the reaction mixture or the mixture of the reaction mixture by preferably centrifugal filtration. In a second step, the separated reaction product may be subjected to a further treatment such as an after-treatment like dialysis and/or lyophilisation. According to an even more preferred embodiment, the separated reaction product is first dialysed, preferably against water, and then lyophilized until the solvent content of the reaction product is sufficiently low according to the desired specifications of the product.

According to another embodiment of the present invention where the reaction product comprises the polypeptide, the reaction product is preferably isolated as described in Example 7.8.

According to a further embodiment of the present invention, compound (II) is reacted with a further compound prior to the reaction with compound (I), i.e. a derivate of compound (II) is produced by the reaction of compound (II) via the at least one functional group X with at least one further compound comprising at least one functional group Y, as described above, prior to the reaction with compound (I).

If compound (II) is first reacted with a further compound, preferably a polypeptide, more preferably EPO, water is preferably used as solvent for the reaction. Additionally to water, at least one further solvent may be present. As preferred possible further solvent, DMSO, DMF, methanol and ethanol may be mentioned.

Therefore, the present invention also relates to a method as described above wherein the reaction of compound (II), prior to the reaction with compound (I), with a further compound, preferably a polypeptide, even more preferably EPO, is carried out in an aqueous system.

As far as the temperatures which are applied during the reaction are concerned, no specific limitations exist given that the reaction results in the desired derivative of compound (II) comprising the reaction product of compound (II) reacted with at least one further compound via the at least one functional group X, preferably a polypeptide, more preferably EPO. The temperature of the reaction are preferably in the range of from 4 to 37° C., more preferably in the range of from 10 to 30° C. especially preferably in the range of from 15 to 25° C.

Therefore, the present invention also relates to a method as described above wherein the reaction compound (II) with the at least one further compound is carried out at a temperature of from 4 to 37° C.

During the course of the reaction the temperature may be varied, preferably in the above-given ranges, or held essentially constant.

The reaction time, the pH value for reaction of compound (II) with the at least one further compound may be adapted to the specific needs such as the chemical nature of the reactants. The suitable pH value of the reaction mixture may be adjusted by adding at least one suitable buffer. Among the preferred buffers, acetate, phosphate, or borate buffers such as sodium acetate, sodium phosphate, or sodium borate buffers may be mentioned.

The reaction product resulting from the reaction of compound (II) with the at least one further compound may be isolated from the reaction mixture by at least one suitable method and subjected to at least one further treatment such as at least an after-treatment such as dialysis and/or lyophilization.

Once the reaction product of reaction compound (II) with the at least one further compound is formed, it may be isolated from the reaction mixture by at least one suitable method.

Isolation of the reaction product may be carried out by a suitable process which may comprise one or more steps as already described above.

If desired and/or necessary, the NH group bridging R' and R" of compound (II) may be protected with a suitable protecting group prior to the reaction of compound (II) with the at least one further compound. As protecting group, one of the above-mentioned protecting groups may be used. Prior to the reaction of the reaction product of compound (II) and the at least one further compound such as a polypeptide, preferably EPO, with compound (I), the protecting group is removed by a at least one suitable method.

If compound (II) is first reacted with a crosslinking compound or a reaction product of a crosslinking compound and a polypeptide, all reaction conditions may be adjusted to the specific needs of these reactions. Among others, the above-mentioned buffer systems and/or solvents may be used.

In a second step, the reaction product of the reaction of compound (II) with the at least one further compound is reacted with compound (I).

For this reaction, all reaction conditions may be adjusted to the specific needs of these reactions. Among others, the above-mentioned buffer systems and/or solvents may be used.

The reaction product resulting from the reaction of the reaction product of compound (II) and the at least one further compound with compound (I) may be isolated from the respective reaction mixture by at least one suitable method and subjected to at least one further treatment such as at least an after-treatment such as dialysis and/or lyophilization. In this context, every suitable method described above may be used.

Generally, isolation of the HAS-polypeptide conjugate, either with or without crosslinking compound, can be performed by using known procedures for the purification of natural and recombinant polypeptides such as size exclusion chromatography, ion-exchange chromatography, RP-HPLC, hydroxyapatite chromatography, hydrophobic interaction chromatography or combinations of at least two methods thereof.

The covalent attachment of HAS to the polypeptide can be verified by carbohydrate compositional analysis after hydrolysis of the modified protein.

Demonstration of HAS modification at N-linked oligosaccharides of the polypeptide can be accomplished by removal of the HAS modified N-glycans and observation of the predicted shift to higher mobility in SDS-PAGE+/− Western Blotting analysis.

HAS modification of the polypeptide at cysteine residues can be demonstrated by the failure to detect the corresponding proteolytic Cys-peptide in RP-HPLC and MALDI/TOF-MS in the proteolytic fragments of the HAS-modified product (Zhou et al., 1998, Application of capillary electrophoresis, liquid chromatography, electrospray-mass spectrometry and matrix-assisted laserdesorption/ionization—time of flight—mass spectrometry to the characterization of recombinant human erythropoietin, Electrophoresis, 19(13), 2348-55). The isolation of the HAS-containing fraction after proteolytic digestion of the Cys-modified polypeptide enables the verification in this fraction of the corresponding peptide by conventional amino acid compositional analysis.

All embodiments disclosed above with respect of the HAS-polypeptide of the invention concerning properties of the polypeptide or HAS apply also to the method of the invention for the production of a HAS-polypeptide conjugate. Furthermore, all embodiments disclosed above with respect to HAS-EPO or the preparation thereof which relate to peptides in general or to HAS apply also to the method of the invention for the production of a HAS-polypeptide conjugate.

According to an especially preferred embodiment of the present invention hydroxyethyl starch is reacted with a compound (II), preferably selected from the homo- and heterobifunctional compounds described above, and the resulting reaction product is reacted with a glycoprotein, preferably erythropoietin, preferably with the oxidized terminal carbohydrate moiety of a EPO carbohydrate side chain.

According to another especially preferred embodiment of the present invention hydroxyethyl starch is reacted with a compound (II), preferably selected from the homo- and heterobifunctional compounds described above, to give a first hydroxyethyl starch derivative. This first hydroxyethyl starch derivative is subsequently reacted with a crosslinking compound to give a second hydroxyethyl starch derivative. This second hydroxyethyl starch derivative is subsequently reacted with a glycoprotein, preferably erythropoietin, preferably with a —SH group comprised in the glycoprotein, to give a third hydroxyethyl starch derivative. Preferably, the crosslinking compound is a heterobifunctional compound. More preferably, the crosslinking compound is reacted with a functional group comprising the structure —NH— which is comprised in the first hydroxyethyl starch derivative. More preferably, this functional group is —NH$_2$.

One advantage of the present invention is that it is not necessary to use toxicologically critical solvents in at least one reaction step, preferably all reaction steps, the reaction step involved and thus, is not necessary to remove these solvents after the production process in order to avoid the contamination of the products with the solvent. Furthermore, it is not necessary to perform additional quality controls with respect to residual toxicologically critical solvents. If organic solvents, preferably in addition to water, are used, it is preferred to use toxicologically uncritical solvents such as ethanol and/or propylenglycol.

Another advantage of the present invention is that irreversible or reversible structural changes are avoided in the steps where an aqueous system is used as solvent which are otherwise induced by organic solvents. Consequently, polypeptide derivatives obtained according to the method of the invention are different from those prepared in organic solvents such as DMSO.

Furthermore, it has been surprisingly observed that the conjugation of HAS to polypeptides such as EPO in an aqueous solution minimizes or avoids side reactions. Consequently, this embodiment of the method of the invention leads to improved hydroxyallyl starch products with great purity.

According to another aspect, the present invention also relates to the hydroxy alkyl starch derivative, obtainable by a process comprising reacting hydroxyalkyl starch (HAS) of formula (I)

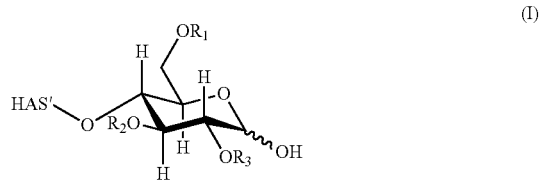

(I)

at its reducing end which is not oxidized prior to said reaction, with a compound of formula (II)

wherein $R_1$, $R_2$ and $R_3$ are independently hydrogen or a linear or branched hydroxyalkyl group, and wherein either R' or R" or R' and R" comprise at least one functional group X capable of being reacted with at least one other compound prior to or after the reaction of (I) and (II).

As already described above in the context of the methods of the present invention, O-[2-(2-aminooxy-ethoxy)-ethyl]-hydroxyl amine is used as a preferred compound (II), and hydroxyethyl starch is used as a preferred hydroxyalkyl starch.

Therefore, the present invention also relates to a hydroxyalkyl starch derivative obtainable by a method wherein hydroxyethyl starch is reacted via its reducing end with O-[2-(2-aminooxy-ethoxy)-ethyl]-hydroxyl amine.

Depending on the respective reaction conditions, the solvent or solvent mixture used and/or the residues R' and/or R" it is possible that the hydroxyalkyl starch derivate obtainable by the method or methods described above may have the following constitutions (IIIa):

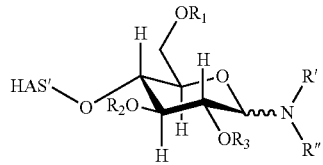

Therefore, the present invention also relates to a hydroxyalkyl starch derivative as described above having a constitution according to formula (IIIa).

It is also possible that, e.g. in the case where R' is hydrogen that the hydroxyalkyl starch derivate obtainable by the method or methods described above may have the following constitutions (IIIa) or (IIIa) where (IIIa) and (IIIb) may be both present in the reaction mixture having a certain equilibrium distribution:

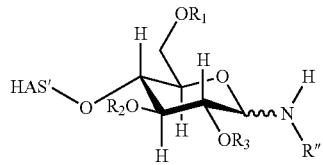

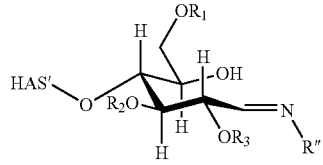

Therefore, the present invention also relates to a hydroxyalkyl starch derivative as described above having a constitution according to formula (IIIb).

Moreover, the present invention also relates to a hydroxyalkyl starch derivative as described above being present in a mixture of constitutions according to formulae (IIIa) and (IIIb).

Depending on the reaction conditions and/or the chemical nature of compound (II) used for the reaction, the compounds according to formula (IIIa) may be present with the N atom in equatorial or axial position where also a mixture of both forms may be present having a certain equilibrium distribution.

Depending on the reaction conditions and/or the chemical nature of compound (II) used for the reaction, the compounds according to formula (IIIb) may be present with the C—N double bond in E or Z conformation where also a mixture of both forms may be present having a certain equilibrium distribution.

In some cases it may be desirable to stabilize the compound according to formula (IIIa). This is especially the case where the compound according to formula (IIIa) is produced and/or used in an aqueous solution. As stabilizing method, acylation of the compound according to formula (IIIa) is particularly preferred, especially in the case where R' is hydrogen. As acylation reagent, all suitable reagents may be used which result in the desired hydroxyalkyl starch derivative according to formula (IVa)

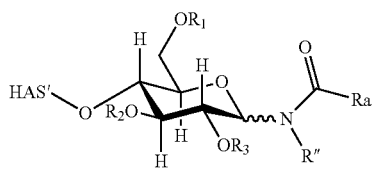

According to especially preferred embodiments of the present invention, the residue Ra being part of the acylation reagent is methyl. As acylation reagents, carboxylic acid anhydrides, carboxylic acid halides, and carboxylic acid active esters are preferably used.

Therefore, the present invention also relates to a hydroxyalkyl starch derivate obtainable by a method as described above wherein said derivative has a constitution according to formula (IVa).

The acylation is carried at a temperature in the range of from 0 to 30° C., preferably in the range of from 2 to 20° C. and especially preferably in the range of from 4 to 10° C.

In other cases it may be desirable to stabilize the compound according to formula (IIIb). This is especially the case where the compound according to formula (IIIb) is produced and/or used in an aqueous solution. As stabilizing method, reduction of the compound according to formula (IIIb) is particularly preferred, especially in the case where R' is hydrogen. As reduction reagent, all suitable reagents may be used which result in the desired hydroxyalkyl starch derivative according to formula (IVb)

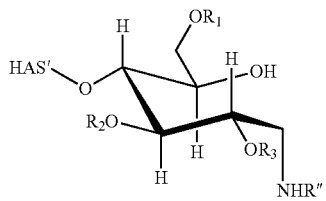

According to especially preferred embodiments of the present invention, as reduction reagents boro hydrides such as $NaCNBH_3$ or $NaBH_4$ are used.

Therefore, the present invention also relates to a hydroxyallyl starch derivate obtainable by a method as described above wherein said derivative has a constitution according to formula (IVb).

The reduction is carried at a temperature in the range of from 4 to 100° C., preferably in the range of from 10 to 90° C. and especially preferably in the range of from 25 to 80° C.

The present invention further relates to mixtures of compounds (IIIa) and (IIIb), (IVa) and (IVb), (IIIa) and (IVa), (IIIa) and (IVb), (IIIb) and (IVa), (IIIb) and (IVb), (IIIa) and (IIIb) and (IVa), (IIIa) and (IIIb) and (IVb), (IVa) and (IVb) and (IIIa), and (IVa) and (IVb) and (IIIb) wherein (IIIa) and/or (IVa) may be independently present in a conformation where the N atom in equatorial or axial position and/or wherein (IIIb) may be present with the C—N double bond in E or Z conformation.

According to one aspect of the present invention, compound (I) is reacted with compound (II) to give a first reaction product. Said first reaction product is then optionally stabilized according to at least one of the methods described above. The first, optionally stabilized reaction product is then reacted with at least one further compound via the reaction of at least one functional group X comprised in R" of the first reaction product with at least one functional group Y comprised in the at least one further compound, to give a second reaction product. Said second reaction product is then optionally stabilized according to at least one of the methods described above.

According to yet another aspect of the present invention, the at least one further compound is a polypeptide or a crosslinking compound or a reaction product of a crosslinking compound with a polypeptide. In case the at least one further compound is a polypeptide, the functional group Y is comprised in the polypeptide. In case the at least one further compound is a crosslinking compound, the functional group Y is comprised in the crosslinking compound and optionally also in the polypeptide. In case the at least one further compound is a reaction product of a crosslinking compound with a polypeptide, the functional group Y is comprised in the crosslinking compound.

According to a further aspect of the present invention, compound (II) is reacted with at least one further compound via the reaction of at least one functional group X comprised in R" of compound (II) with at least one functional group Y comprised in the at least one further compound to give a first reaction product. The at least one further compound is preferably a polypeptide or a crosslinking compound or a reaction product of a crosslinking compound with a polypeptide, as discussed above. Said first reaction product is then reacted with compound (I) via the reaction of the reducing end of compound (I) with the NH group of the first reaction product bridging the original residues R' and R" of compound (II) to give a second reaction product. Said second reaction product is then optionally stabilized according to at least one of the methods described above.

According to an especially preferred embodiment of the present invention, hydroxyethyl starch is used as compound (I), O-[2-(2-aminooxy-ethoxy)-ethyl]-hydroxyl amine is used as compound (II), and EPO having an oxidized terminal carbohydrate moiety of a carbohydrate side chain is used as further compound. More preferably, hydroxyethyl starch is reacted with O-[2-(2-aminooxy-ethoxy)-ethyl]-hydroxyl amine to give a first hydroxyethyl starch derivate, and that first derivative is further reacted with EPO having an oxidized terminal carbohydrate moiety of a carbohydrate side chain to give a second hydroxyethyl starch derivate. In this specific case, no stabilizing reaction whatsoever has to be carried out.

Therefore, the present invention also relates to a hydroxyalkyl starch derivative obtainable by a method wherein hydroxyethyl starch is reacted via its reducing end with O-[2-(2-aminooxy-ethoxy)-ethyl]-hydroxyl amine, and the reaction product is reacted with erythropoietin via the oxidized terminal carbohydrate moiety of a carbohydrate side chain of the erythropoietin.

According to yet another especially preferred embodiment of the present invention, hydroxyethyl starch is used as compound (I), O-[2-(2-aminooxy-ethoxy)-ethyl]-hydroxyl amine is used as compound (II), a heterobifunctional crosslinking compound having a maleimide group and a N-hydroxy succinimide active ester group, is used, and EPO having at least one —SH group (referred to as ThioEPO) is used as polypeptide. More preferably, hydroxyethyl starch is reacted with O-[2-(2-aminooxy-ethoxy)-ethyl]-hydroxyl amine to give a first hydroxyethyl starch derivate, that first derivative is further reacted with the N-hydroxy succinimide active ester group of the crosslinking compound to give a second derivative, and that second derivative is reacted via the maleimide group with the ThioEPO to give a third hydroxyethyl starch derivate.

The hydroxyalkyl starch derivative which in the following is referred to as HAS-EPO conjugate and which is formed by reaction of compound (I) with compound (II) and possibly a crosslinking compound and erythropoietin, has the advantage that it exhibits an improved biological stability when compared to the erythropoietin before conjugation. This is mainly due to the fact that this hydroxyalkyl starch derivative is less or even not recognized by the removal systems of the liver and kidney and therefore persists in the circulatory system for a longer period of time. Furthermore, since the HAS is attached site-specifically, the risk of destroying the in-vivo biological activity of EPO by conjugation of HAS to EPO is minimized.

The HAS-EPO conjugate of the invention may exhibit essentially the same in-vitro biological activity as recombinant native EPO, since the in-vitro biological activity only measures binding affinity to the EPO receptor. Methods for determining the in-vitro biological activity are known in the art.

Furthermore, the HAS-EPO exhibits a greater in-vivo activity than the EPO used as a starting material for conjugation (unconjugated EPO). Methods for determining the in vivo biological activity are known in the art.

The HAS-EPO conjugate may exhibit an in vivo activity of from 110% to 300%, preferably from 110% to 200%, more preferably from 110% to 180% or from 110 to 150%, most preferably from 110% to 140%, if the in-vivo activity of the unconjugated EPO is set as 100%.

Compared to the highly sialylated EPO of Amgen (see EP 428 267 B1), the HAS-EPO exhibits preferably at least 50%, more preferably at least 70%, even more preferably at least 85% or at least 95%, at least 150%, at least 200% or at least 300. % of the in vivo activity of the highly sialylated EPO if the in-vivo activity of highly sialylated EPO is set as 100%. Most preferably, it exhibits at least 95% of the in vivo activity of the highly sialylated EPO.

The high in-vivo biological activity of the HAS-EPO conjugate of the invention mainly results from the fact that the HAS-EPO conjugate remains longer in the circulation than the unconjugated EPO because it is less recognized by the removal systems of the liver and because renal clearance is reduced due to the higher molecular weight. Methods for the determination of the in-vivo half life time of EPO in the circulation are known in the art (Sytkowski, Lunn, Davis, Feldman, Siekman, 1998, Human erythropoietin dimers with markedly enhanced in vivo activity, Proc. Natl. Acad. Sci. USA, 95(3), 1184-8).

Consequently, it is a great advantage of the present invention that a HAS-EPO conjugate is provided which may be administered less frequently than the EPO preparations commercially available at present. While standard EPO preparations have to be administered at least every 3 days, the HAS-EPO conjugate of the invention is preferable administered twice a week, more preferably once a week.

Furthermore, the method of the invention has the advantage that an effective EPO derivative can be produced at reduced costs since the method does not comprise extensive and time consuming purification steps resulting in low final yield, e.g. it is not necessary to purify away under-sialylated EPO forms which are known to exhibit low or no in-vivo biological activity.

Furthermore, the present invention relates to a pharmaceutical composition comprising, in a therapeutically effective amount, the HAS-polypeptide conjugate, preferably the HAS-EPO conjugate, more preferably the HES-EPO conjugate of the present invention. In a preferred embodiment, the pharmaceutical composition comprises further at least one pharmaceutically acceptable diluent, adjuvant and/or carrier useful in erythropoietin therapy.

Therefore, the present invention also relates to a pharmaceutical composition comprising, in a therapeutically effective amount, a hydroxyalkyl starch derivative as described above wherein the reaction product of compound (I) with compound (II) is reacted via the at least one functional group X comprised in compound (II) with at least one further compound or wherein compound (II) is reacted via the at least one functional group X with at least one further compound prior to the reaction with compound (I) and wherein the at least one further compound is a polypeptide.

According to preferred embodiments of the present invention, the polypeptide, preferably erythropoietin is reacted with compound (II) or with the reaction product of compound (I) and compound (II) via a thio group or an oxidized carbohydrate moiety comprised in the polypeptide.

According to an even more preferred embodiment of the present invention, the polypeptide, preferably erythropoietin is reacted with compound (II) or with the reaction product of compound (I) and compound (II) via an oxidized carbohydrate moiety comprised in the polypeptide.

Therefore, the present invention relates to a pharmaceutical composition as described above wherein the polypeptide is reacted with compound (II) or with the reaction product of compound (I) and compound (II) via an oxidized carbohydrate moiety comprised in the polypeptide.

According to preferred embodiments, the polypeptide is GCS-F, AT III, IFN-beta or erythropoietin, more preferably erythropoietin.

Therefore, the present invention also relates to a pharmaceutical composition as described above wherein the polypeptide is erythropoietin.

According to an especially preferred embodiment of the present invention, the pharmaceutical composition as described above is produced by reacting hydroxyethyl starch in an aqueous medium with a compound according to the following formula

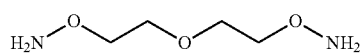

and by reacting the reaction product with erythropoietin.

According to a particularly preferred embodiment, the erythropoietin is oxidised with sodium periodate prior to the aforementioned reaction.

According to another particularly preferred embodiment, the erythropoietin is partially desialylated and subsequently oxidised with sodium periodate prior to the reaction.

According to a further preferred embodiment of the present invention, pharmaceutical compositions comprising a hydroxyalkyl starch derivative which are produced on the basis of a completely reduced Thio-EPO according to Example 5 are excluded.

According to another preferred embodiment, the present invention also relates to a pharmaceutical composition comprising, in a therapeutically effective amount, a hydroxyalkyl starch derivative as described above wherein the reaction product of compound (I) with compound (II) is reacted via the at least one functional group X comprised in compound (II) with at least one further compound or wherein compound (II) is reacted via the at least one functional group X with at least one further compound prior to the reaction with compound (I) and wherein the at least one further compound is a crosslinking compound and the reaction product of the reaction product of compounds (I) and (II) with the crosslinking compound is reacted with a polypeptide.

According to a still further preferred embodiment, the present invention relates to the aforementioned pharmaceutical composition wherein the polypeptide is erythropoietin.

The above-mentioned pharmaceutical composition is especially suitable for the treatment of anemic disorders or hematopoietic dysfunction disorders or diseases related thereto.

A "therapeutically effective amount" as used herein refers to that amount which provides therapeutic effect for a given condition and administration regimen. The administration of erythropoietin isoforms is preferably by parenteral routes. The specific route chosen will depend upon the condition being treated. The administration of erythropoietin isoforms is preferably done as part of a formulation containing a suitable carrier, such as human serum albumin, a suitable diluent, such as a buffered saline solution, and/or a suitable adjuvant. The required dosage will be in amounts sufficient to raise the hematocrit of patients and will vary depending upon the severity of the condition being treated, the method of administration used and the like.

The object of the treatment with the pharmaceutical composition of the invention is preferably an increase of the hemoglobin value of more than 6.8 mmol/l in the blood. For this, the pharmaceutical composition may be administered in a way that the hemoglobin value increases between from 0.6 mmol/l and 1.6 mmol/l per week. If the hemoglobin value exceeds 8.7 mmol/l, the therapy should be preferably interrupted until the hemoglobin value is below 8.1 mmol/l.

The composition of the invention is preferably used in a formulation suitable for subcutaneous or intravenous or parenteral injection. For this, suitable excipients and carriers are e.g. sodium dihydrogen phosphate, disodium hydrogen phosphate, sodium chlorate, polysorbate 80, HSA and water for injection. The composition may be administered three times a week, preferably two times a week, more preferably once a week, and most preferably every two weeks.

Preferably, the pharmaceutical composition is administered in an amount of 0.01-10 μg/kg body weight of the patient, more preferably 0.1 to 5 μg/kg, 0.1 to 1 μg/kg, or 0.2-0.9 μg/kg, most preferably 0.3-0.7 μg/kg, and most preferred 0.4-0.6 μg/kg body weight.

In general, preferably between 10 μg and 200 μg, preferably between 15 μg and 100 μg are administered per doses.

The invention further relates to a HAS-polypeptide according to the present invention for use in method for treatment of the human or animal body.

The invention further relates to the use of a HAS-EPO conjugate of the present invention for the preparation of a medicament for the treatment of anemic disorders or hematopoietic dysfunction disorders or diseases related hereto.

The invention is further illustrated by the following examples, tables, and figures which are in no way intended to restrict the scope of the present invention.

SHORT DESCRIPTION OF THE FIGURES

FIG. 1

FIG. 1 shows an SDS page analysis of the HES-EPO conjugate, produced according to example 4.1.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 4.1.
Lane C: EPO starting material.

FIG. 2

FIG. 2 shows an SDS page analysis of the HES-EPO conjugate, produced according to example 4.3.
Lane A: Crude product after conjugation according to example 4.3.
Lane B: EPO starting material.
Lane C: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.

FIG. 3

Figure 3:
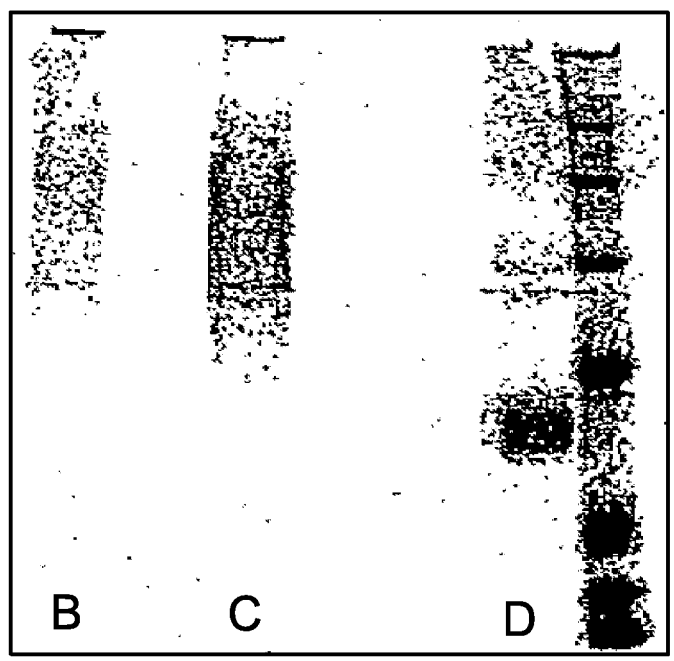

FIG. 3 shows an SDS page analysis of HES-EPO conjugates, produced according to examples 6.1 and 6.4.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 6.4.
Lane C: Crude product after conjugation according to example 6.1.
Lane D: EPO starting material.

FIG. 4

Figure 4:
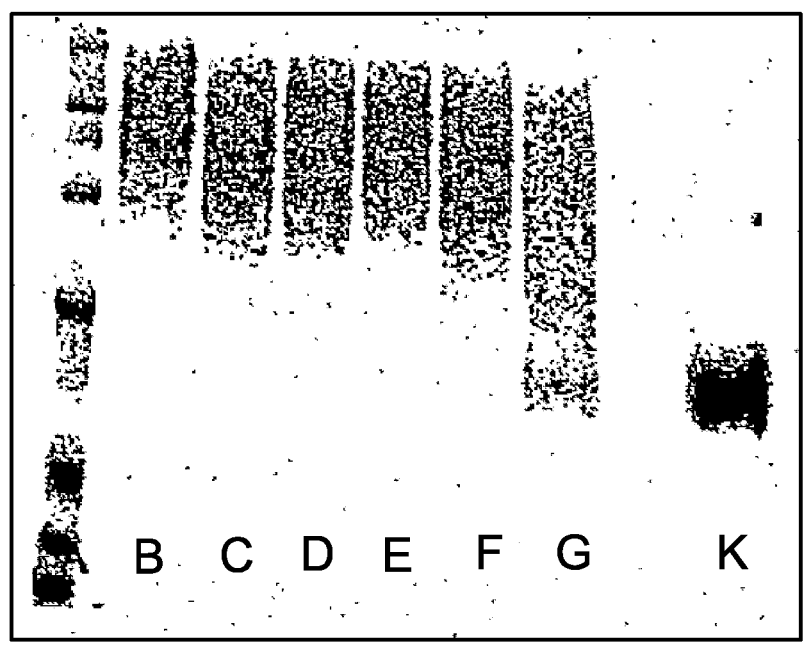

FIG. 4 shows an SDS page analysis of HES-EPO conjugates, produced according to examples 6.2, 6.3, 6.5, and 6.6.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 6.6, based on Example 1.3 b).
Lane C: Crude product after conjugation according to example 6.5, based on Example 1.1 b).
Lane D: Crude product after conjugation according to example 6.6, based on Example 1.3 a).
Lane E: Crude product after conjugation according to example 6.5, based on Example 1.1 a).
Lane F: Crude product after conjugation according to example 6.2.
Lane G: Crude product after conjugation according to example 6.3.
Lane K: EPO starting material.

FIG. 5

SDS-PAGE analyses of EPO-GT-1 subjected to mild acid treatment for 5 min.=lane 2; 10 min.=lane 3; 60 min.=lane 4 and untreated EPO=lane 1; the mobility shift of EPO after removal of N-glycans is shown (+PNGASE).

FIG. 6

HPAEC-PAD pattern of oligosaccharides isolated from untreated EPO and from EPO incubated for 5 min., 10 min. and 60 min. under mild acid hydrolysis conditions. Roman numbers I-V indicate the elution position of I=desialylated diantennary structure, II=trisialylated triantennary structures (two isomers), III=tetrasialylated tetraantennary structure+2 N-acetyllactosamine repeats, IV=tetrasialylated tetraantennary structure+1 N-acetyllactosamine repeat; V=tetrasialylated tetraantennary structure+without N-acetyllactosamine repeat. The elution area of oligosaccharides structures without, with 1-4 sialic acid is indicated by brackets.

FIG. 7

HPAEC-PAD of N-linked oligosaccharides after desialylation; the elution position of N-acetylneuraminic acid is shown; numbers 1-9 indicate the elution position of standard oligosaccharides: 1=diantennary; 2=triantennary (2-4 isomer), 3=triantennary (2-6 isomer); 4=tetraantennary; 5=triantennary plus 1 repeat; 6=tetraantennary plus 1 repeat; 7=triantennary plus 2 repeats; 8=tetraantennary plus 2 repeats and 9=tetraantennary plus 3 repeats.

FIG. 8

SDS-PAGE analysis of mild treated and untreated EPO which were subjected to periodate oxidation of sialic acid residues. 1=periodate oxidized without acid treatment; 2=periodate oxidized 5 min. acid treatment; 3=periodate oxidized and acid treatment 10 min.; 4=periodate oxidized without acid treatment; 5=BRP EPO standard without periodate and without acid treatment.

FIG. 9

HPAEC-PAD pattern of native oligosaccharides isolated from untreated EPO and from EPO incubated for 5 min and 10 min under mild acid hydrolysis conditions and subsequent periodate treatment. The elution area of oligosaccharides structures without and with 1-4 sialic acid is indicated by brackets 1-5.

FIG. 10

SDS-PAGE analysis of the time course of HES-modification of EPO-GT-1-A: 20 μg aliquots of EPO-GT-1-A were reacted with hydroxylamine-modified HES derivative X for 30 min, 2, 4 and 17 hours. Lane 1=30 min reaction time; land 2=2 hour reaction time; land 3=4 hours reaction time; lane 4=17 hours reaction time; lane 5=EPO-GT-1-A without HES-modification. Left figure shows the shift in mobility of EPO-GT-1-A with increasing incubation time in the presence of the with hydroxylamine-modified HES derivative (flow rate: 1 ml·min$^{-1}$) X: Lane 1=30 min reaction time; lane 2=2 hours reaction time; lane 3=4 hours reaction time, land 4=17 hours reaction time; lane 5=EPO-GT-1-A with HES modification. The figure on the right shows analysis of the same samples after their treatment with N-glycosidase.

FIG. 11

SDS-PAGE analysis of Q-Sepharose fractions of HES-EPO conjugates. Each 1% of the flow-through and 1% of the fraction eluting at high salt concentrations were concentrated in a Speed Vac concentrator and were loaded onto the gels in sample buffer. EPO protein was stained by Coomassie Blue. A=sample I; B=sample II; C=sample III; K=control EPO-GT-1; A1, B1, C1 and K1 indicated the flow-through fraction; A2, B2, C2 and K2 indicates the fraction eluted with high salt concentration.

FIG. 12a

Figure 7:
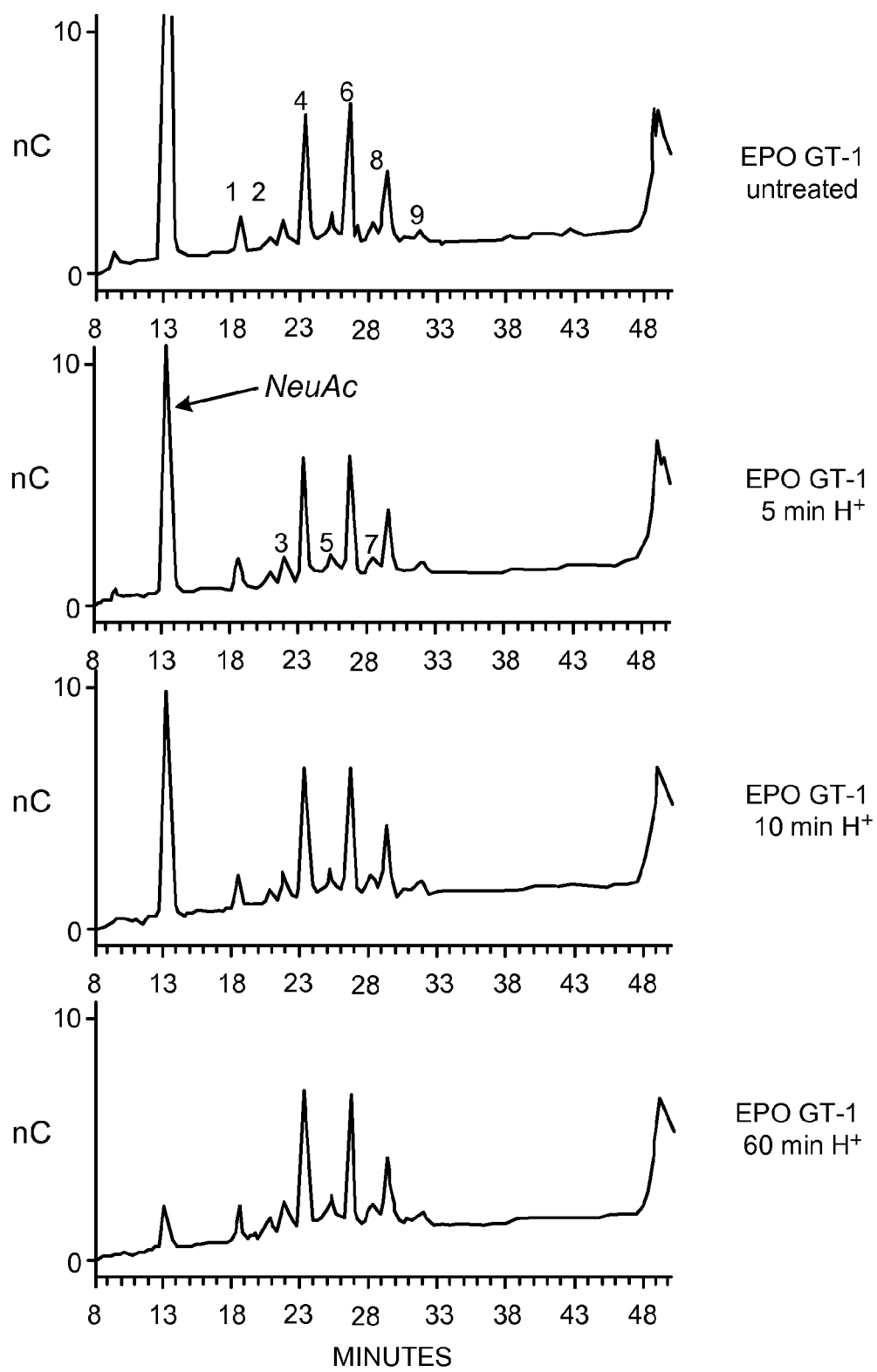

SDS-PAGE analysis of HES-modified EPO sample A2 (see FIG. 7), control EPO sample K2 and EPO-GT-1-A EPO preparation were digested in the presence of N-glycosidase in order to remove N-linked oligosaccharides. All EPO samples showed the mobility shift towards low molecular weight forms lacking or containing O-glycan. A lower ratio of the O-glycosylated and nonglycosylated protein band was observed for the HES-modified EPO sample A2 after de-N-glycosylation and a diffuse protein band was detected around 30 KDa, presumably representing HES-modification at the sialic acid of O-glycan residue (see arrow marked by an asterisk).

FIG. 12b

Figure 11:
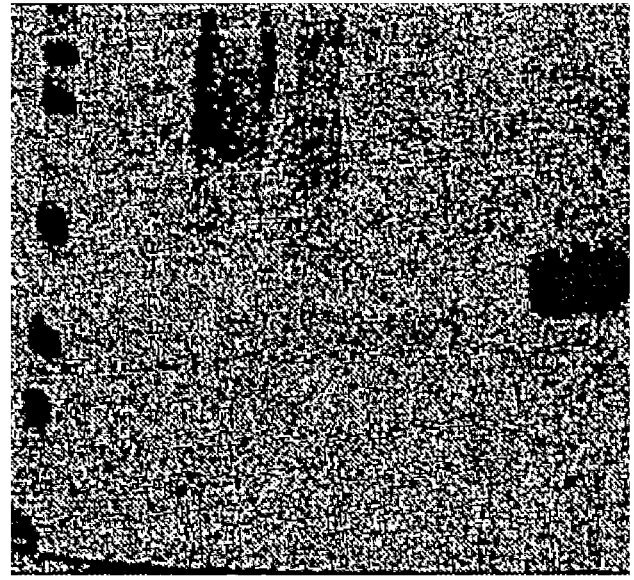
Figure 11:
Figure 12A:
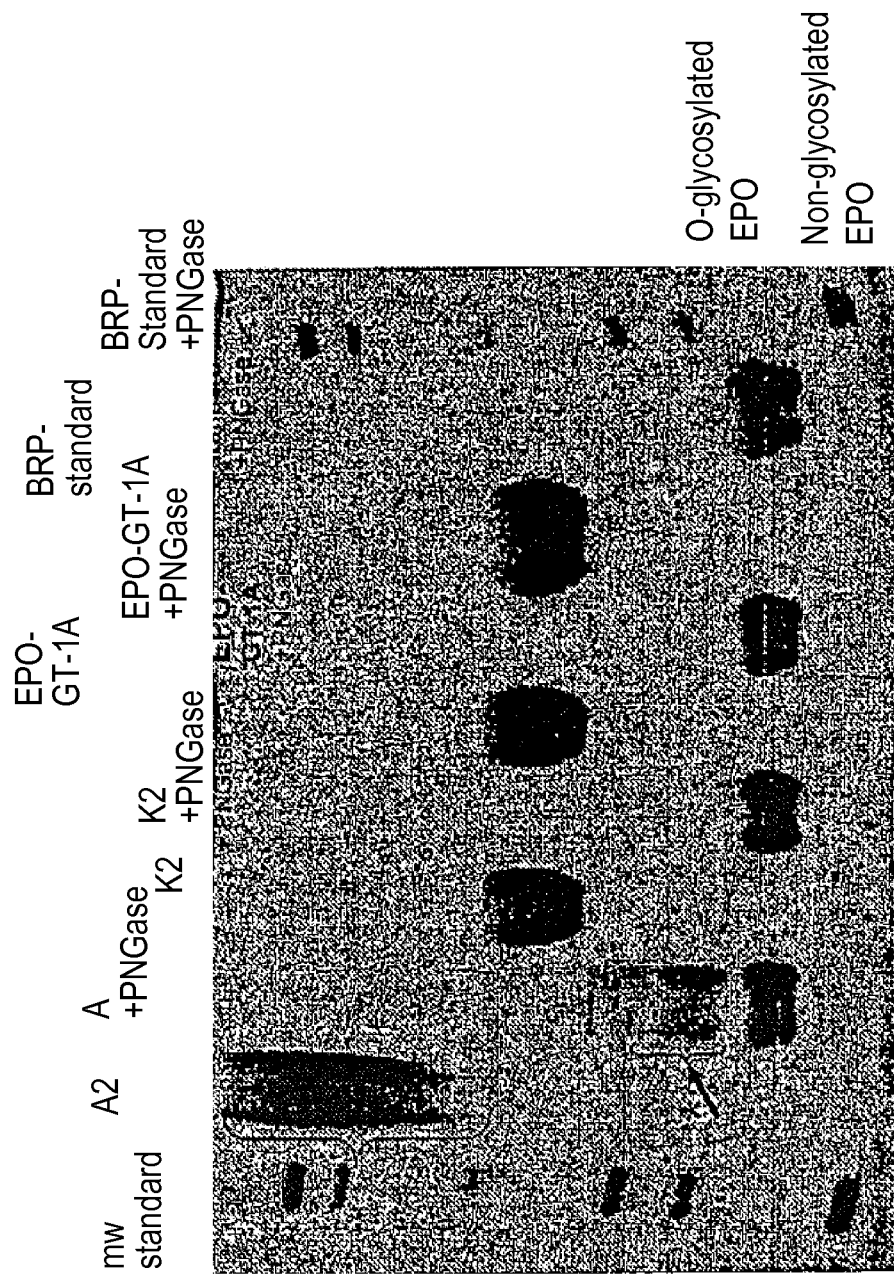

SDS-PAGE analysis after mild hydrolysis of HES-modified EPO sample A2 (see FIG. 11), control EPO sample K2 and EPO-GT-1A which were untreated or digested in the presence of N-glycosidase in order to remove N-linked oligosaccharides (see FIG. 12a). Both high molecular weight form of A2 before and A after N.glycosidase treatment (see brackets with and without arrow) disappeared upon acid treatment of the samples. The BRP EPO standard which was run for comparison was not subjected to mild acid treatment.

FIG. 13

HPAEC-PAD analysis of N-linked oligosaccharide material liberated from HES-modified sample A, from EPO-GT-1-A and from a control EPO sample incubated with unmodified HES (K). Roman numbers I-V indicate the elution position of I=disialylated diantennary structure, II=trisialylated triantennary structures (two isomers), III=tetrasialylated tetraantennary structure+2 N-acetyllactosamine repeats, IV=tetrasialylated tetraantennary structure+1 N-acetyllactosamine repeat, V=tetrasialylated tetraantennary structure+without N-acetyllactosamine repeat; brackets indicate the elution area of di-, tri- and tetrasialylated N-glycans as reported in the legends of FIGS. 6 and 9.

FIG. 14

HPAEC-PAD analysis of N-linked oligosaccharide material liberated from HES-modified sample A, from EPO-GT-1A and from a control EPO sample (K) incubated with unmodified HES. The retention times of a mixture of standard oligosaccharides is shown: numbers 1-9 indicate the elution position of standard oligosaccharides: 1=diantennary; 2=triantennary (2-4 isomer); 3=triantennary (2-6 isomer); 4=tetraantennary; 5=triantennary plus 1 repeat; 6=tetraantennary plus 1 repeat; 7=triantennary plus 2 repeats; 8=tetraantennary plus 2 repeats and 9=tetraantennary plus 3 repeats.

FIGS. 15 to 21

FIGS. 15 to 21 represent MALDI/TOF mass spectra of the enzymatically liberated and chemically desialylated N-glycans isolated from MS-modified EPO and control EPO preparations. Major signals at m/z 1809.7, 2174.8, 2539.9, 2905.0 and 3270.1 ([M+Na]$^+$) correspond to di- to tetraantennary complex-type N-glycan structures with no, one or two N-acetyllactosamine repeats accompanied by weak signals due to loss of fucose or galactose which are due to acid hydrolysis conditions employed for the desialylation of samples for MS analysis.

FIG. 15

MALDI/TOF spectrum: desialylated oligosaccharides of HES-modified EPO A2.

FIG. 16

MALDI/TOF spectrum: desialylated oligosaccharides of EPO GT-1-A.

FIG. 17

MALDI/TOF spectrum: desialylated oligosaccharides of EPO K2.

FIG. 18

MALDI/TOF spectrum: desialylated oligosaccharides of EPO-GT-1.

FIG. 19

MALDI/TOF spectrum: desialylated oligosaccharides of EPO-GT-1 subjected to acid hydrolysis for 5 min.

FIG. 20

MALDI/TOF spectrum: desialylated oligosaccharides of EPO-GT-1 subjected to acid hydrolysis for 10 min.

FIG. 21

MALDI/TOF spectrum: desialylated oligosaccharides of EPO-GT-1 subjected to acid hydrolysis for 60 min.

In the context of the present invention, the degree of substitution, denoted as DS, relates to the molar substitution, as described above (see also Sommermeyer et al., 1987, Krankenhauspharmazie, 8(8), 271-278, in particular p. 273). Throughout the invention, the DS of the HES18/04 when measured according to Sommermeyer et al., 1987, Krankenhauspharmazie, 8(8), 271-278 was 0.5.

EXAMPLES

Example 1

Formation of Hydroxyethyl Starch Derivatives by Reductive Amination

Example 1.1

Reaction of Hydroxyethyl Starch with 1,3-diamino-2-hydroxy propane

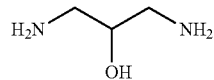

a) To a solution of 200 mg hydroxyethyl starch (HES18/0.4 (MW=18,000 D, DS=0.4)) in 5 ml water, 0.83 mmol 1,3-diamino-2-hydroxy propane and 50 mg sodium cyanoborohydrate NaCNBH$_3$ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (Snake-Skin dialysis tubing, 3.5 KD cut off, Perbio Science Deutschland GmbH, Bonn, D), and lyophilized.

b) Incubation of the mixture resulting from adding 0.83 mmol 1,3-diamino-2-hydroxy propane and 50 mg sodium cyanoborohydrate NaCNBH$_3$ to the solution of 200 mg hydroxyethyl starch was also possible and carried out at 25° C. for 3 d.

Example 1.2

Reaction of Hydroxyethyl Starch with 1,2-dihydroxy-3-amino propane

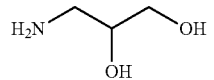

a) To a solution of 200 mg hydroxyethyl starch (HES18/0.4 (MW=18,000 D, DS=0.4)) in 5 ml water, 0.83 mmol 1,2-dihydroxy-3-amino propane and 50 mg sodium cyanoborohydrate NaCNBH₃ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (Snake-Skin dialysis tubing, 3.5 KD cut off, Perbio Science Deutschland GmbH, Bonn, D), and lyophilized.

b) Incubation of the mixture resulting from adding 0.83 mmol 1,2-dihydroxy-3-amino propane and 50 mg sodium cyanoborohydrate NaCNBH₃ to the solution of 200 mg hydroxyethyl starch was also possible and carried out at 25° C. for 3 d.

The reaction of 1,2-dihydroxy-3-amino propane with HES was confirmed indirectly by quantification of formaldehyde, resulting from the oxidative cleavage of the 1,2-diole in the reaction product by periodate as described by G. Avigad, Anal. Biochem. 134 (1983) 449-504.

Example 1.3

Reaction of Hydroxyethyl Starch with 1,4-diamino butane

a) To a solution of 200 mg hydroxyethyl starch (HES 18/0.4 (MW=18,000 D, DS=0.4)) in 5 ml water, 0.83 mmol 1,4-diamino butane and 50 mg sodium cyanoborohydrate NaCNBH₃ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (SnakeSkin dialysis tubing, 3.5 KD cut off, Perbio Science Deutschland GmbH, Bonn, D), and lyophilized.

b) Incubation of the mixture resulting from adding 0.83 mmol 1,4-diamino butane and 50 mg sodium cyanoborohydrate NaCNBH₃ to the solution of 200 mg hydroxyethyl starch was also possible and carried out at 25° C. for 3 d.

Example 1.4

Reaction of Hydroxyethyl Starch with 1-mercapto-2-amino ethane

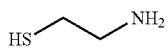

a) To a solution of 200 mg hydroxyethyl starch (HES18/0.4 (MW=18,000 D, DS=0.4)) in 5 ml water, 0.83 mmol 1-mercapto-2-amino ethane and 50 mg sodium cyanoborohydrate NaCNBH₃ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (SnakeSkin dialysis tubing, 3.5 KD cut off, Perbio Science Deutschland GmbH, Bonn, D), and lyophilized.

b) Incubation of the mixture resulting from adding 0.83 mmol 1-mercapto-2-amino ethane and 50 mg sodium cyanoborohydrate NaCNBH₃ to the solution of 200 mg hydroxyethyl starch was also possible and carried out at 25° C. for 3 d.

Example 2

Formation of Hydroxyethyl Starch Derivatives by Conjugation

Example 2.1

Reaction of Hydroxyethyl Starch with Carbohydrazide

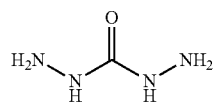

0.96 g of HES18/0.4 (MW=18,000 D, DS=0.4) were dissolved in 8 ml aqueous 0.1 M sodium acetate buffer, pH 5.2, and 8 mmol carbohydrazide (Sigma Aldrich, Taufkirchen, D) were added. After stirring for 18 h at 25° C., the reaction mixture was added to 160 ml of a cold 1:1 mixture of acetone and ethanol (v/v). The precipitated product was collected by centrifugation, re-dissolved in 40 ml water, and dialysed for 3 d against water (SnakeSkin dialysis tubing, 3.5 KD cut off, Perbio Science Deutschland GmbH, Bonn, D), and lyophilized.

Example 2.2

Reaction of Hydroxyethyl Starch with Adepic Dihydrazide

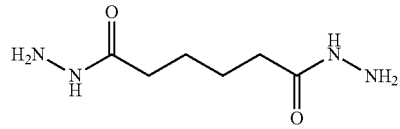 [SMILES: NNC(=O)CCCCC(=O)NN]

0.96 g of HES18/0.4 (MW=18,000 D, DS=0.4) were dissolved in 8 ml aqueous 0.1 M sodium acetate buffer, pH 5.2, and 8 mmol adepic dihydrazide (Lancaster Synthesis, Frankfurt/Main, D) were added. After stirring for 18 h at 25° C., the reaction mixture was added to 160 ml of a cold 1:1 mixture of acetone and ethanol (v/v). The precipitated product was collected by centrifugation, re-dissolved in 40 ml water, and dialysed for 3 d against water (SnakeSkin dialysis tubing, 3.5 KD cut off of Perbio Science Deutschland GmbH, Bonn, D), and lyophilized.

Example 2.3

Reaction of Hydroxyethyl Starch with 1,4-phenylene-bis-3-thiosemicarbazide

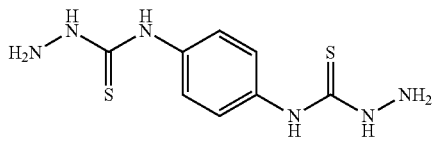 [SMILES: NNC(=S)Nc1ccc(NC(=S)NN)cc1]

0.96 g of HES18/0.4 (MW=18,000 D, DS=0.4) were dissolved in 8 ml aqueous 0.1 M sodium acetate buffer, pH 5.2, and 8 mmol 1,4-phenylene-bis-3-thiosemicarbazide (Lancaster Synthesis, Frankfurt/Main, D) were added. After stirring for 18 h at 25° C., 8 ml water was added to the reaction mixture, and the suspension was centrifuged for 15 min at 4,500 rpm. The clear supernatant was decanted and subsequently added to 160 ml of a cold 1:1 mixture of acetone and ethanol (v/v). The precipitated product was collected by centrifugation, re-dissolved in 40 ml water, and centrifuged for 15 min at 4,500 rpm. The clear supernatant was dialysed for 3 d against water (SnakeSkin dialysis tubing, 3.5 KD cut off, Perbio Science Deutschland GmbH, Bonn, D), and lyophilized.

Example 2.4

Reaction of Hydroxyethyl Starch with O-[2-(2-aminooxyethoxy)-ethyl]-hydroxyl amine

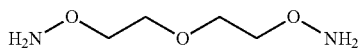

O-[2-(2-aminooxy-ethoxy)-ethyl]-hydroxyl amine was synthesized as described in Boturyn et al. Tetrahedron 53 (1997) p. 5485-5492 in 2 steps from commercially available materials.

0.96 g of HES18/0.4 (MW=18,000 D, DS=0.4) were dissolved in 8 ml aqueous 0.1 M sodium acetate buffer, pH 5.2, and 8 mmol O-[2-(2-aminooxy-ethoxy)-ethyl]-hydroxyl amine were added. After stirring for 18 h at 25° C., the reaction mixture was added to 160 ml of a cold 1:1 mixture of acetone and ethanol (v/v). The precipitated product was collected by centrifugation, re-dissolved in 40 ml water, and dialysed for 3 d against water (SnakeSkin dialysis tubing, 3.5 KD cut off, Perbio Science Deutschland GmbH, Bonn, D), and lyophilized.

Example 3

Oxidation of Erythropoietin

Oxidized erythropoietin was produced as described in Example 7. As oxidised erythropoietin, EPO-GT-1-A as described in Example 7.11(c) was used (EPO-GT-1 without acid hydrolysis, treated with mild periodate oxidation).

Example 4

Conjugation of Hydroxyethyl Starch Derivatives with Oxidized Erythropoietin of Example 3

Example 4.1

Reaction of Oxidized Erythropoietin with the Reaction Product of Example 2.1

Oxidized EPO (1.055 µg/µl) in 20 mM PBS buffer was adjusted to pH 5.3 with 5 M sodium acetate buffer, pH 5.2. To 19 µl of the EPO solution, 18 µl of a solution of the HES derivate as produced according to example 2.1 (MW 18 kD; 18.7 µg/µl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 1. A successful conjugation is indicated by the migration of the protein band to higher molecular weights. The increased bandwidth is due to the molecular weight distribution of the HES derivatives used and the number of HES derivatives linked to the protein.

Example 4.2

Reaction of Oxidized Erythropoietin with the Reaction Product of Example 2.3

Oxidized EPO (1.055 µg/µl) in 20 mM PBS buffer was adjusted to pH 5.3 with 5 M sodium acetate buffer, pH 5.2. To 19 µl of the EPO solution, 18 µl of a solution of the HES derivate as produced according to example 2.3 (MW 18 kD; 18.7 µg/µl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen.

Example 4.3

Reaction of Oxidized Erythropoietin with the Reaction Product of Example 2.4

Oxidized EPO (1.055 µg/µl) in 20 mM PBS buffer was adjusted to pH 5.3 with 5 M sodium acetate buffer, pH 5.2. To 19 µl of the EPO solution, 18 µl of a solution of the HES derivate as produced according to example 2.4 (MW 18 kD; 18.7 µg/µl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 2. A successful conjugation is indicated by the migration of the protein band to higher molecular weights. The increased bandwidth is due to the molecular weight distribution of the HES derivatives used and the number of HES derivatives linked to the protein.

Example 5

Formation of Thio-EPO by Reduction of Erythropoietin 241.5 μg erythropoietin (EPO-GT-1, see Example 7) in 500 μl of a 0.1 M sodium borate buffer, 5 mM EDTA, 10 mM DTT (Lancaster, Morcambe, UK), pH 8.3, were incubated for 1 h at 37° C. The DTT was removed by centrifugal filtration with a VIVASPIN 0.5 ml concentrator, 10 KD MWCO (VIVASCIENCE, Hannover, D) at 13,000 rpm, subsequent washing 3 times with the borate buffer and twice with a phosphate buffer (0.1 M, 9.15 M NaCl, 50 mM EDTA, pH 7.2).

Example 6

Conjugation of Hydroxyethyl Starch Derivatives with Thioerythropoietin Using a Crosslinking Compound In each of the following examples, N-(alpha-maleimidoacetoxy) succinimide ester (AMAS)

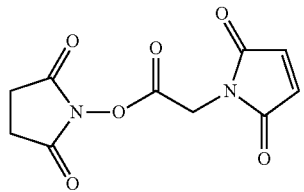 [SMILES: O=C(CN1C(=O)C=CC1=O)ON1C(=O)CCC1=O]

was used as crosslinking compound.

Example 6.1

Reaction of Oxidized Erythropoietin with the Reaction Product of Example 2.1 and the Crosslinking Compound To 50 nmol HES derivate as produced according to example 2.1 and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min each with the phosphate buffer.

To the residual solution, 15 μg of ThioEPO as produced according to example 5 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 3. A successful conjugation is indicated by the migration of the protein band to higher molecular weights. The increased bandwidth is due to the molecular weight distribution of the HES derivatives used and the number of HES derivatives linked to the protein.

Example 6.2

Reaction of Oxidized Erythropoietin with the Reaction Product of Example 2.2 and the Crosslinking Compound To 50 nmol HES derivate as produced according to example 2.2 and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min each with the phosphate buffer.

To the residual solution, 15 μg of ThioEPO as produced according to example 5 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 4. A successful conjugation is indicated by the migration of the protein band to higher molecular weights. The increased bandwidth is due to the molecular weight distribution of the HES derivatives used and the number of HES derivatives linked to the protein.

Example 6.3

Reaction of Oxidized Erythropoietin with the Reaction Product of Example 2.3 and the Crosslinking Compound To 50 nmol HES derivate as produced according to example 2.3 and dissolved in 200 μl of a 0.1 M sodium phosphate buffer (0.1 M, 9.15 M NaCl, 50 mM EDTA, pH 7.2), 10 μl of a solution of 2.5 mmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min each with the phosphate buffer.

To the residual solution, 15 μg of ThioEPO as produced according to example 5 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 4. A successful conjugation is indicated by the migration of the protein band to higher molecular weights. The increased bandwidth is due to the molecular weight distribution of the HES derivatives used and the number of HES derivatives linked to the protein.

Example 6.4

Reaction of Oxidized Erythropoietin with the Reaction Product of Example 2.4 and the Crosslinking Compound To 50 nmol HES derivate as produced according to example 2.4 and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min each with the phosphate buffer.

To the residual solution, 15 μg of ThioEPO as produced according to example 5 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 3. A successful conjugation is indicated by the migration of the protein band to higher molecular weights. The increased bandwidth is due to the molecular weight distribution of the HES derivatives used and the number of HES derivatives linked to the protein.

Example 6.5

Reaction of Oxidized Erythropoietin with the Reaction Product of Example 1.1 and the Crosslinking Compound To 50 nmol HES derivate as produced according to example 1.1, at incubation conditions of 80° C. and 17 h (Example 1.1 a)) as well as of 25° C. and 3 d (Example 1.1 b)), and dissolved in 200 μl of a 0.1 M sodium phosphate buffer (0.1 M, 9.15 M NaCl, 50 mM EDTA, pH 7.2), 10 μl of a solution of 2.5 mmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min each with the phosphate buffer.

To the residual solution, 15 μg of ThioEPO as produced according to example 5 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 4. A successful conjugation is indicated by the migration of the protein band to higher molecular weights. The increased bandwidth is due to the molecular weight distribution of the HES derivatives used and the number of HES derivatives linked to the protein.

Example 6.6

Reaction of Oxidized Erythropoietin with the Reaction Product of Example 1.3 and the Crosslinking Compound To 50 nmol HES derivate as produced according to example 1.3, at incubation conditions of 80° C. and 17 h (Example 1.3 a)) as well as of 25° C. and 3 d (Example 1.3 b), and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min each with the phosphate buffer.

To the residual solution, 15 μg of ThioEPO as produced according to example 5 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 4. A successful conjugation is indicated by the migration of the protein band to higher molecular weights. The increased bandwidth is due to the molecular weight distribution of the HES derivatives used and the number of HES derivatives linked to the protein.

Example 7

Preparative Production of HES-EPO Conjugates

Summary

HES-EPO conjugates were synthesized by coupling of HES derivatives (average mw of 18,000 Dalton; hydroxyethyl substitution degree of 0.4) to the partially (mild periodate) oxidized sialic acid residues on the oligosaccharide chains of recombinant human EPO. Based on carbohydrate structural analysis the modifications introduced did not affect the structural integrity of the core oligosaccharide chains since MALDI/TOF-MS of the mild acid treated HES-modified glycans revealed intact neutral N-acetyllactosamine-type chains which were indistinguishable from those observed in unmodified EPO product The results obtained indicate that at least 3 modified HES-residues are attached per EPO molecule in the case of the EPO preparation which was subjected to modification without prior partial sialic acid removal. An EPO variant lacking about 50% of the sialic acid residues of the former protein showed a similar apparent high molecular weight mobility in SDS-PAGE (60-110 KDa vs 40 KDa for the BRP EPO standard). The HES modified EPO is stable under standard ion-exchange chromatography conditions at room temperature at pH 3-10.

The EPO-bioassay in the normocythaemic mouse system indicates that the HES-modified EPO has 2.5-3.0 fold higher specific activity (IU/mg) in this assay when compared to the International BRP EPO reference standard based on protein determination using the UV absorption value from the European Pharmacopeia and an RP-HPLC EPO protein determination method calibrated against the BRP EPO standard preparation.

Example 7.1

Materials and Methods (a) Liberation of N-Linked Oligosaccharides by Digestion with N-Glycosidase Samples were incubated with 25 units (according to manufacturer's specification, Roche Diagnostics, Germany) of recombinant PNGase F over night at 37° C. Complete digestion was monitored by the specific mobility shift of the protein in SDS-PAGE. The released N-glycans were separated from the polypeptide by addition of 3 volumes of cold 100% ethanol and incubation at −20° C. for at least 2 hours (Schroeter S et al., 1999). The precipitated protein was removed by centrifugation for 10 minutes at 4° C. at 13000 rpm. The pellet was then subjected to two additional washes with 500 µl of ice-cold 75% ethanol. The oligosaccharides in the pooled supernatants were dried in a vacuum centrifuge (Speed Vac concentrator, Savant Instruments Inc., USA). The glycan samples were desalted using Hypercarb cartridges (25 mg or 100 mg of HyperCarb) as follows prior to use: the columns were washed with 3×500 µl of 80% acetonitrile (v/v) in 0.1% TFA followed by washes with 3×500 µl of water. The samples were diluted with water to a final volume of 300 µl-600 µl before loading onto the cartridge which then was rigorously washed with water. Oligosaccharides were eluted with 1.2 ml (25 mg cartridges); 1.8 ml in the case of 100 mg cartridges) 25% acetonitrile in water containing 0.1% trifluoroacetic acid (v/v). The eluted oligosaccharides were neutralised with 2 M $NH_4OH$ and were dried in a Speed Vac concentrator. In some cases desalting of N-glycosidase released oligosaccharides was performed by adsorption of the digestion mixture from samples <100 µg of total (glyco) protein onto 100 mg Hypercarb cartridges.

(b) Analysis of Oligosaccharides by Matrix-Assisted Laser Desorption/Ionization Time-of-Flight Mass-Spectrometry (MALDI/TOF/TOF-MS)

A Bruker ULTRAFLEX time-of-flight (TOF/TOF) instrument was used: native desialylated oligosaccharides were analyzed using 2,5-dihydroxybenzoic acid as UV-absorbing material in the positive as well as in the negative ion mode using the reflectron in both cases. For MS-MS analyses, selected parent ions were subjected to laser induced dissociation (LID) and the resulting fragment ions separated by the second TOF stage (LIFT) of the instrument. Sample solutions of 1 µl and an approximate concentration of 1-10 pmol·µl$^{-1}$ were mixed with equal amounts of the respective matrix. This mixture was spotted onto a stainless steel target and dried at room temperature before analysis.

Example 7.2

Preparation and Characterization of Recombinant Human EPO (EPO-GT-1)

EPO was expressed from recombinant CHO cells as described (Mueller P P et al., 1999, Domer A J et al., 1984) and the preparations were characterized according to methods described in the Eur. Phar. (*Ph. Eur.* 4, *Monography* 01/2002:1316: *Erythropoietin concentrated solution*). The final product had a sialic acid content of 12 nMol (+/−1.5 nMol) per nMol of protein. The structures of N-linked oligosaccharides were determined by HPAEC-PAD and by MALDI/TOF-MS as described (Nimtz et al., 1999, Grabenhorst, 1999). The EPO preparations that were obtained contained di-, tri- and tetrasialylated oligosaccharides (2-12%, 15-28% and 60-80%, respectively, sulphated and pentasialylated chains were present in small amounts). The overall glycosylation characteristics of EPO preparations were similar to that of the international BRP EPO standard preparation.

The isoelectric focusing pattern of the recombinant EPO was comparable to that of the international BRP Reference EPO standard preparation showing the corresponding isoforms. 25% of the EPO protein lacked β-glycosylation at $Ser_{126}$ of the polypeptide chain.

Example 7.3

Preparation of Partially Desialylated EPO Forms

EPO GT-1 protein (2.84 mg/ml) was heated to 80° C. in 20 mM Na-phosphate buffer pH 7.0 and then 100 µl of 1 N $H_2SO_4$ was added per 1 ml of the EPO solution; incubation was continued for 5 min, 10 min and 60 min, respectively, yielding EPO preparations of different degree of sialylation. Quantitation of oligosaccharides with 0-4 sialic acids was performed after liberation of oligosaccharides with polypeptide N-glycosidase and isolation of N-linked chains was performed by desalting using Hypercarb cartridges (25 mg HyperSep Hypercarb; ThermoHypersil-Keystone, UK). EPO preparations were neutralized by addition of 1 N NaOH and were frozen in liquid $N_2$ and were stored at −20° C. until further use.

Example 7.4

Periodate Oxidation of Sialylated EPO Forms

To 10 mg of untreated or mild acid treated EPO dissolved in 3.5 ml of 20 mM Na-phosphate buffer pH 7.0 was added 1.5 ml of 0.1 M Na-acetate buffer pH 5.5 and the mixture was cooled to 0° C. in an ice-bath; 500 µl of 10 mM Na-periodate was added and the reaction mixture was kept in the dark for 60 min at 0° C. Then 10 µl of glycerol was added and incubation was continued for further 10 min in the dark. The partially oxidized EPO forms were separated from reagents by desalting using VIVASPIN concentrators (10,000 MWCO, PES Vivascience AG, Hannover, Germany) according to manufacturer's recommendation at 3000 rpm in a laboratory centrifuge equipped with a fixed angle rotor. After freezing in liquid nitrogen the EPO preparations were stored in a final volume of 4 ml at −20° C.

100 µg aliquots of the partially oxidized EPO preparation were subjected to N-glycosidase treatment and oligosaccharides were isolated using Hypercarb cartridges as described. Oligosaccharides were desialylated by mild acid treatment and were analyzed by HPAEC-PAD and their retention times were compared to those of authentic standard oligosaccharides as described (Nimtz et al., 1990 and 1993).

Example 7.5

Reduction of EPO Disulfides with Dithioerythreitol 5 mg of EPO-GT-1 was incubated in 5 ml of 0.1 M Tris/HCl buffer pH 8.1 in the presence of 30 mM dithioerythreitol (DTT) at 37° C. for 60 minutes; removal of DTT was achieved by using a Vivaspin concentrator at 4° C., 4 cycles of buffer exchange. The final reduced EPO preparation was frozen in liquid nitrogen and stored at −20° C. in 50 mM Na-acetate buffer pH 5.5.

Example 7.6

EPO Protein Determination

Quantitative determination of EPO protein was performed by measuring UV absorption at 280 nm according to the Eur. Phar. (European Pharmacopeia 4, Monography 01/2002: 1316: erythropoietin concentrated solution) in a cuvette with 1 cm path length. In addition, EPO was quantitated by applying a RP-HPLC method using a RP-C4 column (Vydac Protein C4, Cat.#214TP5410, Grace Vydac, Ca, US); the HPLC method was calibrated using the erythropoietin BRP 1 reference standard (European Pharmacopeia, Conseil de l'Europe B.P. 907-F67029, Strasbourg Cedex 1).

Example 7.7

Oxidation of Desialylated EPO with Galactose Oxidase 4.485 mg of completely desialylated EPO was incubated in 20 mM Na-phosphate buffer pH 6.8 in the presence of 16 µl catalase (6214 units/200 ml) and 80 µl of galactose oxidase (2250 units/ml from *Dactylium dendroides* (Sigma-Aldrich, Steinheim, Germany); incubation at 37° C. was over night; 2 times 20 µl of galactose oxidase was added after 4 hours and after 8 hours after starting of the incubation.

Example 7.8

Preparation of EPO Samples for Bioassays

Purification of EPO from Incubations of Periodate- or Galactose-Oxidase-Oxidized EPO Protein Preparations with Activated HES Purification of EPO samples (removal of unreacted HES derivatives) was carried out at room temperature. The EPO incubation mixtures (approximately 5 mg of EPO protein) were diluted 1:10 with buffer A (20 mM N-morpholine propane sulfonic acid [MOPS/NaOH] in $H_2O$ bidest, pH 8.0) and were applied to a column containing 3 ml Q-Sepharose HP (Pharmacia Code no. 17-1014-03, Lot no. 220211) equilibrated with 10 column volumes (CV) of buffer A by using a flow rate of 0.5 ml/min. The column was washed with 6-8 CV of buffer A (flow rate=0.8 ml/min.) and elution was performed by using buffer B (20 mM morpholine ethane sulfonic acid [MES/NaOH], 0.5 M NaCl in $H_2O$ bidest, pH 6.5) at a flow rate of 0.5 ml/min. EPO was detected by UV absorption at 280 nm and eluted in about 6 ml. The column was regenerated by using 3 CV of buffer C (20 mM MES, 1.5 M NaCl in $H_2O$ adjusted to pH 6.5) and was re-equilibrated by using 10 CV of buffer A (flow rate=0.7 ml/min).

Buffer exchange of EPO eluates obtained from the Q-Sepharose step was performed using Vivaspin concentrators and phosphate buffered saline (PBS) with each 3 centrifugation cycles per sample; samples were adjusted to 2 ml with PBS and were stored at −20° C.

Only <25% of the partially desialylated and subsequently mild periodate oxidized EPO forms that were subjected to HES-modification were obtained from the Q-Sepharose eluate since under the conditions employed the basic EPO forms did not bind Q-Sepharose and were found in the flow-through together with nonreacted HES derivatives.

Example 7.9

High-pH Anion-Exchange Chromatography with Pulsed Amperometric Detection (HPAEC-PAD)

Purified native and desialylated oligosaccharides were analyzed by high-pH anion-exchange (HPAE) chromatography using a Dionex BioLC system (Dionex, USA) equipped with a CarboPac PA1 column (0.4×25 cm) in combination with a pulsed amperometric detector (PAD) (Schröter et al., 1999; Nimtz et al., 1999). Detector potentials (E) and pulse durations (T) were: E1: +50 mV, T1: 480 ms; E2: +500 mV, T2: 120 ms; E3: −500 mV, T3: 60 ms, and the output range was 500-1500 nA. The oligosaccharides were then injected onto the CarboPac PA1 column which was equilibrated with 100% solvent A. For desialylated oligosaccharides elution (flow rate: 1 ml·min$^{-1}$) was performed by applying a linear gradient (0-20%) of solvent B over a period of 40 min followed by a linear increase from 20-100% solvent B over 5 min. Solvent A was 0.2 M NaOH in bidistilled $H_2O$, solvent B consisted of 0.6 M NaOAc in solvent A. For native oligosaccharides the column was equilibrated with 100% solvent C (0.1 M NaOH in bidistilled $H_2O$) and elution (flow rate: 1 ml·min$^{-1}$) was performed by applying a linear gradient (0-35%) of solvent D over a period of 48 min followed by a linear increase from 35-100% solvent D over 10 min. Solvent D consisted of 0.6 M NaAc in solvent C.

Example 7.10

Monosaccharide Compositional Analysis of N-Glycans, HES-Modified N-Glycans and EPO Protein by GC-MS Monosaccharides were analyzed as the corresponding methyl glycosides after methanolysis, N-reacetylation and trimethylsilylation by GC/MS [Chaplin, M. F. (1982) A rapid and sensitive method for the analysis of carbohydrate. *Anal. Biochem.* 123, 336-341]. The analyses were performed on a Finnigan GCQ ion trap mass spectrometer (Finnigan MAT corp., San Jose, Calif.) running in the positive ion EI mode equipped with a 30 m DB5 capillary column. Temperature program: 2 min isotherm at 80° C., then 10 degrees min$^{-1}$ to 300° C.

Monosaccharides were identified by their retention time and characteristic fragmentation pattern. The uncorrected results of electronic peak integration were used for quantification. Monosaccharides yielding more than one peak due to anomericity and/or the presence of furanoid and pyranoid forms were quantified by adding all major peaks. 0.5 µg of myo-inositol was used as an internal standard compound.

Example 7.11

Results

Example 7.11(a)

Characterization of N-Glycans of Mild Acid Treated (Partially Desialylated) EPO-GT-1

Figure 5:
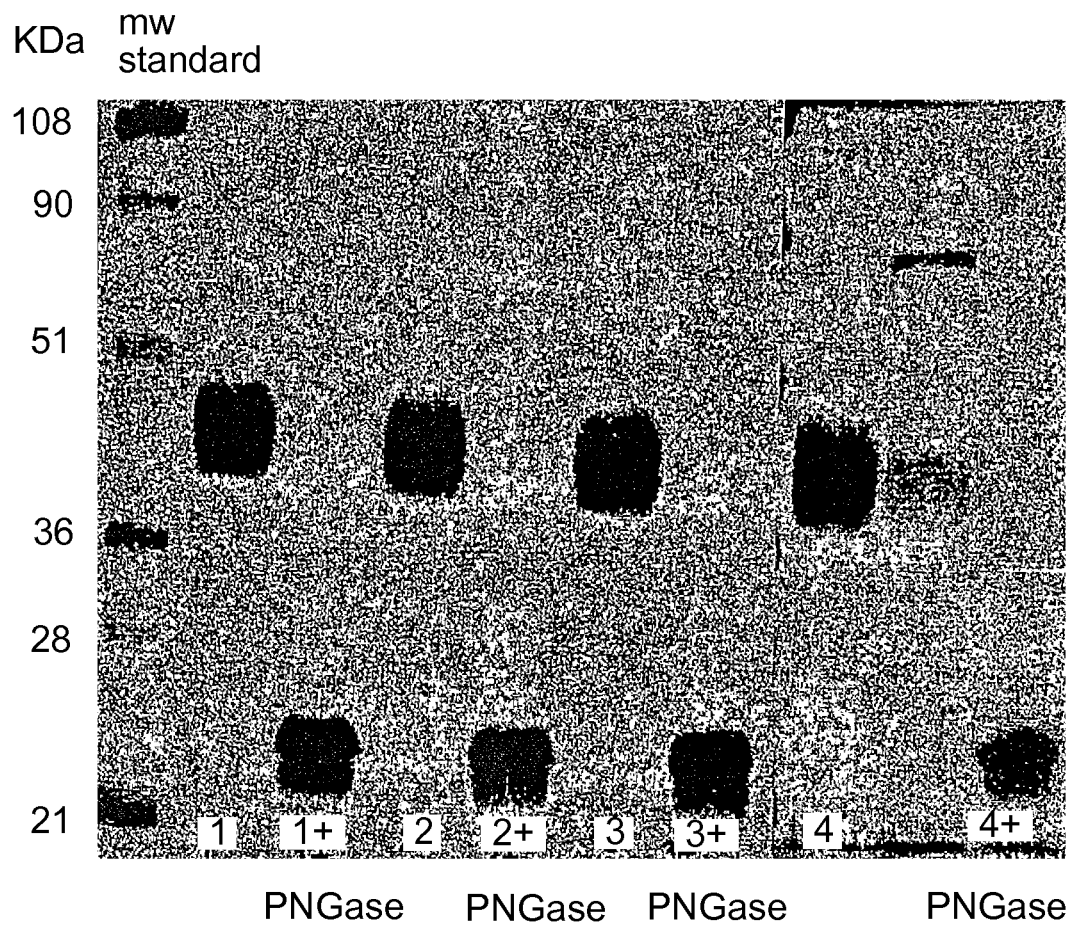
Figure 6:
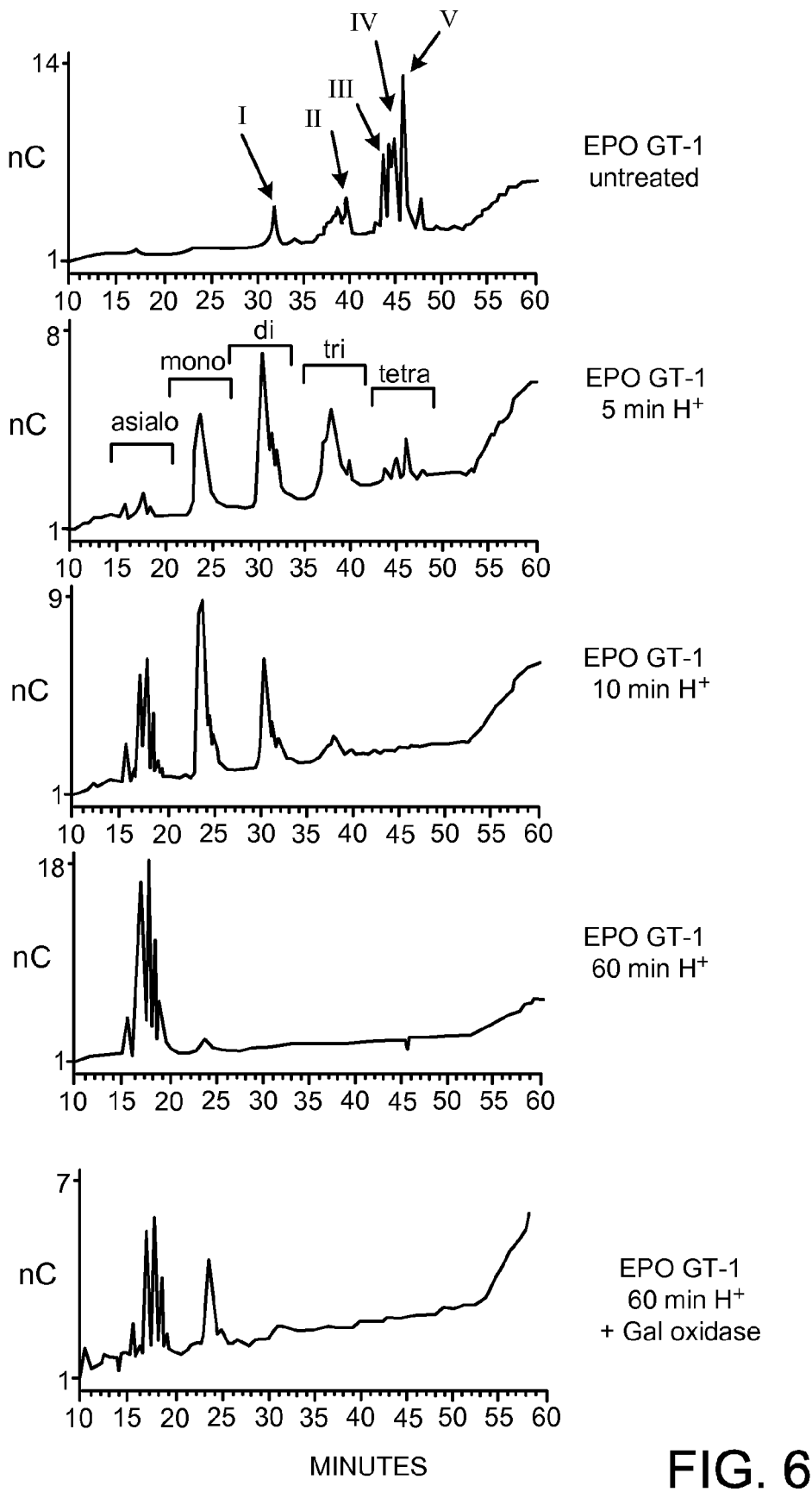

EPO-GT-1 preparations subjected to mild acid treatment for 5, 10 or 60 min. were analyzed by SDS-PAGE before and after liberation of N-linked oligosaccharides by incubation with N-glycosidase as shown in FIG. 5. N-linked oligosaccharides were subjected to HPAEC-PAD oligosaccharide mapping (FIG. 6). The untreated EPO-GT-1 contained >90% of N-linked oligosaccharides with 3 or 4 sialic acid residues whereas after 5 min. of incubation in the presence of mild acid <40% of carbohydrate chains had 3 or 4 sialic acid residues. HPAEC-PAD of the desialylated N-glycans revealed that the ratio of neutral oligosaccharides that were, detected for the untreated EPO-GT-1 and remained stable in the preparations subjected to acid treatment for 5, or 60 min. MALDI/TOE-MS of the desialylated glycans revealed that <90% of the proximal fucose was present after mild acid treatment of the protein.

Example 7.11(b)

Characterization of Periodate Treated EPO-GT-1

Figure 8:
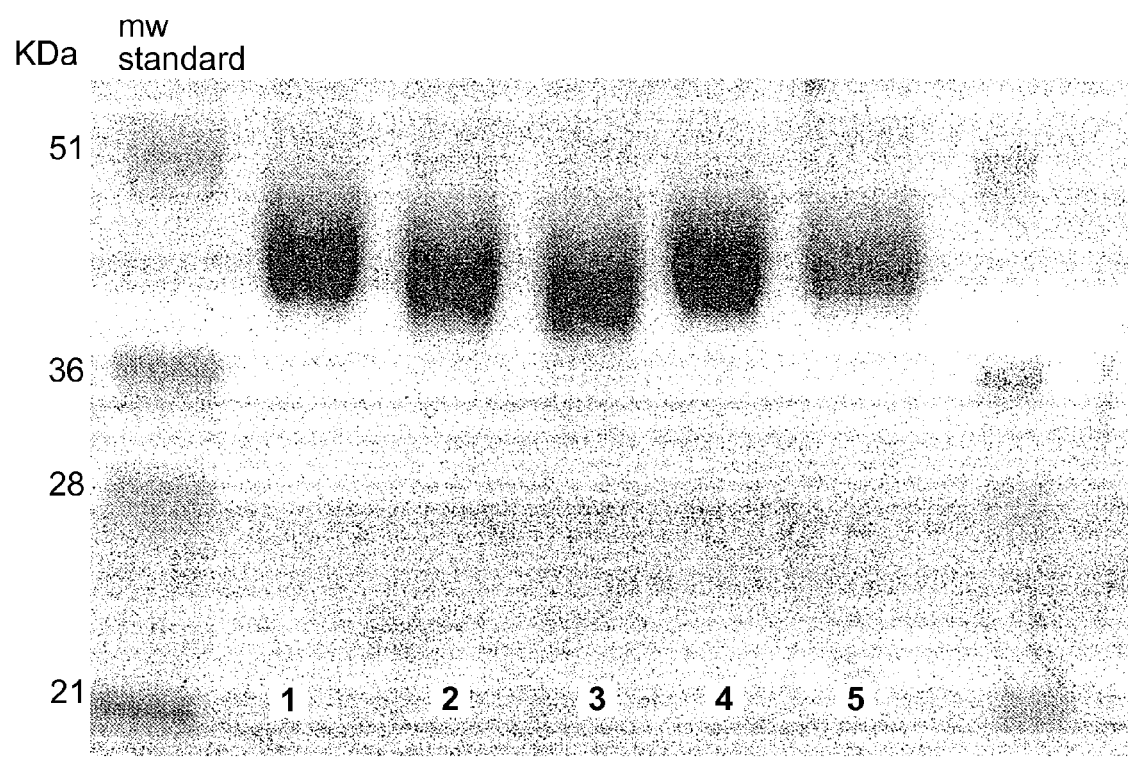

SDS-PAGE mobility of mild periodate treated EPO forms that were previously subjected to a 5 and 10 minute treatment with acid or were not treated are compared in FIG. 8. The conditions used for periodate oxidation of sialic acids did not change the SDS-PAGE pattern of EPO preparations (compare FIG. 5). Oxidation of sialic acids resulted in a shift of oligosaccharides in HPAEC-PAD, analysis to earlier elution times (compare FIGS. 6 and 9).

Example 7.11(c)

Characterization of HES-Modified EPO Derivatives (aa) Time Course of HES Modification of EPO-GT-1-A with Hydroxylamine-Modified HES Derivative X, Produced According to Example 2.4

400 μg of hydroxylamine-modified HES derivative X was added to 20 μg of EPO-GT-1-A (mild periodate oxidized EPO, not acid hydrolyzed prior to mild periodate oxidation) in 20 μL of 0.5 M NaOAc buffer pH 5.5 and the reaction was stopped after 30 min, 2, 4, and 17 hours, respectively, by freezing samples in liquid nitrogen. Subsequently samples were stored at −20° C. until further analysis.

Figure 10:
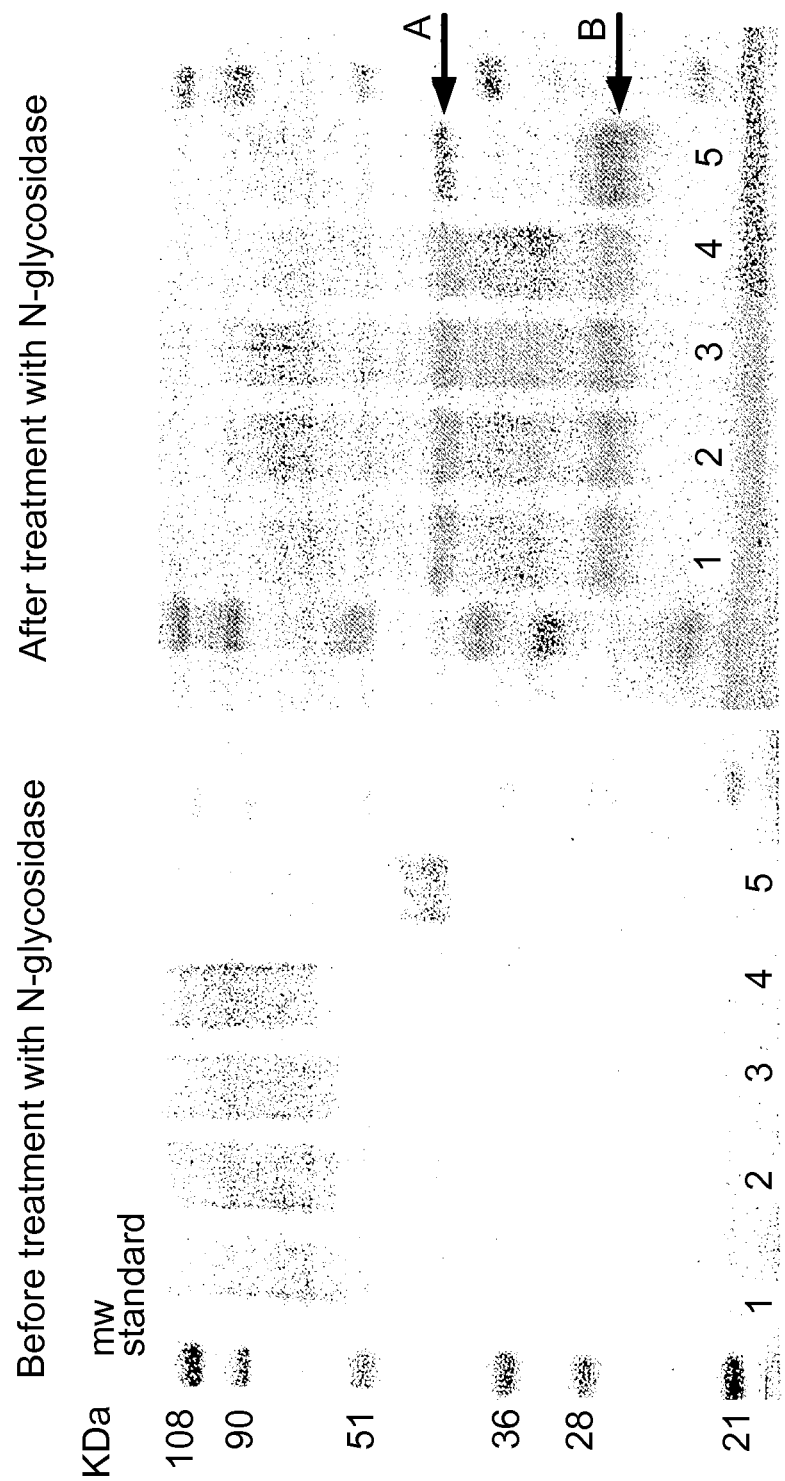

SDS-PAGE sample buffer was added and the samples were heated to 90° C. and applied onto SDS-gels. As shown in FIG. 10, increasing incubation times resulted in an increased shift towards higher molecular weight of the protein. After 17 hours of incubation in the presence of the hydroxylamine-modified HES derivative X a diffuse Coomassie stained protein band was detected migrating in an area between 60 and 11 KDa, based on the position of molecular weight standards (see left part of FIG. 10). Upon treatment with N-glycosidase most of the protein was shifted towards the position of de-N-glycosylated EPO (see FIG. 10, right gel; arrow A indicates migration position of N-glycosidase, arrow B indicates migration position of de-N-glycosylated EPO; the diffuse protein band visible in the region between the 28 KDa and 36 KDa molecular weight standards presumably represents EPO-forms which are modified by HES and the O-glycosylation site of the molecule. In view of the specificity of N-glycosidase we conclude from this result that in fact HES-modification occurs at the periodate oxidized sialic acid residues of glycans of the EPO protein.

(bb) Characterization of HES-EPO Conjugates

HES-EPO conjugates I (originating from EPO-GT-1 after mild periodate oxidation, i.e. from EPO-GT-1-A), II (resulting from EPO-GT-1 subjected to 5 min acid hydrolysis and mild periodate oxidation), III (resulting from EPO-GT-1 subjected to 10 min acid hydrolysis and mild periodate oxidation) were synthesized as described before. A control incubation (K) was included containing unmodified EPO-GT-1 under the same buffer conditions to which an equivalent amount of unmodified HES was added. The incubation mixtures were subjected to further purification for subsequent biochemical analysis of the HES-EPO derivatives.

Incubations HES-EPO conjugates I, II and III as well as the control incubation K were subjected to a Q-Sepharose purification step as described under "Material and Methods" (Example 7.8) in order to remove the excess of nonreacted HES-reagent which was expected in flow through of the ion-exchange column. Due to the high amounts of basic EPO forms contained in previously acid treated samples II and III we expected considerable amounts of modified EPO product from these incubations in the flow through. As is shown in FIG. 11, almost all of the EPO material from samples I was retained by Q-Sepharose column whereas only approximately 20-30% of the samples III and II was recovered in the fraction eluting with high salt concentration. All of the protein material from the incubations with HES derivative X, both in the flow-through and the fractions eluting with high salt, had apparent higher molecular weight in SDS-PAGE when compared to the control EPO.

Figure 12B:
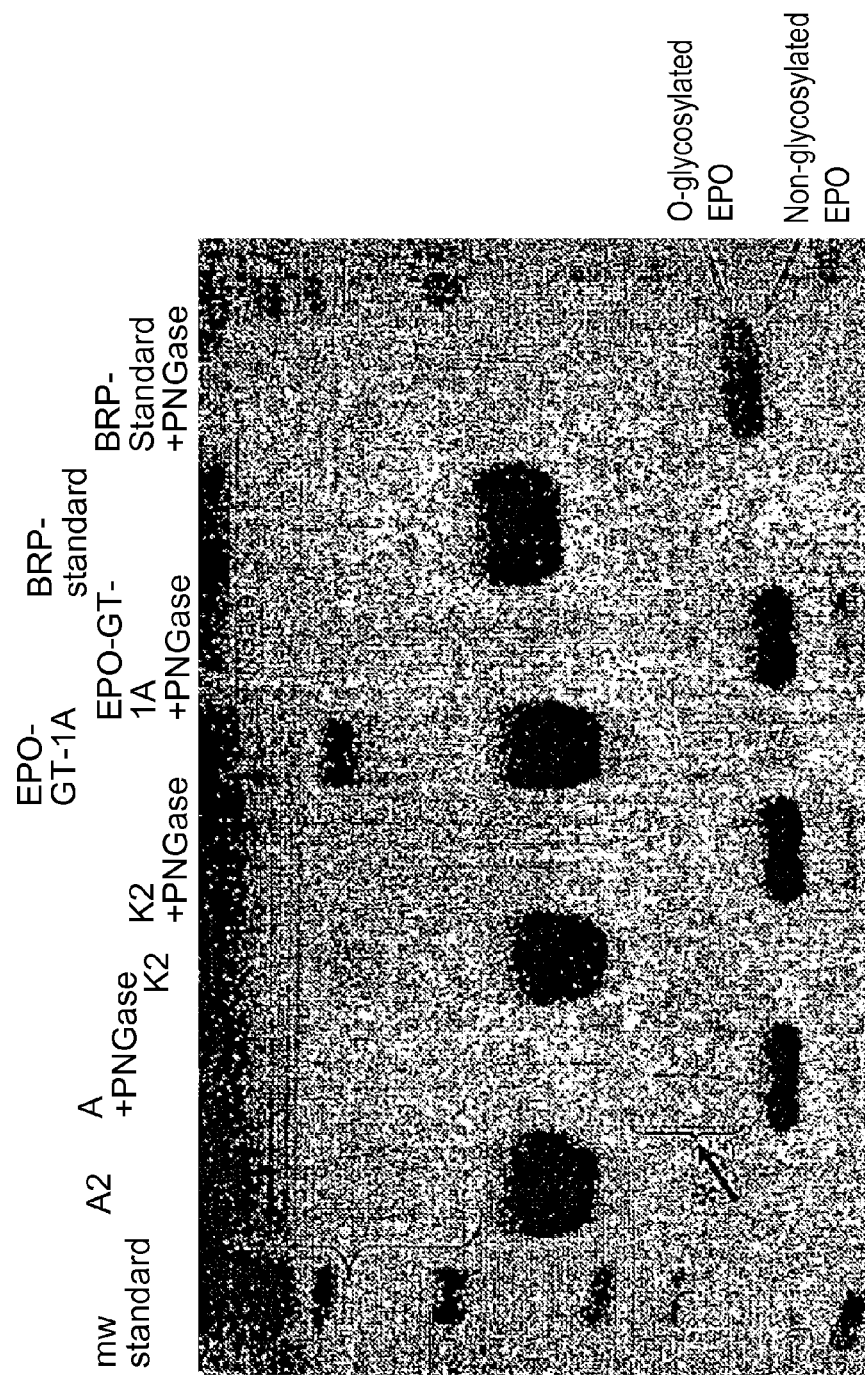

In order to characterize in more detail the HES-modified EPO sample A and K (see FIG. 11) were compared to periodate oxidized form EPO-GT-1-A. The samples were subjected to N-glycosidase treatment and as is depicted in FIGS. 12a and 12b the release of N-glycans resulted in the two low molecular weight bands at the position of the O-glycosylated and nonglycosylated EPO forms of the standard EPO preparation. In the case of sample A a further band migrating at the position of the 28 KDa mw standard was detected suggesting HES-modification at the O-glycan of this EPO variant (cf. Example 7.11(c)(aa)). This band (and also the heavily HES-modified high mw form of N-glycosylated EPO, see FIGS. 12a and 12b) disappeared after subjecting the samples to mild hydrolysis which is in agreement with the view that HES modification was achieved at the periodate oxidised sialic acid residues of erythropoietin.

Aliquots of the N-glycosidase incubation mixtures were hydrolyzed using conditions enabling the complete removal of sialic acids residues (and also the sialic acid linked HES derivative) from oligosaccharides; after neutralization, the mixtures were then absorbed onto small Hypercarb columns for their desalting. The columns were washed rigorously with water followed by elution of bound neutral oligosaccharides with 40% acetonitrile in $H_2O$ containing 0.1% of trifuloacetic acid. The resulting oligosaccharides were subjected to MALDI/TOF-MS. The spectra of the desialylated oligosaccharide fractions from sample A, EPO-GT-1-A and sample K showed identical masses for complex type oligosaccharides at m/z=1810 Da (diantennary), 2175=triantennary, 2540=tetraantennary, 2906=tetraantennary plus 1 N-acetyllactosamine repeat and 3271=tetraantennary plus 2 N-acetyllactosamine repeats; small signals corresponding to lack of fucose (−146) and galactose (minus 162) were detected which are attributable to the acid hydrolysis conditions applied for sialic acid removal (see MALDI—FIGS. 15, 16 and 17).

Figure 13:
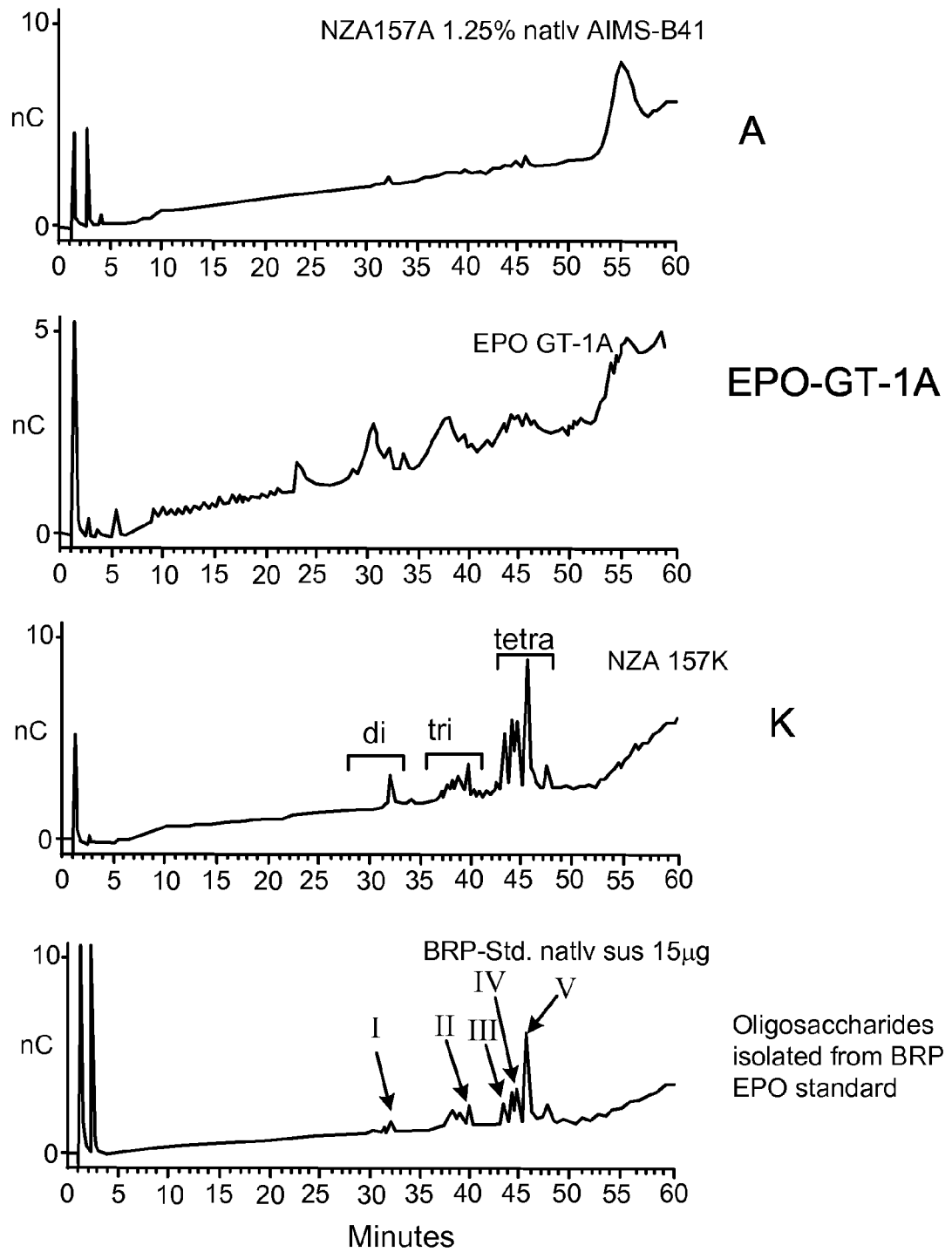
Figure 14:
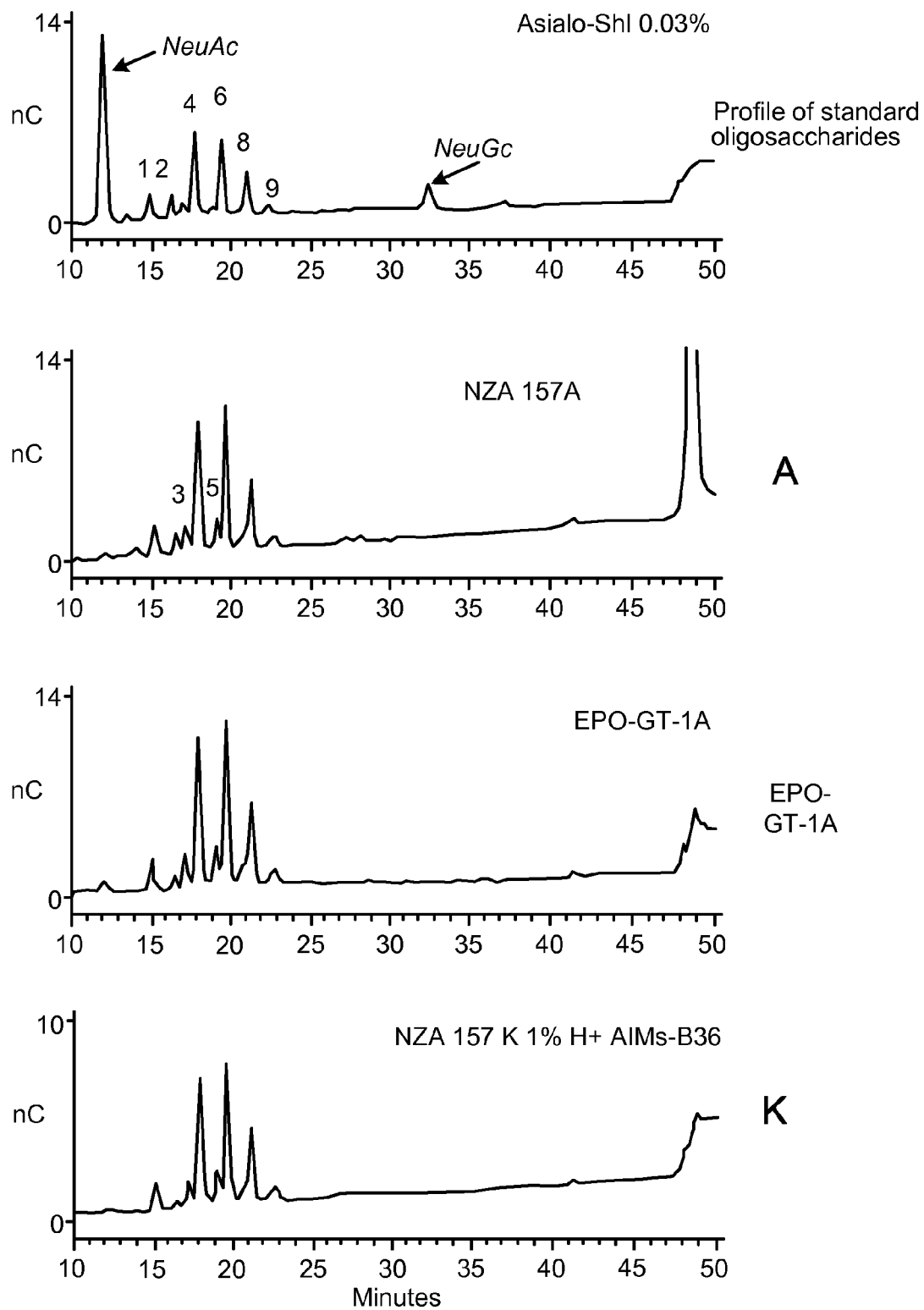
Figure 15:
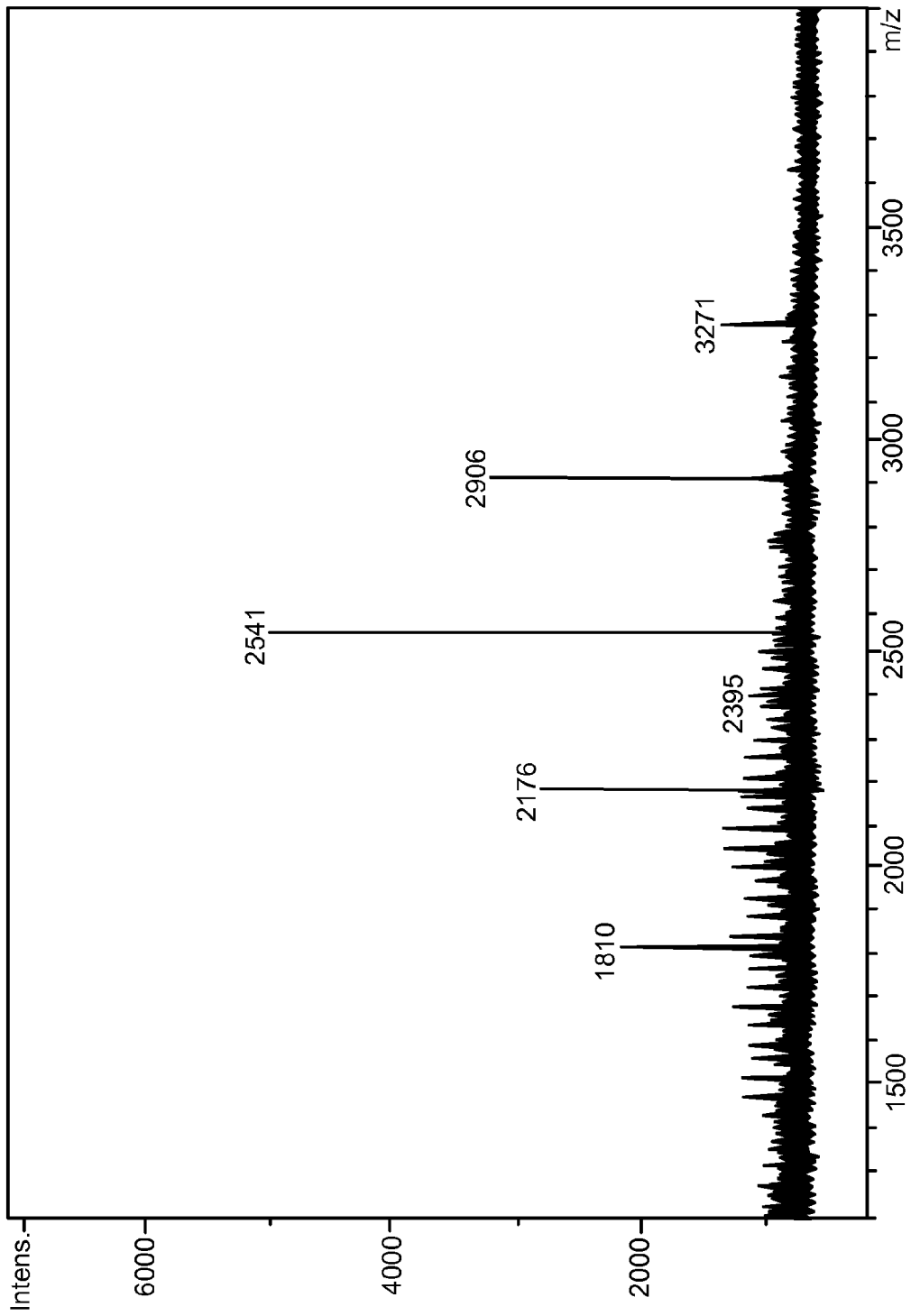
Figure 16:
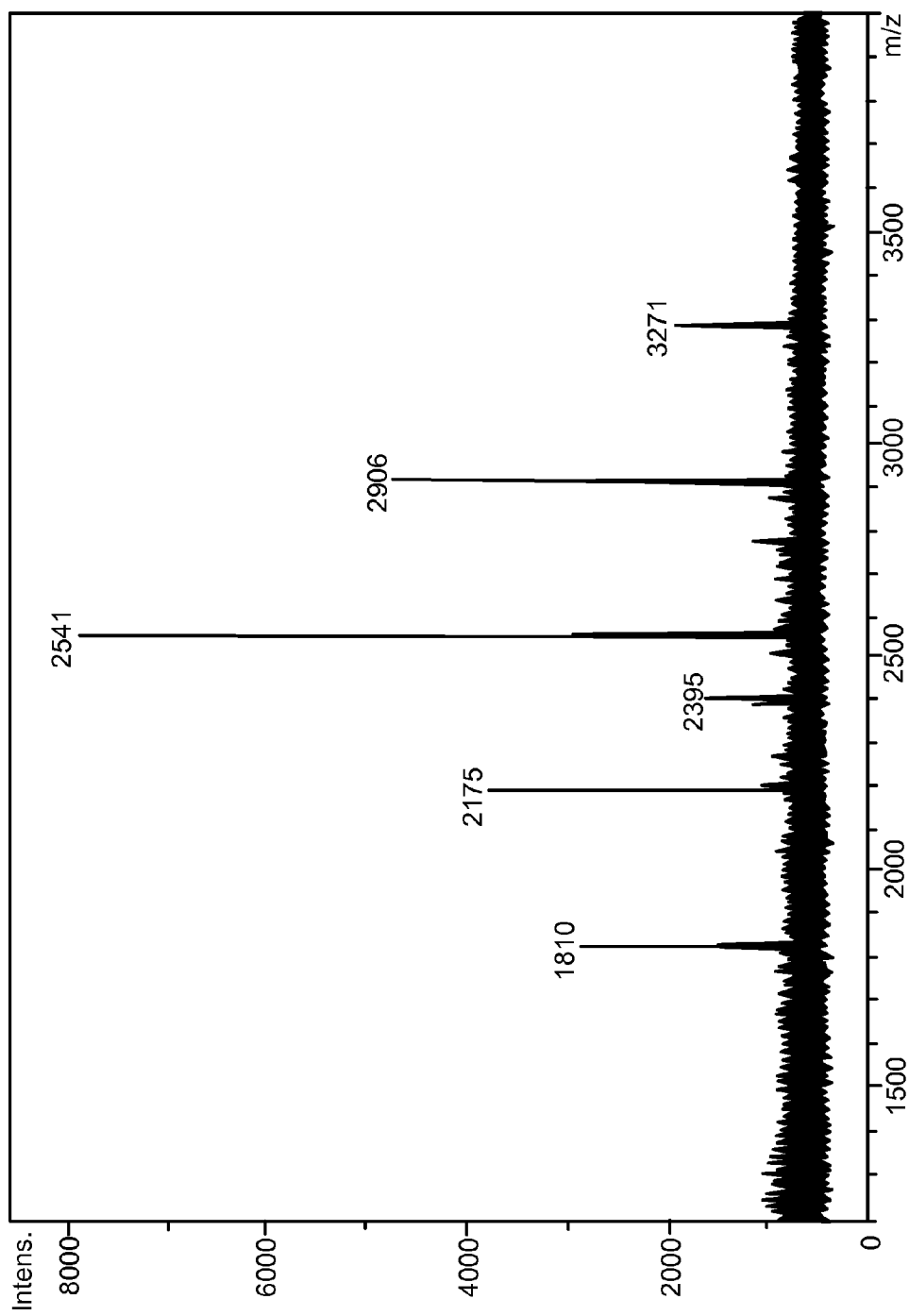
Figure 17:
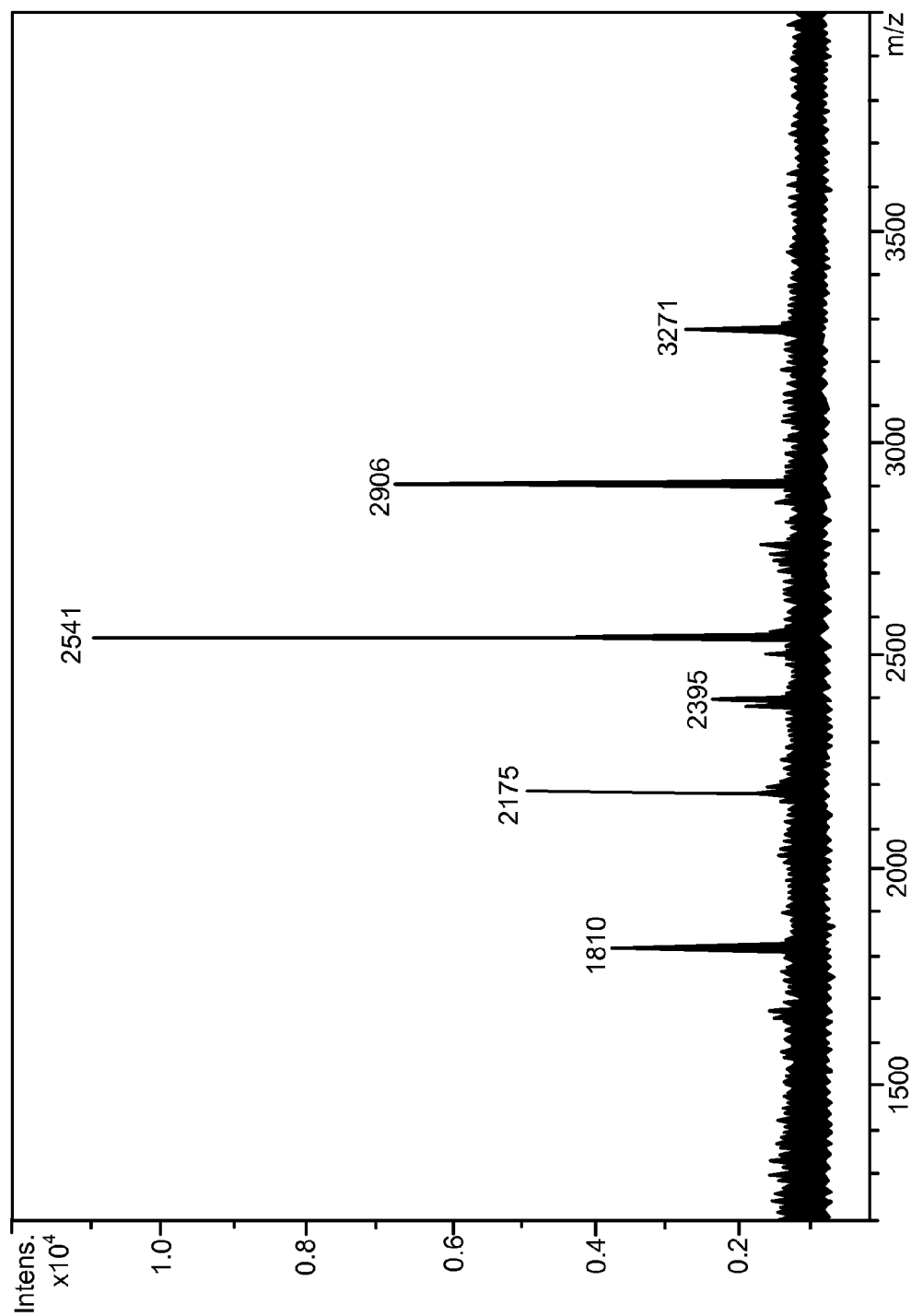
Figure 18:
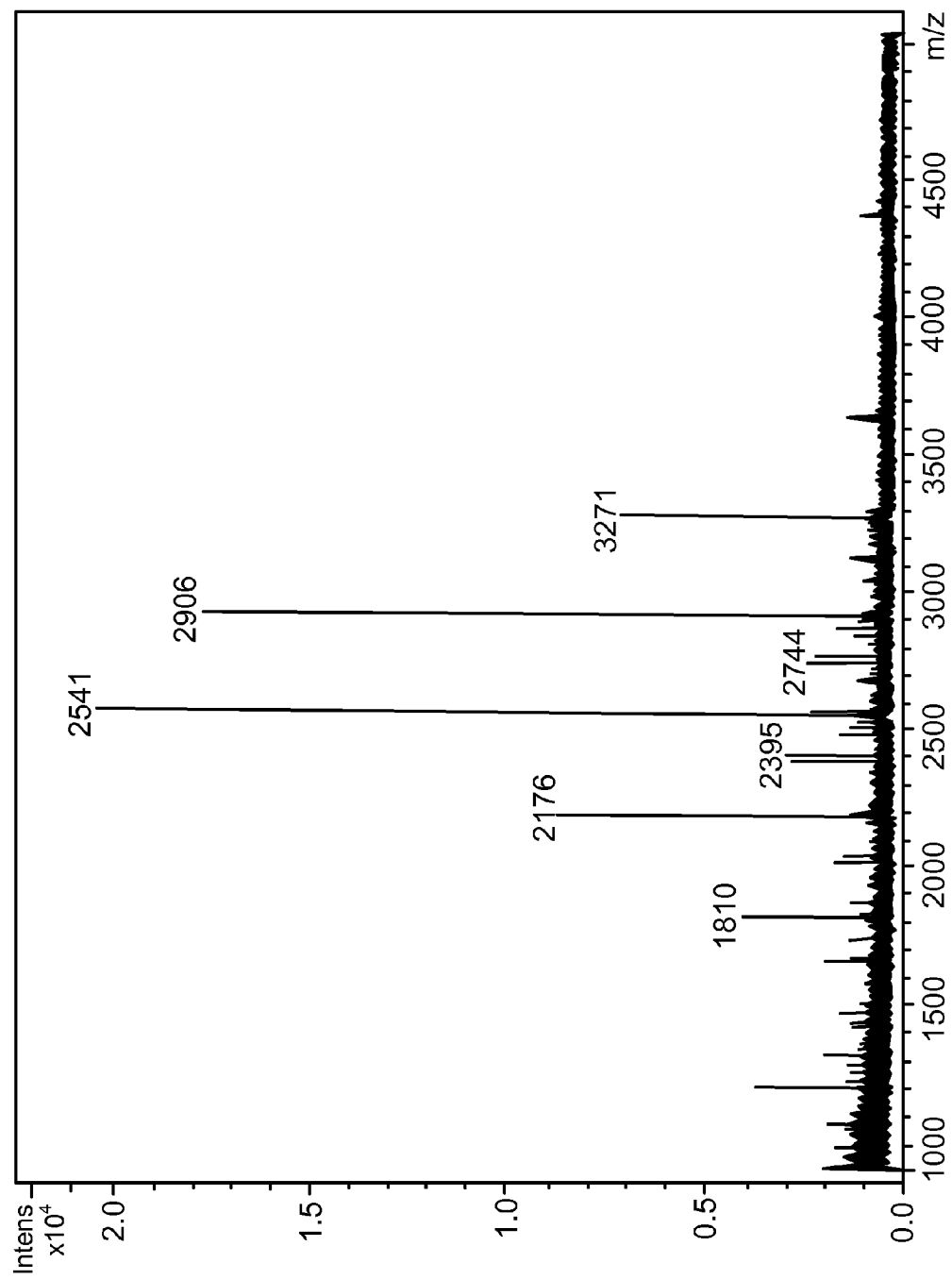
Figure 19:
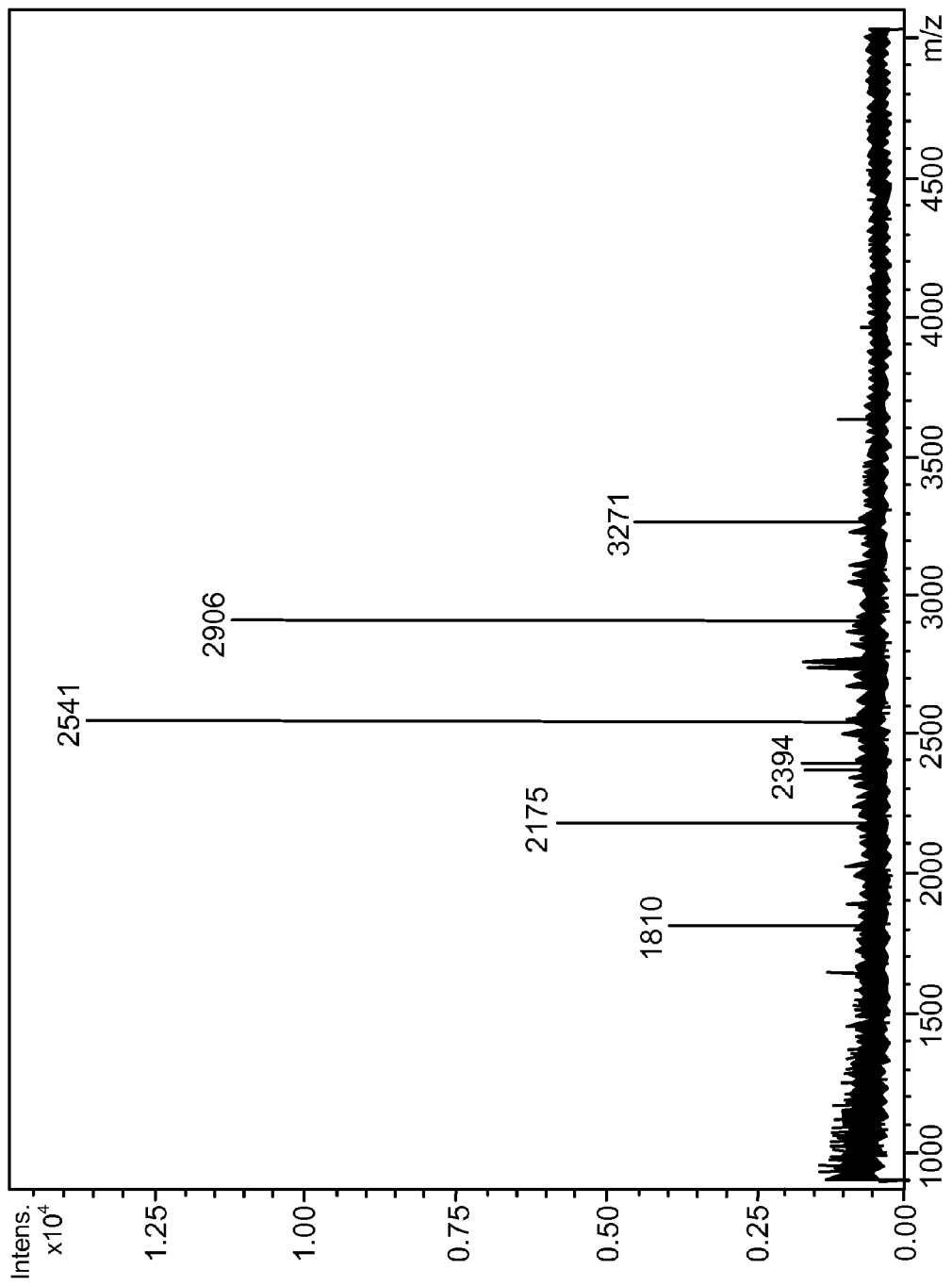
Figure 20:
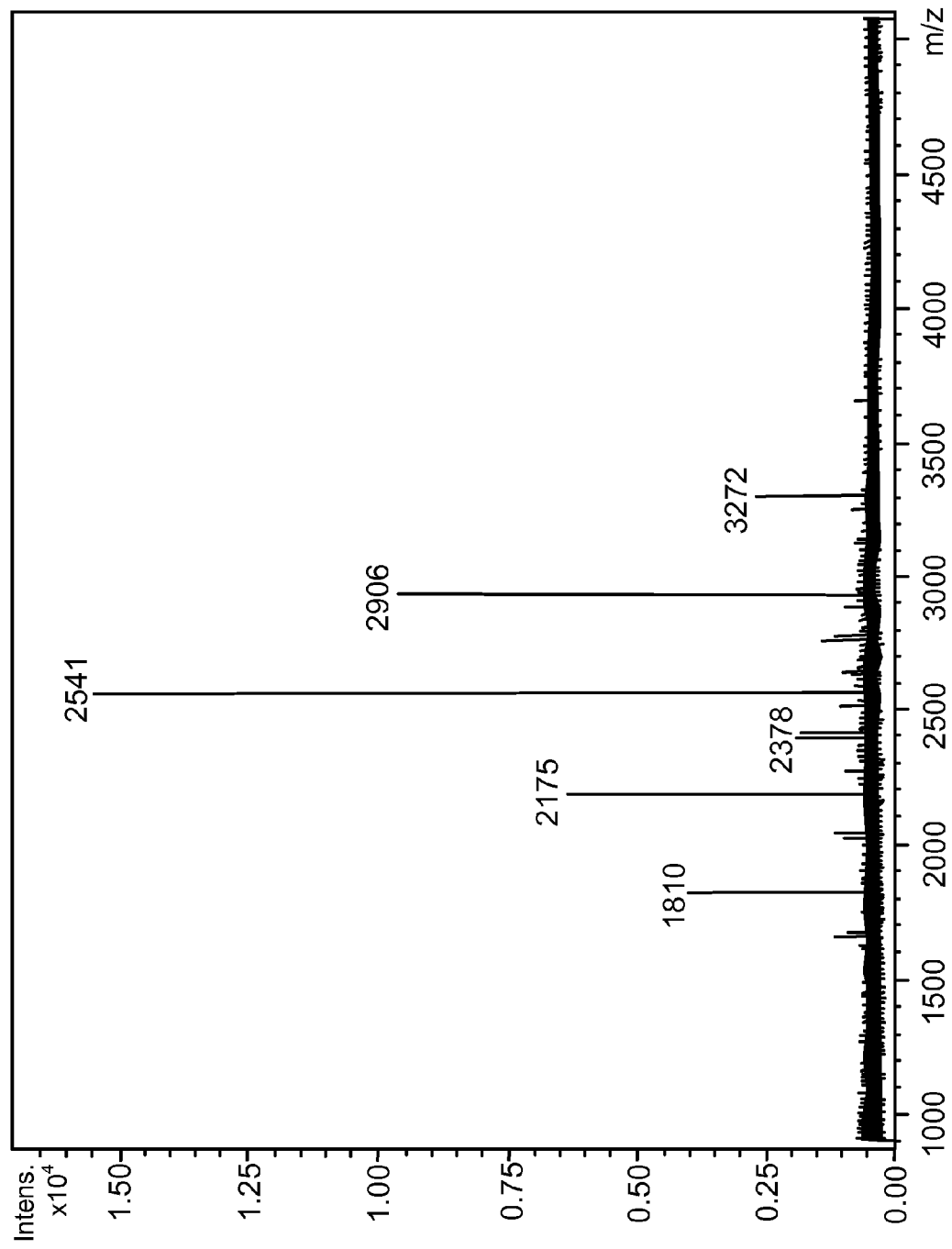
Figure 21:
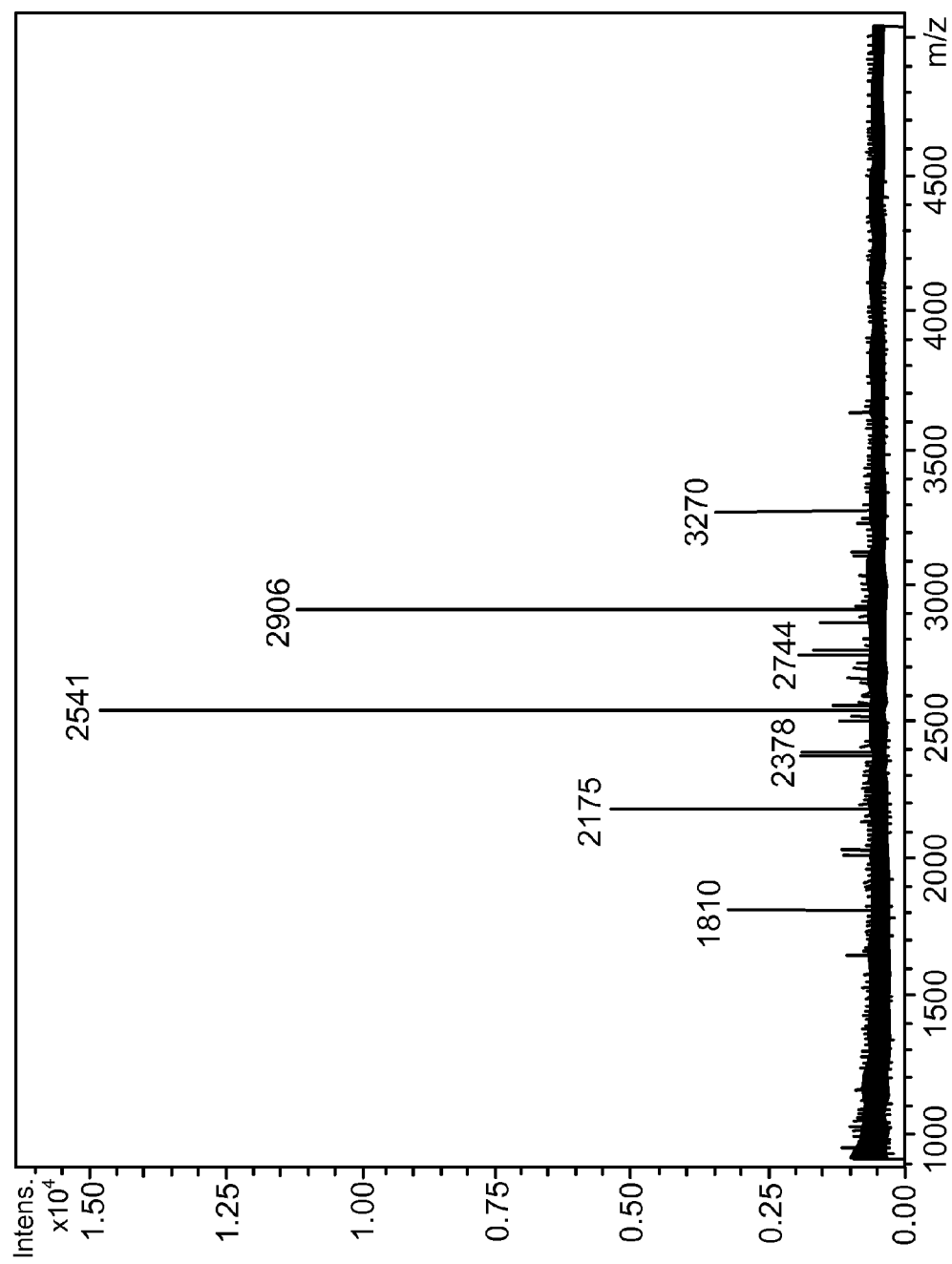

In a parallel experiment the N-glycosidase digestion mixture was absorbed onto 1 ml RP-C18 cartridge (without prior acid hydrolysis of oligosaccharides) and elution was performed with 5% acetonitrile in water containing 0.1% TFA; under these conditions the EPO protein was completely retained onto the RP-material and oligosaccharides were washed off from the column with 5% acetonitrile in $H_2O$ containing 0.1% TFA. The de-N-glycosylated EPO protein was eluted with 70% acetonitrile in $H_2O$ containing 0.1% TFA. The oligosaccharide fractions from the RP-C18 step of N-glycosidase-treated sample A, EPO GT-1-A and sample K were neutralized and subjected to desalting using Hypercarb cartridges as described before. The isolated oligosaccharides were subjected to HPAEC-PAD mapping before (see FIG. 13) and after mild acid treatment under conditions which enabled quantitative removal of sialic acids from glycans (see FIG. 14).

Figure 9:
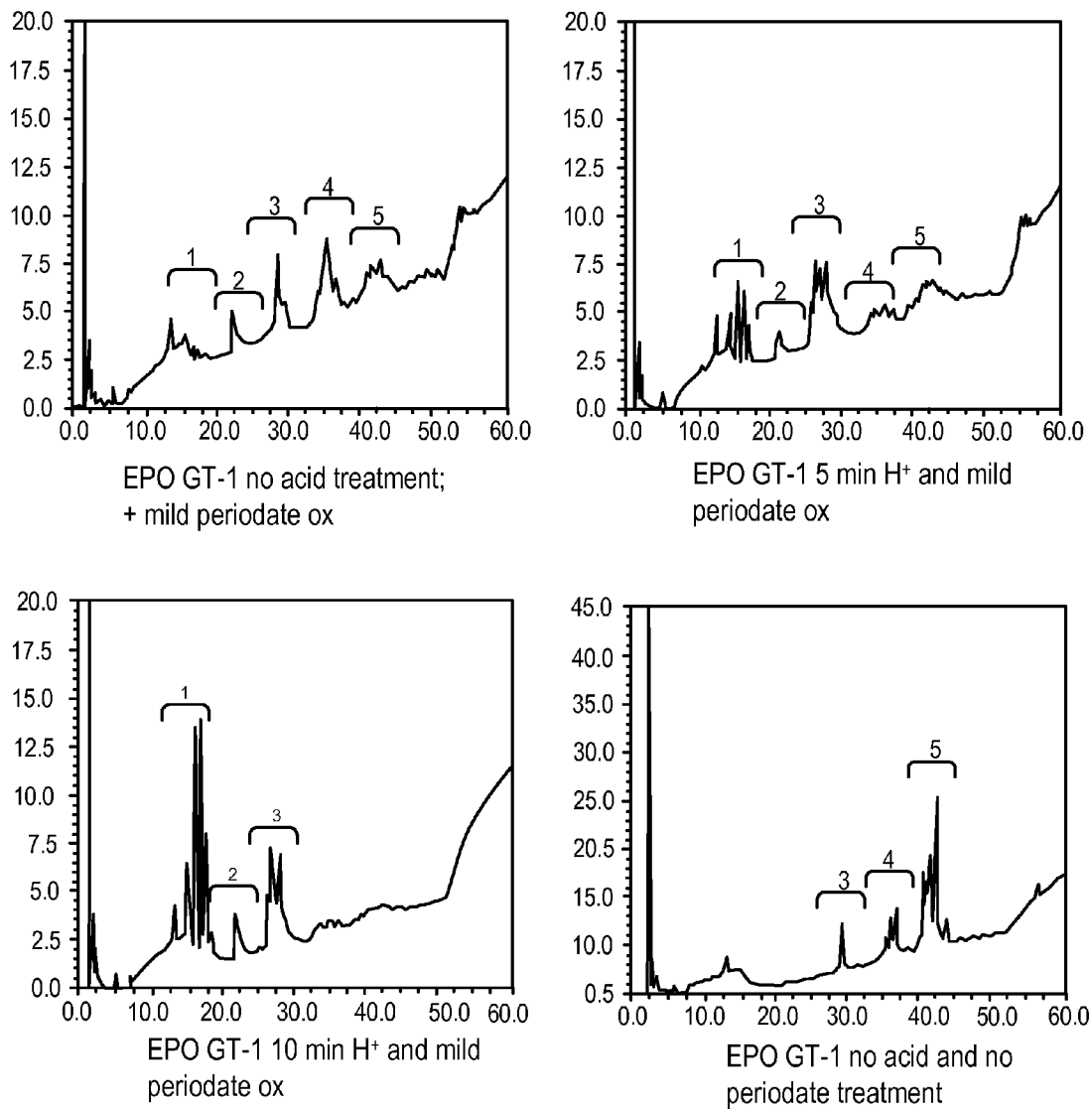

The HPAEC-PAD profile for the native material obtained from the HES-modified sample A showed only neglectable signals for oligosaccharides whereas EPO GT-1-A-derived oligosaccharides exhibited the same glycan profile as the one shown in FIG. 9 (sample named EPO-GT-1 after mild periodate treatment). The elution profile of oligosaccharides obtained from the control EPO sample (K) yielded the expected pattern (compare profile in FIG. 6). For comparison, the native oligosaccharide profile of the international BRP-EPO standard is included for comparison and as reference standard.

After mild acid hydrolysis, all oligosaccharide preparations showed an identical elution profile of neutral oligosaccharide structures (see FIG. 14) with the expected qualitative and quantitative composition of di-, tri- and tetraantennary complex-type carbohydrate chains as described in the methods section for the EPO preparation which was used as a starting material in the present study. This result demonstrates that the HES-modification of the EPO sample results in a covalent linkage of the HES derivative which is detached from the EPO-protein by N-glycosidase and is acid-labile since it is removed from the N-glycans using mild acid treatment conditions known to desialylate carbohydrates (see FIG. 12a+b).

(cc) Monosaccharide Compositional Analysis of HES-EPO and HES-EPO N-Glycans by GC-MS In order to further confirm HES-modification of EPO at the N-glycans of the molecule, EPO samples were digested with N-glycosidase and the EPO protein was adsorbed onto RP-C18 cartridges whereas oligosaccharide material was washed off as described above. As shown in Table 2, glucose and hydroxyethylated glucose derivatives were detected only in the EPO protein which was subjected to HES-modification at cysteine residues and in oligosaccharide fractions of EPO sample A2.

Example 7.11(d)

In-Vivo Assay of the Biological Activity of HES-Modified EPO

The EPO-bioassay in the normocythaemic mouse system indicates was performed according to the procedures described in the European Pharmacopeia; the laboratory that carried out the EPO assay was using the International BRP EPO reference standard preparation. For the HES-modified EPO A2 preparation a mean value for the specific activity of 294,600 units per mg EPO of protein was determined indicating an approximately 3-fold higher specific activity when compared to the International BRP EPO reference standard preparation that was included in the samples sent for activity assays.

The results of the study are summarized in Table 3.

REFERENCES

Nimtz M, Noll G, Paques E P, Conradt H S.
Carbohydrate structures of a human tissue plasminogen activator expressed in recombinant Chinese hamster ovary cells.
FEBS Lett. 1990 Oct. 1; 271 (1-2):14-8
Dorner A J, Wasley L C, Kaufman R J.
Increased synthesis of secreted proteins induces expression of glucose-regulated proteins in butyrate-treated Chinese hamster ovary cells.
J Biol. Chem. 1989 Dec. 5; 264 (34):20602-7
Mueller P P, Schlenke P, Nimtz M, Conradt H S, Hauser H
Recombinant glycoprotein quality in proliferation-controlled BHK-21 cells.
Biotechnol Bioeng. 1999 Dec. 5; 65(5):529-36
Nimtz M, Martha W, Wray V, Kloppel K D, Augustin J, Conradt H S.
Structures of sialylated oligosaccharides of human erythropoietin expressed in recombinant BHK-21 cells.
Eur J. Biochem. 1993 Apr. 1; 213(1):39-56
Hermentin P, Witzel R, Vliegenthart J F, Kamerling J P, Nimtz M, Conradt H S.
A strategy for the mapping of N-glycans by high-ph anion-exchange chromatography with pulsed amperometric detection.
Anal Biochem. 1992 June; 203(2):281-9
Schroter S, Derr P, Conradt H S, Nimtz M, Hale G. Kirchhoff C.
Male specific modification of human CD52.
J Biol Chem. 1999 Oct. 15; 274(42):29862-73

TABLE 1

| Abreviation | Chemical Name | Type |
|---|---|---|
| AMAS | N-(α-Maleimidoacetoxy) succinimide ester | E |
| BMPH | N-(β-Maleimidopropionic acid) hydrazide•TFA | A |
| BMPS | N-(β-Maleimidopropyloxy) succinimide ester | E |

TABLE 1-continued

| Abreviation | Chemical Name | Type | |
|---|---|---|---|
| EMCH | N-(ε-Maleimidocaproic acid) hydrazide | A | |
| EMCS | N-(ε-Maleimidocaproyloxy) succinimide ester | E | |
| GMBS | N-γ-Maleimidobutyryloxy-succinimide ester | E | |
| KMUH | N-(κ-Maleimidoundecanoic acid) hydrazide | A | |
| LC-SMCC | Succinimidyl 4-(N-maleimidomethyl) cyclohexane-1-carboxy-(6-amido-caproate) | E | |
| LC-SPDP | Succinimidyl 6-(3'-[2-pyridyl-dithio]propionamido) hexanoate | F | |
| MBS | m-Maleimidobenzoyl-N-hydroxysuccinimide ester | E | |
| $M_2C_2H$ | 4-(N-Maleimidomethyl)-cyclohexane-1-carboxyl-hydrazide•HCl•1/2 dioxane | A | |
| MPBH | 4-(4-N-Maleimidophenyl)-butyric acid hydazide•HCl | A | |

TABLE 1-continued

| Abreviation | Chemical Name | Type | |
|---|---|---|---|
| SATA | N-Succinimidyl S-acetylthio-acetate | H | 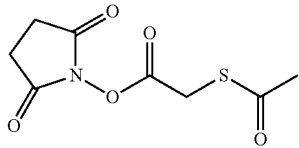 |
| SATP | N-Succinimidyl S-acetylthio-propionate | H | 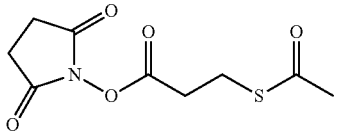 [SMILES: CC(=O)SCCC(=O)ON1C(=O)CCC1=O] |
| SBAP | Succinimidyl 3-(bromoacetamido) propionate | D | 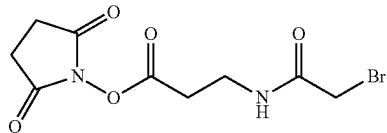 [SMILES: O=C(CBr)NCCC(=O)ON1C(=O)CCC1=O] |
| SIA | N-Succinimidyl iodoacetate | C | 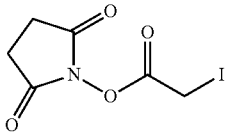 [SMILES: O=C(CI)ON1C(=O)CCC1=O] |
| SIAB | N-Succinimidyl(4-iodoacetyl)aminobenzoate | C | 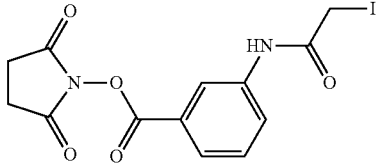 [SMILES: O=C(CI)Nc1cccc(C(=O)ON2C(=O)CCC2=O)c1] |
| SMCC | Succinimidyl 4-(N-maleimidomethyl) cyclohexane-1-carboxylate | E | 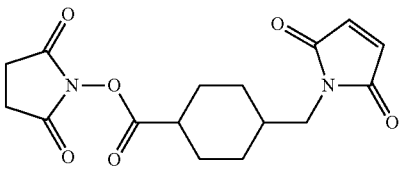 [SMILES: O=C(ON1C(=O)CCC1=O)C1CCC(CN2C(=O)C=CC2=O)CC1] |
| SMPB | Succinimidyl 4-(p-maleimidophenyl)butyrate | E | 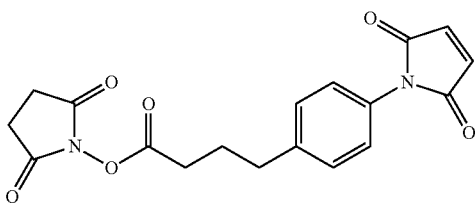 [SMILES: O=C(CCCc1ccc(N2C(=O)C=CC2=O)cc1)ON1C(=O)CCC1=O] |
| SMPH | Succinimidyl-6-(β-maleimidopropionamido) hexanoate | E | 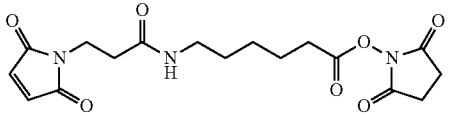 [SMILES: O=C(CCN1C(=O)C=CC1=O)NCCCCCC(=O)ON1C(=O)CCC1=O] |
| SMPT | 4-Succinimidyloxy-carbonyl-methyl-α-(2-pyridyldithio)toluene | F | 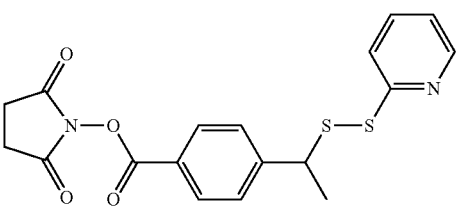 [SMILES: CC(SSc1ccccn1)c1ccc(C(=O)ON2C(=O)CCC2=O)cc1] |

TABLE 1-continued

| Abreviation | Chemical Name | Type |
|---|---|---|
| SPDP | N-Succinimidyl 3-(2-pyridyldithio)propionate | F |
| Sulfo-EMCS | N-(ε-Maleimidocaproyloxy) sulfosuccinimide ester | E |
| Sulfo-GMBS | N-γ-Maleimidobutryloxy-sulfosuccinimide ester | E |
| Sulfo-KMUS | N-(κ-Malcimidoundecanoyloxy)-sulfosuccinimide ester | E |
| Sulfo-LC-SPDP | Sulfosuccinimidyl 6-(3'-[2-pyridyldithio]propionamido) hexanoate | F |
| Sulfo-MBS | m-Maleimidobenzoyl-N-hydroxysulfosuccinimide ester | E |
| Sulfo-SIAB | Sulfosuccinimidyl(4-iodoacetyl)aminobenzoate | C |
| Sulfo-SMCC | Sulfosuccinimidyl 4-(N-maleimidomethyl) cyclohexane-1-carboxylate | E |
| Sulfo-SMPB | Sulfosuccinimidyl 4-(p-maleimidophenyl)butyrate | E |

TABLE 1-continued

| Abreviation | Chemical Name | Type | |
|---|---|---|---|
| Sulfo-LC-SMPT | Suflosuccinimidyl 6-(α-methyl-α-[2-pyridyldithio]-toluamido)hexanoate | F | |
| SVSB | N-Succinimidyl-(4-vinylsulfonyl)benzoate | G | |

TABLE 2

Monosaccharide compositional analysis of glycans from HES-modified EPO and control samples

| **Monosaccharide | I. Glycans from A2 | II. Glycans from EPO-GT-1A | III. Glycans from K2 | III. Glycans from A2 | IV. Glycans from EPO-GT-1A | V. Glycans from K2 | VI. Cystein modified EPO protein* |
|---|---|---|---|---|---|---|---|
| fucose | 1,935 | 3,924 | 2,602 | 2,246 | 4,461 | 2,601 | 2,181 |
| mannose | 6,028 | 11,020 | 9,198 | 6,379 | 11,668 | 6,117 | 6,260 |
| galactose | 8,886 | 19,935 | 14,427 | 10,570 | 16,911 | 11,555 | 10,386 |
| glucose | 17,968 | — | — | 21,193 | trace | trace | 33,021 |
| GlcNAc | 7,839 | 21,310 | 14,440 | 11,360 | 15,953 | 10,503 | 10,498 |
| GlcHe1 | 5,583 | — | — | 5,926 | — | — | 14,857 |
| GlcHe2 | 1,380 | — | — | 1,552 | — | — | 3,775 |
| NeuNAc | 5,461 | 822 | 4,504 | 3,895 | 4,871 | 13,562 | 13,003 |
| inositol | 1,230 | 2,310 | 1,620 | 2,050 | 1,320 | 1,134 | 1,087 |

*the equivalent of Cys-HES-modified EPO protein was subjected to compositional analysis; the EPO protein was isolated from the HES-incubation mixture by chromatography on a Q-Sepharose column as described above and was desalted by centrifugation using a Vivaspin 5 separation device.
**Monosaccharide determinations were performed from single GC runs of the pertrimethylsilylated methylglycosides; the electronical integration values of peaks are given without correction for losses during the derivatisation procedure and recoveries of each compound.

TABLE 3

| Sample No. | Sample description | Calculated specific activity of EPO sample (based on A280 nm and RP-HPLC determination) |
|---|---|---|
| 850247 | 1. HES-modified EPO A2 | 344,000 U/mg |
| 850248 | 2. EPO-GT-1-A | 82,268 U/mg |
| 850249 | 3. Control EPO K2 | 121,410 U/mg |
| 850250 | 4. BRP EPO standard | 86,702 U/mg |
| 850251 | 1. diluted with 4 volume of PBS | 309,129 U/mg |
| 850252 | 2. diluted with 4 volume of PBS | 94,500 U/mg |
| 850253 | 3. diluted with 4 volume of PBS | 114,100 U/mg |
| 850254 | 4. diluted with 4 volume of PBS | 81,200 U/mg |
| 850255 | 1. diluted with 4 volume of PBS | 230,720 U/mg |

What is claimed is:

1. A method of producing a hydroxyethyl starch (HES) derivative, comprising contacting HES of formula (I)

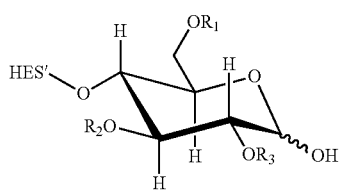

(I)

with O-[2-(2-aminooxy-ethoxy)-ethyl]-hydroxyl amine, having the structure

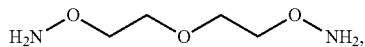

wherein $R_1$, $R_2$ and $R_3$ are independently hydrogen or a 2-hydroxyethyl group, and wherein said contacting is under conditions that result in a reaction product in which the O-[2-(2-aminooxyethoxy)-ethyl]-hydroxyl amine is conjugated via one —O—$NH_2$ group to the HES of formula (I) at its reducing end which is not oxidized prior to said contacting.

2. The method of claim 1, wherein said contacting occurs at a temperature of from 5 to 45° C. and at a pH in the range of from 4.5 to 6.5 in an aqueous medium.

3. The method of claim 1, wherein the contacting occurs in water, dimethyl sulfoxide (DMSO), dimethylformamide (DMF), methanol, ethanol, or a mixture of water with one or more of DMSO, DMF, methanol, and ethanol.

4. The method of claim 1, wherein the contacting occurs in a mixture of water with one or more of DMSO, DMF, methanol, and ethanol, wherein the mixture comprises at least 10% water by weight.

5. The method of claim 1, wherein the contacting occurs in a mixture of water with one or more of DMSO, DMF, methanol, and ethanol, wherein the mixture comprises at least 50% water by weight.

6. The method of claim 1, wherein the contacting occurs at a temperature of 10° C. to 30° C.

7. The method of claim 1, wherein the contacting occurs for one hour to 7 days.

8. The method of claim 1, wherein the contacting occurs for two hours to 48 hours.

9. The method of claim 1, wherein the contacting occurs at a pH from 4.5 to 6.5.

10. The method of claim 1, further comprising isolating the reaction product from the reaction mixture.

11. The method of claim 10, wherein the isolating comprises one or more of centrifugation, dialysis, filtration, centrifugal filtration, pressure filtration, ion exchange chromatography, HPLC, MPLC, gel filtration and lyophilization.

12. The method of claim 1, further comprising precipitating the reaction product.

13. The method of claim 1, wherein the contacting occurs in water and wherein the method further comprises precipitating the reaction product, and wherein the precipitating comprises contacting the reaction mixture with acetone and ethanol.

14. The method of claim 13, wherein the precipitated reaction product is subjected to a further treatment selected from the group consisting of dialysis, centrifugal filtration or pressure filtration ion exchange chromatography, HPLC, MPLC, gel filtration and lyophilization.

15. The method of claim 13, wherein the precipitated reaction product is further dialysed and then lyophilized.

16. The method of claim 1, further comprising contacting the remaining —O—NH$_2$ group of the reaction product with a further compound selected from the group consisting of a polypeptide, a crosslinking compound, and a preliminary reaction product of a crosslinking compound and a polypeptide, wherein the contacting results in a further reaction product in which the O-[2-(2-aminooxy-ethoxy)-ethyl]-hydroxyl amine is conjugated to the further compound via the remaining O—NH$_2$ group of the O-[2-(2-aminooxy-ethoxy)-ethyl]-hydroxyl amine.

17. The method of claim 16, wherein the further compound is a polypeptide.

18. The method of claim 17 wherein the remaining —O—NH$_2$ group of the O-[2-(2-aminooxy-ethoxy)-ethyl]-hydroxyl amine is conjugated to the polypeptide via an oxidized carbohydrate moiety comprised in the polypeptide.

19. The method of claim 16, comprising contacting the reaction product with the further compound at a temperature in the range of from 4 to 37° C.

20. The method of claim 16, comprising contacting the reaction product with the further compound in an aqueous medium.

21. The method of claim 16, wherein the further compound is a crosslinking compound.

22. The method of claim 21, further comprising contacting the further reaction product with a second further compound to give a second further reaction product, wherein said second further compound is a polypeptide.

23. The method of claim 22, wherein in the second further reaction product, the polypeptide is conjugated to the further reaction product via a thio group or an oxidized carbohydrate moiety comprised in the polypeptide.

24. The method of claim 16, wherein the further compound is a preliminary reaction product of a crosslinking compound and a polypeptide.

25. A method for producing a HES derivative, comprising
(i) first contacting O-[2-(2-aminooxy-ethoxy)-ethyl]-hydroxyl amine, having the structure

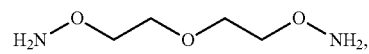

with a further compound selected from the group consisting of a polypeptide, a crosslinking compound, and a preliminary reaction product of a crosslinking compound and a polypeptide, wherein said contacting is under conditions that result in a first reaction product in which the O-[2-(2-aminooxy-ethoxy)-ethyl]-hydroxyl amine is conjugated via one —O—NH$_2$ group to the further compound, and
(ii) then contacting the first reaction product with HES of formula (I)

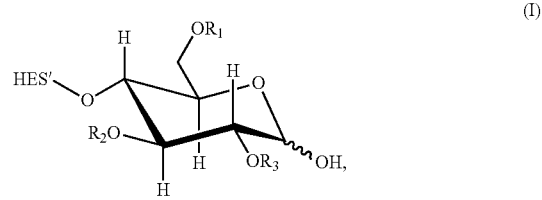

wherein $R_1$, $R_2$ and $R_3$ are independently hydrogen or a 2-hydroxyethyl group, and wherein said contacting is under conditions that result in a further reaction product in which the O-[2-(2-aminooxyethoxy)-ethyl]-hydroxyl amine is conjugated via its remaining —O—NH$_2$ group to the HES of formula (I) at its reducing end which is not oxidized prior to said contacting.

26. The method of claim 25, wherein the further compound is a polypeptide.

27. The method of claim 26, wherein said contacting of step (i) results in a first reaction product in which the polypeptide is conjugated to the O-[2-(2-aminooxy-ethoxy)-ethyl]-hydroxyl amine via an oxidized carbohydrate moiety comprised in the polypeptide.

28. The method of claim 25, comprising contacting the O-[2-(2-aminooxy-ethoxy)-ethyl]-hydroxyl amine with the further compound at a temperature in the range of from 4 to 37° C.

29. The method of claim 25, comprising contacting the O-[2-(2-aminooxy-ethoxy)-ethyl]-hydroxyl amine with the further compound in an aqueous medium.

30. The method of claim 25, wherein the further compound is a crosslinking compound.

31. The method of claim 25, wherein the further compound is a preliminary reaction product of a crosslinking compound and a polypeptide.

32. A method of producing a HES derivative, comprising contacting HES of formula (I)

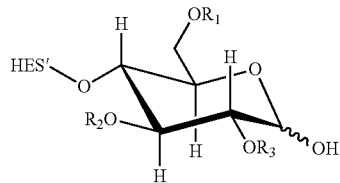

in an aqueous medium with O-[2-(2-aminooxy-ethoxy)-ethyl]-hydroxyl amine, having the structure

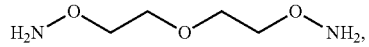

or with a polypeptide-modified derivative thereof, wherein $R_1$, $R_2$ and $R_3$ are independently hydrogen or a 2-hydroxyethyl group, and wherein said contacting is carried out under conditions that result in a reaction product in which the O-[2-(2-aminooxy-ethoxy)-ethyl]-hydroxyl amine is conjugated via one —O—$NH_2$ group to the HES of formula (I) at its reducing end which is not oxidized prior to said contacting.

33. The method of claim 32, wherein the HES of formula (I) is contacted with O-[2-(2-aminooxy-ethoxy)-ethyl]-hydroxyl amine to give the reaction product, and wherein the method further comprises contacting the remaining —O—$NH_2$ group of the O-[2-(2-aminooxy-ethoxy)-ethyl]-hydroxyl amine in the reaction product in an aqueous medium with a polypeptide to give a further reaction product in which the remaining —O—$NH_2$ group of the O-[2-(2-aminooxy-ethoxy)-ethyl]-hydroxyl amine is conjugated to an oxidized carbohydrate moiety comprised in the polypeptide.

34. The method of claim 32, comprising:
(1) first contacting the O-[2-(2-aminooxy-ethoxy)-ethyl]-hydroxyl amine in an aqueous medium with a polypeptide to give a first reaction product, said first reaction product being a polypeptide-modified derivative of O-[2-(2-aminooxy-ethoxy)-ethyl]-hydroxyl amine in which the O-[2-(2-aminooxy-ethoxy)-ethyl]-hydroxyl amine is conjugated via one of its —O—$NH_2$ groups to an oxidized carbohydrate moiety comprised in the polypeptide, and
(2) then contacting the polypeptide-modified derivative of O-[2-(2-aminooxy-ethoxy)-ethyl]-hydroxyl amine with the HES of formula (I) to give a further reaction product.

35. A method of producing a HES derivative, comprising contacting HES of formula (I)

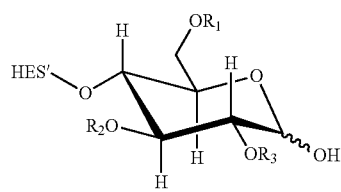

with O-[2-(2-aminooxy-ethoxy)-ethyl]-hydroxyl amine, having the structure

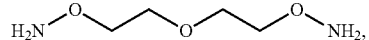

wherein $R_1$, $R_2$ and $R_3$ are independently hydrogen or a 2-hydroxyethyl group, wherein said contacting is in an aqueous medium at a pH from 4.5 to 6.5 and a temperature of 10° C. to 30° C. for two hours to 48 hours, and wherein said contacting results in a reaction product in which the O-[2-(2-aminooxy-ethoxy)-ethyl]-hydroxyl amine is conjugated via one —O—$NH_2$ group to the HES of formula (I) at its reducing end which is not oxidized prior to said contacting.

* * * * *